United States Patent
Sugimoto et al.

(10) Patent No.: US 10,428,056 B2
(45) Date of Patent: *Oct. 1, 2019

(54) HETEROCYCLIC COMPOUND

(71) Applicant: Takeda Pharmaceutical Company Limited, Osaka-shi, Osaka (JP)

(72) Inventors: Takahiro Sugimoto, Kanagawa (JP); Shinkichi Suzuki, Kanagawa (JP); Hiroki Sakamoto, Kanagawa (JP); Masami Yamada, Kanagawa (JP); Minoru Nakamura, Kanagawa (JP); Makoto Kamata, Kanagawa (JP); Kenichiro Shimokawa, Kanagawa (JP); Masataka Murakami, Kanagawa (JP); Jinichi Yonemori, Kanagawa (JP); Takuto Kojima, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,635

(22) Filed: Aug. 27, 2018

(65) Prior Publication Data

US 2018/0362516 A1 Dec. 20, 2018

Related U.S. Application Data

(63) Continuation of application No. 15/799,379, filed on Oct. 31, 2017, now Pat. No. 10,087,150, which is a (Continued)

(30) Foreign Application Priority Data

Jun. 26, 2015 (JP) .................. 2015-129043
Oct. 20, 2015 (JP) .................. 2015-206797

(51) Int. Cl.
| | |
|---|---|
| C07D 471/04 | (2006.01) |
| C07D 413/14 | (2006.01) |
| C07D 413/04 | (2006.01) |
| C07D 413/06 | (2006.01) |
| C07D 413/10 | (2006.01) |
| C07D 417/06 | (2006.01) |
| C07D 265/22 | (2006.01) |
| C07D 491/107 | (2006.01) |
| C07F 7/02 | (2006.01) |
| A61P 25/28 | (2006.01) |
| C07D 417/10 | (2006.01) |
| C07F 7/08 | (2006.01) |

(52) U.S. Cl.
CPC ........... *C07D 413/14* (2013.01); *A61P 25/28* (2018.01); *C07D 265/22* (2013.01); *C07D 413/04* (2013.01); *C07D 413/06* (2013.01); *C07D 413/10* (2013.01); *C07D 417/06* (2013.01); *C07D 417/10* (2013.01); *C07D 471/04* (2013.01); *C07D 491/107* (2013.01); *C07F 7/02* (2013.01); *C07F 7/0814* (2013.01); *C07B 2200/07* (2013.01)

(58) Field of Classification Search
CPC .. C07D 471/04; C07D 413/14; C07D 413/06; C07D 413/10; C07D 417/06; C07D 491/107; C07D 265/22; C07B 2200/07; C07F 7/02
USPC ....................... 544/105; 514/230.5
See application file for complete search history.

(56) References Cited

U.S. PATENT DOCUMENTS

| | | |
|---|---|---|
| 5,486,512 A | 1/1996 | Gregor |
| 5,538,983 A | 7/1996 | Buxbaum et al. |
| | (Continued) | |

FOREIGN PATENT DOCUMENTS

| | | |
|---|---|---|
| JP | 2001-131173 | 5/2001 |
| WO | 94/00448 | 1/1994 |
| | (Continued) | |

OTHER PUBLICATIONS

Wess, Jurgen et al. Muscarinic acetylcholine receptors: mutant mice provide new insights for drug development. Nature Reviews Drug Discovery. vol. 6, Sep. 2007, pp. 721-733.

(Continued)

*Primary Examiner* — Kahsay Habte
(74) *Attorney, Agent, or Firm* — Hamre, Schumann, Mueller & Larson, P.C.

(57) ABSTRACT

The present invention provides a compound having a cholinergic muscarinic M1 receptor positive allosteric modulator activity, which may be useful as a prophylactic or therapeutic drug for Alzheimer's disease, schizophrenia, pain, sleep disorder, Parkinson's disease dementia, dementia with Lewy bodies and the like. The present invention relates to a compound represented by the formula (I) or a salt thereof:

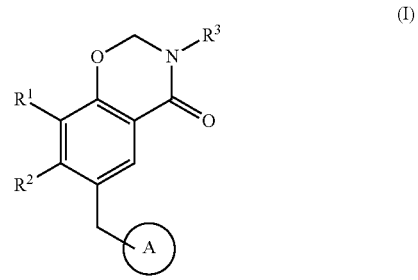

wherein each symbol is as defined in the attached DESCRIPTION.

2 Claims, No Drawings

Related U.S. Application Data continuation of application No. 15/190,642, filed on Jun. 23, 2016, now Pat. No. 9,878,989.

(56) References Cited

U.S. PATENT DOCUMENTS

| | | | |
|---|---|---|---|
| 5,744,476 | A | 4/1998 | Locke et al. |
| 6,569,897 | B1 | 5/2003 | Cushman et al. |
| 7,678,363 | B2 | 3/2010 | Barlow et al. |
| 9,315,458 | B2 | 4/2016 | Yamada et al. |
| 9,403,802 | B2 | 8/2016 | Sakamoto et al. |
| 9,499,516 | B2 | 11/2016 | Yamada et al. |
| 9,518,042 | B2 | 12/2016 | Yamada et al. |
| 9,549,928 | B2 | 1/2017 | Messer et al. |
| 9,878,989 | B2 * | 1/2018 | Sugimoto ............ C07F 7/02 |
| 10,087,150 | B2 * | 10/2018 | Sugimoto ............ C07F 7/02 |
| 2003/0220315 | A1 | 11/2003 | Cushman et al. |
| 2004/0023951 | A1 | 2/2004 | Bymaster et al. |
| 2004/0044023 | A1 | 3/2004 | Cantillon |
| 2004/0102450 | A1 | 5/2004 | Ewing et al. |
| 2004/0266659 | A1 | 12/2004 | LaBerge |
| 2006/0009414 | A1 | 1/2006 | Frey, II et al. |
| 2006/0233843 | A1 | 10/2006 | Conn et al. |
| 2007/0049576 | A1 | 3/2007 | Barlow et al. |
| 2009/0082342 | A1 | 3/2009 | Uldam et al. |
| 2009/0082388 | A1 | 3/2009 | Hacksell et al. |
| 2009/0124604 | A1 | 5/2009 | Nash et al. |
| 2009/0124609 | A1 | 5/2009 | Albrecht et al. |
| 2009/0318436 | A1 | 12/2009 | Albrecht et al. |
| 2010/0120842 | A1 | 5/2010 | Barlow et al. |
| 2010/0152169 | A1 | 6/2010 | Nash et al. |
| 2010/0256120 | A1 | 10/2010 | Brown et al. |
| 2011/0020423 | A1 | 1/2011 | Elenko et al. |
| 2011/0319386 | A1 | 12/2011 | Barlow et al. |
| 2012/0046273 | A1 | 2/2012 | Twose et al. |
| 2012/0129877 | A1 | 5/2012 | Martinez Gil et al. |
| 2013/0116272 | A1 | 5/2013 | Kuduk et al. |
| 2013/0184298 | A1 | 7/2013 | Kuduk et al. |
| 2013/0289019 | A1 | 10/2013 | Chau |
| 2014/0088119 | A1 | 3/2014 | Messer et al. |
| 2014/0099356 | A1 | 4/2014 | Elenko et al. |
| 2014/0349976 | A1 | 11/2014 | Hacksell et al. |
| 2015/0126487 | A1 | 5/2015 | Sakamoto et al. |
| 2015/0265593 | A1 | 9/2015 | Elenko et al. |
| 2015/0307451 | A1 | 10/2015 | Yamada et al. |
| 2015/0307497 | A1 | 10/2015 | Sugimoto |
| 2016/0152598 | A1 | 6/2016 | Yamada et al. |
| 2016/0152603 | A1 | 6/2016 | Yamada et al. |
| 2017/0081332 | A1 | 3/2017 | Sugimoto et al. |
| 2017/0095465 | A1 | 4/2017 | Elenko et al. |
| 2017/0112820 | A1 | 4/2017 | Elenko et al. |
| 2017/0121308 | A1 | 5/2017 | Ogino et al. |
| 2018/0250270 | A1 | 9/2018 | Chase et al. |

FOREIGN PATENT DOCUMENTS

| | | |
|---|---|---|
| WO | 96/00062 | 1/1996 |
| WO | 98/30243 | 7/1998 |
| WO | 99/36384 | 7/1999 |
| WO | 99/37304 | 7/1999 |
| WO | 00/32590 | 6/2000 |
| WO | 01/07436 | 2/2001 |
| WO | 01/46192 | 6/2001 |
| WO | 02/03684 | 1/2002 |
| WO | 02/074293 | 9/2002 |
| WO | 03/045315 | 6/2003 |
| WO | 2004/073639 | 9/2004 |
| WO | 2004/087158 | 10/2004 |
| WO | 2006/090143 | 8/2006 |
| WO | 2006/113485 | 10/2006 |
| WO | 2007/020411 | 2/2007 |
| WO | 2007/025177 | 3/2007 |
| WO | 2007/044937 | 4/2007 |
| WO | 2007/075567 | 7/2007 |
| WO | 2007/125287 | 11/2007 |
| WO | 2007/125290 | 11/2007 |
| WO | 2007/125293 | 11/2007 |
| WO | 2008/008539 | 1/2008 |
| WO | 2008/036843 | 3/2008 |
| WO | 2008/113072 | 9/2008 |
| WO | 2009/032116 | 3/2009 |
| WO | 2009/032124 | 3/2009 |
| WO | 2009/032125 | 3/2009 |
| WO | 2009/039460 | 3/2009 |
| WO | 2009/064848 | 5/2009 |
| WO | 2009/064852 | 5/2009 |
| WO | 2009/091374 | 7/2009 |
| WO | 2010/042603 | 4/2010 |
| WO | 2010/059773 | 5/2010 |
| WO | 2010/096338 | 8/2010 |
| WO | 2010/102218 | 9/2010 |
| WO | 2010/123716 | 10/2010 |
| WO | 2011/011060 | 1/2011 |
| WO | 2011-025851 | 3/2011 |
| WO | 2011/049731 | 4/2011 |
| WO | 2011/075371 | 6/2011 |
| WO | 2011/084371 | 7/2011 |
| WO | 2011/159553 | 12/2011 |
| WO | 2012/003147 | 1/2012 |
| WO | 2012/047702 | 4/2012 |
| WO | 2012/149524 | 11/2012 |
| WO | 2012/170599 | 12/2012 |
| WO | 2013/129622 | 9/2013 |
| WO | 2013/142236 | 9/2013 |
| WO | 2014/077401 | 5/2014 |
| WO | 2014/102233 | 7/2014 |
| WO | 2014/117920 | 8/2014 |
| WO | 2014/176460 | 10/2014 |
| WO | 2014/182695 | 11/2014 |
| WO | 2015/163485 | 10/2015 |
| WO | 2015/174534 | 11/2015 |
| WO | 2015/190564 | 12/2015 |
| WO | 2017/044693 | 3/2017 |
| WO | 2017/069173 | 4/2017 |
| WO | 2017/155050 | 9/2017 |
| WO | 2018/122845 | 7/2018 |

OTHER PUBLICATIONS

International Search Report issued for PCT/JP2016/069189, dated Oct. 6, 2016, 5 pages.

Kuduk, Scott D. et al. Novel M1 allosteric ligands: a patent review, Expert Opinion on Therapeutic Patents, vol. 22, No. 12, Oct. 23, 2012, pp. 1385-1398. Online [retrieved on Sep. 22, 2016] retrieved at: <http://www.tandfonline.com/loi/ietp20>, 15 pages.

Adbul-Ridha, et al., "Mechanistic Insights into Allosteric Structure-Function Relationships at the M1 Muscarinic Acetylcholine Receptor", The Journal of Biological Chemistry, vol. 289, No. 48, pp. 33701-33711, Nov. 28, 2014.

Mistry, et al., "Novel Fused Arylpyrimidinone Based Allosteric Modulators of the M1 Muscarinic Acetylcholine Receptor", ACS Chemical Neuroscience, 2016, vol. 7, No. 5, pp. 647-661.

Reddy, et al., "Synthesis of 6,6'-methylenebisquinazolinones and 7,7'-methylenebis-1,4-benzodiazepine-2,5-diones", Indian Journal of Chemistry, Section B: Organic Chemistry Including Medicinal Chemistry, vol. 41B(11), Nov. 2002, pp. 2405-2409.

compound of CAS Registry No. 1497582-45-2.

International Search Report issued in related International Application No. PCT/JP2016/081016, dated Jan. 17, 2017, 4 pages.

Patani, et al., "Bioisosterism: A Rational Approach in Drug Design", Chem. Rev. 1996, 96, 3147-3176.

* cited by examiner

HETEROCYCLIC COMPOUND

TECHNICAL FIELD

The present invention relates to a heterocyclic compound which has a cholinergic muscarinic M1 receptor positive allosteric modulator activity and may be useful as a medicament such as an agent for the prophylaxis or treatment of Alzheimer's disease, schizophrenia, pain, sleep disorder, Parkinson's disease dementia, dementia with Lewy bodies and the like. As used herein, the positive allosteric modulator activity refers to an action to potentiate receptor function by binding at a different site from that of an endogenous activator (acetylcholine for this receptor).

BACKGROUND OF THE INVENTION

Acetylcholine is a neurotransmitter that induces signal transduction in the central nervous system and the neuromuscular connections (the parasympathetic nerve and motor nerve). In the central nervous system, nuclei of origin of the acetylcholine neuron are in the brain stem and forebrain, and those acetylcholine neurons project to cerebral cortex, hippocampus, and limbic area. In addition, some interneurons in some brain areas such as striatum utilize acetylcholine as a neurotransmitter. Acetylcholine receptor is classified into a ligand dependent-ion channel (cholinergic nicotinic receptor) and a G-protein-coupled receptor (cholinergic muscarinic receptor). The cholinergic muscarinic receptor is one kind of receptor for excitatory neurotransmitter, acetylcholine, and was named based on the selective activation of the receptor by muscarine. The muscarinic receptor is further classified into subtypes of M1 to M5. The M1 receptor is known to be mainly distributed in the brain, and deeply involved particularly in learning, memory, sleep, neuropathic pain, and the like. The importance of cholinergic muscarinic M1 receptor in brain physiology is well known, and a compound which enhances M1 receptor function is expected to be useful as an agent for the prophylaxis or treatment of mental diseases, neurodegenerative diseases, memory disorders, pain, sleep disorders, Parkinson's disease dementia, dementia with Lewy bodies and the like (non-patent document 1).

Patent document 1 discloses the following compound that binds as a ligand of human peroxisome proliferator-activated receptor γ (PPARγ) to the receptor and activates same to show a strong hypoglycemic action.

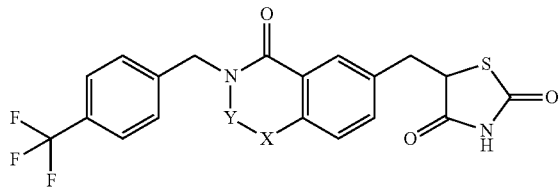

(1)

wherein each symbol is as defined in the document.

Patent document 2 discloses the following compound, which has a cholinergic muscarinic M1 receptor positive allosteric modulator activity and is useful as a prophylactic or therapeutic drug for Alzheimer's disease, schizophrenia, pain, sleep disorder and the like.

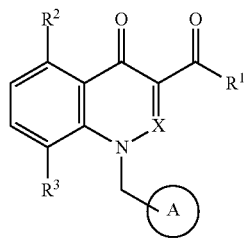

(I)

wherein each symbol is as defined in the document.

Patent document 3 discloses the following compound, which has a cholinergic muscarinic M1 receptor positive allosteric modulator activity and is useful as a prophylactic or therapeutic drug for Alzheimer's disease, schizophrenia, pain, sleep disorder and the like.

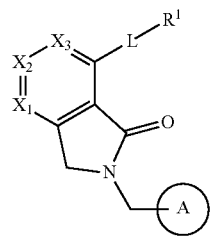

(I)

wherein each symbol is as defined in the document.

Patent document 4 discloses the following compound, which has a cholinergic muscarinic M1 receptor positive allosteric modulator activity and is useful as a prophylactic or therapeutic drug for Alzheimer's disease, schizophrenia, pain, sleep disorder, Parkinson's disease dementia, dementia with Lewy bodies and the like.

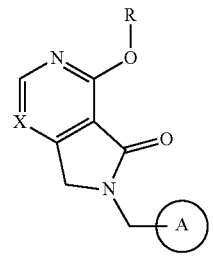

(I)

wherein each symbol is as defined in the document.

Patent document 5 discloses the following compound, which has a cholinergic muscarinic M1 receptor positive allosteric modulator activity and is useful as a prophylactic or therapeutic drug for Alzheimer's disease, schizophrenia, pain, sleep disorder, Parkinson's disease dementia, dementia with Lewy bodies and the like.

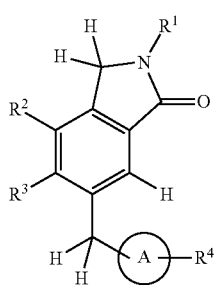

(I)

wherein each symbol is as defined in the document.

Patent document 6 discloses the following compound, which has a cholinergic muscarinic M1 receptor positive allosteric modulator activity and is useful as a prophylactic or therapeutic drug for Alzheimer's disease, schizophrenia, pain, sleep disorder, Parkinson's disease dementia, dementia with Lewy bodies and the like.

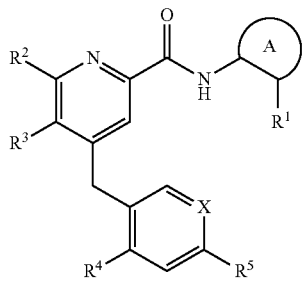

(I)

wherein each symbol is as defined in the document.

DOCUMENT LIST

Patent Documents patent document 1: JP-A-2001-131173
patent document 2: WO 2013/129622
patent document 3: WO 2014/077401
patent document 4: WO 2015/174534
patent document 5: WO 2015/163485
patent document 6: WO 2015/190564

Non-Patent Document non-patent document 1: Nature Reviews Drug Discovery, 2007, 6, 721-733.

SUMMARY OF THE INVENTION

Problems to be Solved by the Invention

The development of a compound having a cholinergic muscarinic M1 receptor (M1 receptor) positive allosteric modulator activity and useful as an agent for the prophylaxis or treatment of for Alzheimer's disease, schizophrenia, pain, sleep disorder, Parkinson's disease dementia, dementia with Lewy bodies and the like is desired.

Means of Solving the Problems

The present inventors have conducted intensive studies in an attempt to solve the aforementioned problems and found that a compound represented by the following formula (I) may have a cholinergic muscarinic M1 receptor positive allosteric modulator activity, which resulted in the completion of the present invention.

Accordingly, the present invention relates to the following.

[1] A compound represented by the formula

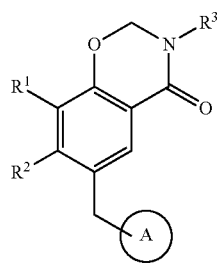

(I)

wherein
R$^1$ and R$^2$ are each independently a hydrogen atom or a substituent, or
a partial structure:

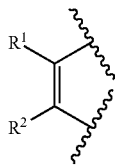

is optionally

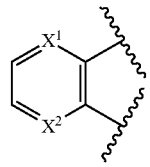

(wherein X$^1$ and X$^2$ are each independently CH or N),
R$^3$ is a hydrogen atom, an optionally substituted C$_{1-6}$ alkyl group or an optionally substituted cyclic group, and
ring A is a ring which is optionally further substituted, excluding 6-[(2,4-dioxothiazolidin-5-yl)methyl]-3-[((4-trifluoromethyl)phenyl)methyl]-1,3-benzoxazin-4-one, or a salt thereof (sometimes to be abbreviated as "compound (I)" in the present specification).

[2] The compound described in [1], wherein R$^3$ is (1) a hydrogen atom, (2) a C$_{1-6}$ alkyl group optionally substituted by 1 to 3 substituents selected from a hydroxy group and a 3- to 14-membered non-aromatic heterocyclic group, (3) a C$_{3-10}$ cycloalkyl group optionally substituted by 1 to 3 hydroxy groups, (4) a C$_{6-14}$ aryl group optionally substituted by 1 to 3 halogen atoms or (5) a 3- to 14-membered non-aromatic heterocyclic group optionally substituted by 1 to 3 hydroxy groups, or a salt thereof.

[3] The compound described in [1], wherein the ring A is an optionally further substituted 6-membered aromatic ring, or a salt thereof.

[4] The compound described in [1], wherein the ring A is a 6-membered aromatic ring optionally further substituted by 1 to 5 substituents selected from (i) a halogen atom,
(ii) a cyano group,
(iii) a $C_{1-6}$ alkyl group,
(iv) a $C_{2-6}$ alkenyl group,
(v) a $C_{2-6}$ alkynyl group optionally substituted by a tri-$C_{1-6}$ alkylsilyl group,
(vi) a $C_{1-6}$ alkoxy group and
(vii) a 5- to 14-membered aromatic heterocyclic group optionally substituted by 1 to 3 substituents selected from a halogen atom and a $C_{1-6}$ alkyl group,
or a salt thereof.

[5] The compound described in [1], wherein at least one of $R^1$ and $R^2$ is a substituent, or a salt thereof.

[6] The compound described in [1], wherein $R^1$ is a hydrogen atom, a halogen atom or a $C_{1-6}$ alkyl group;

$R^2$ is a hydrogen atom, a halogen atom, a $C_{1-6}$ alkyl group, a $C_{2-6}$ alkenyl group or a $C_{1-6}$ alkoxy group; or the partial structure:

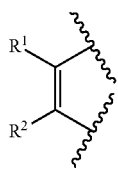

is

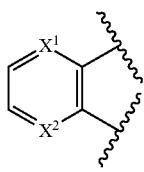

(wherein $X^1$ and $X^2$ are each CH);

$R^3$ is a hydrogen atom, an optionally substituted $C_{1-6}$ alkyl group, an optionally substituted $C_{3-10}$ cycloalkyl group, an optionally substituted $C_{6-14}$ aryl group or an optionally substituted 3- to 14-membered non-aromatic heterocyclic group; and ring A is a $C_{6-14}$ aromatic hydrocarbon ring, a 3- to 14-membered non-aromatic heterocycle or a 5- to 14-membered aromatic heterocycle, each of which is optionally further substituted, or a salt thereof.

[7] The compound described in [1], wherein $R^1$ is a hydrogen atom, a halogen atom or a $C_{1-6}$ alkyl group;

$R^2$ is a hydrogen atom, a halogen atom, a $C_{1-6}$ alkyl group, a $C_{2-6}$ alkenyl group or a $C_{1-6}$ alkoxy group; or the partial structure:

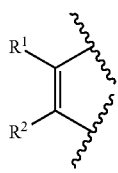

is

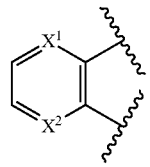

(wherein $X^1$ and $X^2$ are each CH);

$R^3$ is
(1) a hydrogen atom,
(2) a $C_{1-6}$ alkyl group optionally substituted by 1 to 3 substituents selected from a hydroxy group and a 3- to 14-membered non-aromatic heterocyclic group,
(3) a $C_{3-10}$ cycloalkyl group optionally substituted by 1 to 3 hydroxy groups,
(4) a $C_{6-14}$ aryl group optionally substituted by 1 to 3 halogen atoms or
(5) a 3- to 14-membered non-aromatic heterocyclic group optionally substituted by 1 to 3 hydroxy groups; and ring A is a $C_{6-14}$ aromatic hydrocarbon ring, a 3- to 14-membered non-aromatic heterocycle or a 5- to 14-membered aromatic heterocycle, each of which is optionally further substituted by 1 to 5 substituents selected from
(i) a halogen atom,
(ii) a cyano group,
(iii) an oxo group,
(iv) a $C_{1-6}$ alkyl group optionally substituted by 1 to 3 halogen atoms,
(v) a $C_{2-6}$ alkenyl group,
(vi) a $C_{2-6}$ alkynyl group optionally substituted by a tri-$C_{1-6}$ alkylsilyl group,
(vii) a $C_{1-6}$ alkoxy group,
(viii) a $C_{1-6}$ alkoxy-carbonyl group and
(ix) a 5- to 14-membered aromatic heterocyclic group optionally substituted by 1 to 3 substituents selected from a halogen atom and a $C_{1-6}$ alkyl group,
or a salt thereof.

[8] The compound described in [1], wherein $R^1$ is a hydrogen atom, a halogen atom or a $C_{1-6}$ alkyl group;

$R^2$ is a hydrogen atom, a halogen atom, a $C_{1-6}$ alkyl group, a $C_{2-6}$ alkenyl group or a $C_{1-6}$ alkoxy group; or the partial structure:

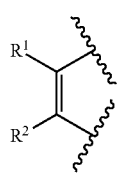

is

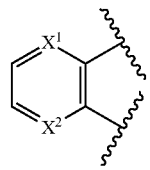

(wherein $X^1$ and $X^2$ are each CH);

R³ is
(1) a hydrogen atom,
(2) a $C_{1-6}$ alkyl group optionally substituted by 1 to 3 substituents selected from a hydroxy group and a 3- to 14-membered non-aromatic heterocyclic group,
(3) a $C_{3-10}$ cycloalkyl group optionally substituted by 1 to 3 hydroxy groups,
(4) a $C_{6-14}$ aryl group optionally substituted by 1 to 3 halogen atoms or
(5) a 3- to 14-membered non-aromatic heterocyclic group optionally substituted by 1 to 3 hydroxy groups; and
ring A is a 6-membered aromatic ring optionally further substituted by 1 to 5 substituents selected from
(i) a halogen atom,
(ii) a cyano group,
(iii) a $C_{1-6}$ alkyl group,
(iv) a $C_{2-6}$ alkenyl group,
(v) a $C_{2-6}$ alkynyl group optionally substituted by a tri-$C_{1-6}$ alkylsilyl group,
(vi) a $C_{1-6}$ alkoxy group and
(vii) a 5- to 14-membered aromatic heterocyclic group optionally substituted by 1 to 3 substituents selected from a halogen atom and a $C_{1-6}$ alkyl group,
or a salt thereof.

[9] The compound described in [1], wherein R¹ is a hydrogen atom, a halogen atom or a $C_{1-6}$ alkyl group;
R² is a $C_{1-6}$ alkyl group, a $C_{2-6}$ alkenyl group or a $C_{1-6}$ alkoxy group; or
the partial structure:

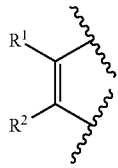

is

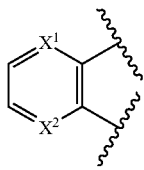

(wherein X¹ and X² are each CH);
R³ is
(1) a $C_{3-10}$ cycloalkyl group optionally substituted by 1 to 3 hydroxy groups or
(2) a 3- to 14-membered non-aromatic heterocyclic group optionally substituted by 1 to 3 hydroxy groups; and
ring A is a $C_{6-14}$ aromatic hydrocarbon ring, a 3- to 14-membered non-aromatic heterocycle or a 5- to 14-membered aromatic heterocycle, each of which is optionally further substituted by 1 to 5 substituents selected from
(i) a halogen atom,
(ii) a cyano group,
(iii) a $C_{1-6}$ alkyl group,
(iv) a $C_{1-6}$ alkoxy group and
(v) a 5- to 14-membered aromatic heterocyclic group optionally substituted by 1 to 3 $C_{1-6}$ alkyl groups,
or a salt thereof.

[10] The compound described in [1], wherein R¹ is a hydrogen atom, a halogen atom or a $C_{1-6}$ alkyl group:
R² is a $C_{1-6}$ alkyl group, a $C_{2-6}$ alkenyl group or a $C_{1-6}$ alkoxy group:
R³ is
(1) a $C_{3-10}$ cycloalkyl group optionally substituted by 1 to 3 hydroxy groups or
(2) a 3- to 14-membered non-aromatic heterocyclic group optionally substituted by 1 to 3 hydroxy groups: and
ring A is a $C_{6-14}$ aromatic hydrocarbon ring, a 3- to 14-membered non-aromatic heterocycle or a 5- to 14-membered aromatic heterocycle, each of which is optionally further substituted by 1 to 5 substituents selected from
(i) a halogen atom,
(ii) a cyano group,
(iii) a $C_{1-6}$ alkyl group,
(iv) a $C_{1-6}$ alkoxy group and
(v) a 5- to 14-membered aromatic heterocyclic group optionally substituted by 1 to 3 $C_{1-6}$ alkyl groups,
or a salt thereof.

[11] The compound described in [1], wherein R¹ is a hydrogen atom or a halogen atom:
R² is a $C_{1-6}$ alkyl group:
R³ is
(1) a $C_{3-10}$ cycloalkyl group optionally substituted by 1 to 3 hydroxy groups or
(2) a 3- to 14-membered non-aromatic heterocyclic group optionally substituted by 1 to 3 hydroxy groups: and
ring A is a $C_{6-14}$ aromatic hydrocarbon ring or a 5- to 14-membered aromatic heterocycle, each of which is optionally further substituted by 1 to 5 substituents selected from
(i) a halogen atom,
(ii) a $C_{1-6}$ alkyl group and
(iii) a 5- to 14-membered aromatic heterocyclic group optionally substituted by 1 to 3 $C_{1-6}$ alkyl groups,
or a salt thereof.

[12] 8-Fluoro-3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one, or a salt thereof.

[13] 8-Chloro-6-((6-chloropyridin-3-yl)methyl)-3-((1S,2S)-2-hydroxycyclopentyl)-7-methyl-2,3-dihydro-4H-1,3-benzoxazin-4-one, or a salt thereof.

[14] 3-(trans-2-Hydroxycyclohexyl)-7-methyl-6-((6-methylpyridin-3-yl)methyl)-2,3-dihydro-4H-1,3-benzoxazin-4-one, or a salt thereof.

[15] 3-((3S,4S)-4-Hydroxytetrahydro-2H-pyran-3-yl)-7-methyl-6-(4-(1-methyl-1H-pyrazol-3-yl)benzyl)-2,3-dihydro-4H-1,3-benzoxazin-4-one, or a salt thereof.

[16] A medicament comprising the compound described in [1] or a salt thereof.

[17] The medicament described in [16], which is a cholinergic muscarinic M1 receptor positive allosteric modulator.

[18] The medicament described in [16], which is a prophylactic or therapeutic drug for Alzheimer's disease, schizophrenia, pain, sleep disorder, Parkinson's disease dementia or dementia with Lewy bodies.

[19] The compound described in [1] or a salt thereof, for use for the prophylaxis or treatment of Alzheimer's disease, schizophrenia, pain, sleep disorder, Parkinson's disease dementia or dementia with Lewy bodies.

[20] A method of cholinergic muscarinic M1 receptor positive allosteric modulation in a mammal, which comprises administering an effective amount of the compound described in [1] or a salt thereof to the mammal.

[21] A method for the prophylaxis or treatment of Alzheimer's disease, schizophrenia, pain, sleep disorder, Parkinson's disease dementia or dementia with Lewy bodies in a mammal, which comprises administering an effective amount of the compound described in [1] or a salt thereof to the mammal.

[22] Use of the compound described in [1] or a salt thereof for the production of an agent for the prophylaxis or treatment of Alzheimer's disease, schizophrenia, pain, sleep disorder, Parkinson's disease dementia or dementia with Lewy bodies.

Effect of the Invention

The compound of the present invention may have a cholinergic muscarinic M1 receptor positive allosteric modulator activity, and may be useful as an agent for the prophylaxis or treatment of, for example, Alzheimer's disease, schizophrenia, pain, sleep disorder, Parkinson's disease dementia, dementia with Lewy bodies and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5 halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5 halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5 halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5 halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-4}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),

(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkylcarbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane, and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include aromatic heterocycle and non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzoimidazole, benzooxazole, benzoisoxazole, benzothiazole, benzoisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, Pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzoimidazole, dihydrobenzooxazole, dihydrobenzothiazole, dihydrobenzoisothiazole, dihydronaphto[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "cyclic group" of the "optionally substituted cyclic group" include the above-mentioned "$C_{3-10}$ cycloalkyl group", "$C_{3-10}$ cycloalkenyl group", "$C_{6-14}$ aryl group" and "heterocyclic group", and examples of the substituent thereof include the above-mentioned "substituent".

In the present specification, examples of the "ring" of the "optionally further substituted ring" include the above-mentioned "hydrocarbon ring" and the above-mentioned "heterocycle", and examples of the substituent thereof include the above-mentioned "substituent".

In the present specification, examples of the "6-membered aromatic ring" of the "optionally further substituted 6-membered aromatic ring" include benzene ring and 6-membered ones in the above-mentioned "aromatic heterocycle", and examples of the substituent thereof include the above-mentioned "substituent".

Each symbol in the formula (I) is explained below.

$R^1$ and $R^2$ are each independently a hydrogen atom or a substituent.

Examples of the "substituent" for $R^1$ or $R^2$ include a halogen atom (e.g., fluorine, chlorine), a $C_{1-6}$ alkyl group (e.g., methyl), a $C_{2-6}$ alkenyl group (e.g., ethenyl), a $C_{1-6}$ alkoxy group (e.g., methoxy) and the like.

$R^1$ is preferably a hydrogen atom, a halogen atom (e.g., fluorine, chlorine) or a $C_{1-6}$ alkyl group (e.g., methyl), more preferably, a hydrogen atom or a halogen atom (e.g., fluorine, chlorine).

$R^2$ is preferably a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy), more preferably, a $C_{1-6}$ alkyl group (e.g., methyl, ethyl), a $C_{2-6}$ alkenyl group (e.g., ethenyl) or a $C_{1-6}$ alkoxy group (e.g., methoxy), further preferably, a $C_{1-6}$ alkyl group (e.g., methyl, ethyl) or a $C_{1-6}$ alkoxy group (e.g., methoxy), particularly preferably, a $C_{1-6}$ alkyl group (e.g., methyl).

In another embodiment of the present invention, at least one of $R^1$ and $R^2$ is preferably a substituent (both $R^1$ and $R^2$ are not hydrogen atoms at the same time).

The partial structure:

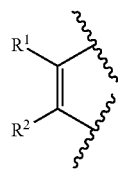

may be

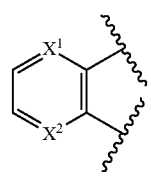

(wherein $X^1$ and $X^2$ are each independently CH or N).

$X^1$ and $X^2$ are each preferably CH.

$R^3$ is a hydrogen atom, an optionally substituted $C_{1-6}$ alkyl group or an optionally substituted cyclic group.

Examples of the "substituent" of the "optionally substituted $C_{1-6}$ alkyl group" for $R^3$ include a hydroxy group, a 3- to 14-membered non-aromatic heterocyclic group (e.g., tetrahydrofuranyl) and the like.

Examples of the "cyclic group" of the "optionally substituted cyclic group" for $R^3$ include a $C_{3-10}$ cycloalkyl group (e.g., cyclopentyl, cyclohexyl), a $C_{6-14}$ aryl group (e.g., phenyl), a 3- to 14-membered non-aromatic heterocyclic group (e.g., tetrahydropyranyl) and the like. Examples of the "substituent" include a halogen atom (e.g., fluorine), a hydroxy group and the like.

$R^3$ is preferably a hydrogen atom, an optionally substituted $C_{1-6}$ alkyl group (e.g., methyl, isobutyl), an optionally substituted $C_{3-10}$ cycloalkyl group (e.g., cyclopentyl, cyclohexyl), an optionally substituted $C_{6-14}$ aryl group (e.g., phenyl) or an optionally substituted 3- to 14-membered non-aromatic heterocyclic group (e.g., tetrahydropyranyl), more preferably, (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups, further preferably, (1) a $C_{3-10}$ cycloalkyl group (e.g., cyclopentyl, cyclohexyl) optionally substituted by 1 to 3 hydroxy groups or (2) a 3- to 14-membered non-aromatic heterocyclic group (e.g., tetrahydropyranyl) optionally substituted by 1 to 3 hydroxy groups.

In another embodiment of the present invention, $R^3$ is preferably an optionally substituted cyclic group.

Ring A is a ring which is optionally further substituted.

Examples of the "ring" of the "optionally substituted ring" for ring A include a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring), a 5- to 14-membered aromatic heterocycle (e.g., pyridine ring, indazole ring, pyrazolopyridine ring) and the like.

The "ring" of the "optionally further substituted ring" for ring A optionally has 1 to 5 (preferably 1 to 3) substituents at substitutable positions. Examples of the substituent include a halogen atom (e.g., fluorine, chlorine), a cyano group, an oxo group, an optionally substituted $C_{1-6}$ alkyl group (e.g., methyl, ethyl), a $C_{2-6}$ alkenyl group (e.g., ethenyl), an optionally substituted $C_{2-6}$ alkynyl group (e.g., ethynyl), a $C_{1-6}$ alkoxy group (e.g., methoxy), a $C_{1-6}$ alkoxy-carbonyl group (e.g., methoxycarbonyl), an optionally substituted 5- to 14-membered aromatic heterocyclic group (e.g., pyrazolyl, imidazolyl, triazolyl, pyridyl, pyridazinyl) and the like. When plural substituents are present, the respective substituents may be the same or different.

Ring A is preferably a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted, more preferably, a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) an oxo group, (iv) $C_{1-6}$ alkyl group (e.g., methyl, ethyl) optionally substituted by 1 to 3 halogen atoms (e.g., fluorine), (v) a $C_{2-6}$ alkenyl group (e.g., ethenyl), (vi) a $C_{2-6}$ alkynyl group (e.g., ethynyl) optionally substituted by a tri-$C_{1-6}$ alkylsilyl group (e.g., trimethylsilyl), (vii) a $C_{1-6}$ alkoxy group (e.g., methoxy), (viii) a $C_{1-6}$ alkoxy-carbonyl group (e.g., methoxycarbonyl) and (ix) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl), further preferably, (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., azetidine ring, pyrrolidine ring, piperidine ring, piperazine ring, morpholine ring, thiomorpholine ring, oxaazaspirononane ring) optionally further substituted by 1 to 5 (preferably 1 to 3) substituents selected from (i) a halogen atom (e.g., fluorine), (ii) a cyano group, (iii) an oxo group, (iv) a $C_{1-6}$ alkyl group (e.g., methyl) optionally substituted by 1 to 3 halogen atoms (e.g., fluorine), (v) a $C_{1-6}$ alkoxy group (e.g., methoxy) and (vi) a $C_{1-6}$ alkoxy-carbonyl group (e.g., methoxycarbonyl), or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl), particularly preferably, a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring), each of which is optionally further substituted by 1 to 5 (preferably 1 to 3) substituents selected from (i) a halogen atom (e.g., chlorine), (ii) a cyano group, (iii) a $C_{1-6}$ alkyl group (e.g., methyl), (iv) a $C_{1-6}$ alkoxy group (e.g., methoxy) and (v) a 5- to 14-membered aromatic heterocyclic group (e.g., pyrazolyl) optionally substituted by 1 to 3 $C_{1-6}$ alkyl groups (e.g., methyl), more particularly preferably, $C_{6-14}$ aromatic hydrocarbon ring (e.g., benzene ring) or a 5- to 14-membered aromatic heterocycle (e.g., pyridine ring), each of which is optionally further substituted by 1 to 5 (preferably 1 to 3) substituents selected from (i) a halogen atom (e.g., chlorine), (ii) a $C_{1-6}$ alkyl group (e.g., methyl), (iii) a $C_{1-6}$ alkoxy group (e.g., methoxy) and (iv) a 5- to 14-membered aromatic heterocyclic group (e.g., pyrazolyl) optionally substituted by 1 to 3 $C_{1-6}$ alkyl groups (e.g., methyl), particularly further preferably, a $C_{6-14}$ aromatic hydrocarbon ring (e.g., benzene ring) or a 5- to 14-membered aromatic heterocycle (e.g., pyridine ring), each of which is optionally further substituted by 1 to 5 (preferably 1 to 3) substituents selected from (i) a halogen atom (e.g., chlorine), (ii) a $C_{1-6}$ alkyl group (e.g., methyl) and (iii) a 5- to 14-membered aromatic heterocyclic group (e.g., pyrazolyl) optionally substituted by 1 to 3 $C_{1-6}$ alkyl groups (e.g., methyl).

In another embodiment of the present invention, ring A is preferably a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring, indazole ring, pyrazolopyridine ring), each of which is optionally further substituted, more preferably, a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) $C_{1-6}$ alkyl group (e.g., methyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl), further preferably, (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., piperidine ring) optionally further substituted by 1 to 5 (preferably 1 to 3) halogen atoms (e.g., fluorine), or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a $C_{1-6}$ alkyl group (e.g., methyl), (iii) a $C_{2-6}$ alkenyl group (e.g., ethenyl), (iv) a $C_{2-6}$ alkynyl group (e.g., ethynyl) optionally substituted by a tri-$C_{1-6}$ alkylsilyl group (e.g., trimethylsilyl), (v) a $C_{1-6}$ alkoxy group (e.g., methoxy) and (vi) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl), particularly preferably, a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring), each of which is optionally further substituted by 1 to 5 (preferably 1 to 3) substituents selected from (i) a halogen atom (e.g., chlorine), (ii) a cyano group, (iii) a $C_{1-6}$ alkyl group (e.g., methyl), (iv) a $C_{1-6}$ alkoxy group (e.g., methoxy) and (v) a 5- to 14-membered aromatic heterocyclic group (e.g., pyrazolyl) optionally substituted by 1 to 3 $C_{1-6}$ alkyl groups (e.g., methyl).

In another embodiment of the present invention, ring A is preferably an optionally further substituted 6-membered aromatic ring (e.g., benzene ring, pyridine ring), more preferably, a 6-membered aromatic ring (e.g., benzene ring, pyridine ring) optionally substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl), further preferably, a 6-membered aromatic ring (e.g., benzene ring, pyridine ring) optionally substituted by 1 to 5 (preferably 1 to 3) substituents selected from (i) a halogen atom (e.g., chlorine), (ii) a cyano group, (iii) a $C_{1-6}$ alkyl group (e.g., methyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

In still another embodiment of the present invention, ring A is preferably not a 2,4-dioxothiazolidine ring.

Preferable embodiments of compound (I) include the following compounds.

[Compound I-1]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl) or a $C_{1-6}$ alkoxy group (e.g., methoxy); or the partial structure:

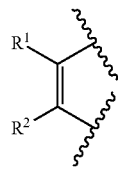

is

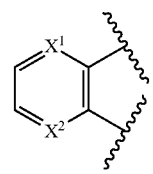

(wherein $X^1$ and $X^2$ are each CH);

$R^3$ is a hydrogen atom, an optionally substituted $C_{1-6}$ alkyl group (e.g., methyl), an optionally substituted $C_{3-10}$ cycloalkyl group (e.g., cyclopentyl, cyclohexyl), an optionally substituted $C_{6-14}$ aryl group (e.g., phenyl) or an optionally substituted 3- to 14-membered non-aromatic heterocyclic group (e.g., tetrahydropyranyl); and ring A is a $C_{6-14}$ aromatic hydrocarbon ring (e.g., benzene ring), a 3- to 14-membered non-aromatic heterocycle (e.g., pyrrolidine ring, piperidine ring, morpholine ring, thiomorpholine ring) or a 5- to 14-membered aromatic heterocycle (e.g., pyridine ring), each of which is optionally further substituted.

[Compound I-1A]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); or the partial structure:

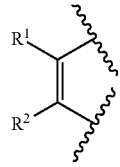

is

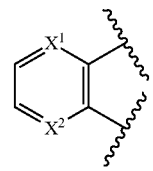

(wherein $X^1$ and $X^2$ are each CH);

$R^3$ is a hydrogen atom, an optionally substituted $C_{1-6}$ alkyl group (e.g., methyl, isobutyl), an optionally substituted $C_{3-10}$ cycloalkyl group (e.g., cyclopentyl, cyclohexyl), an optionally substituted $C_{6-14}$ aryl group (e.g., phenyl), or an optionally substituted 3- to 14-membered non-aromatic heterocyclic group (e.g., tetrahydropyranyl); and ring A is a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted.

[Compound I-1A-1]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent); or the partial structure:

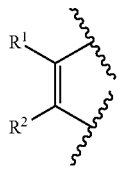

is

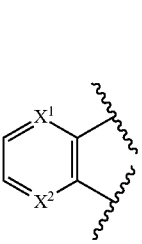

(wherein $X^1$ and $X^2$ are each CH);

$R^3$ is a hydrogen atom, an optionally substituted $C_{1-6}$ alkyl group (e.g., methyl, isobutyl), an optionally substituted $C_{3-10}$ cycloalkyl group (e.g., cyclopentyl, cyclohexyl), an optionally substituted $C_{6-14}$ aryl group (e.g., phenyl), or an optionally substituted 3- to 14-membered non-aromatic heterocyclic group (e.g., tetrahydropyranyl); and ring A is a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted.

[Compound I-1A-2]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

$R^3$ is an optionally substituted $C_{1-6}$ alkyl group (e.g., methyl, isobutyl), an optionally substituted $C_{3-10}$ cycloalkyl group (e.g., cyclopentyl, cyclohexyl), an optionally substituted $C_{6-14}$ aryl group (e.g., phenyl), or an optionally substituted 3- to 14-membered non-aromatic heterocyclic group (e.g., tetrahydropyranyl); and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring, indazole ring, pyrazolopyridine ring), each of which is optionally further substituted.

[Compound I-1A-3]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent);

$R^3$ is an optionally substituted $C_{1-6}$ alkyl group (e.g., methyl, isobutyl), an optionally substituted $C_{3-10}$ cycloalkyl group (e.g., cyclopentyl, cyclohexyl), an optionally substituted $C_{6-14}$ aryl group (e.g., phenyl), or an optionally substituted 3- to 14-membered non-aromatic heterocyclic group (e.g., tetrahydropyranyl); and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring, indazole ring, pyrazolopyridine ring), each of which is optionally further substituted.

[Compound I-1A-4]

Compound (I) wherein the partial structure:

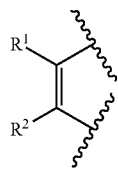

is

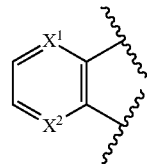

(wherein $X^1$ and $X^2$ are each CH);

$R^3$ is a hydrogen atom, an optionally substituted $C_{1-6}$ alkyl group (e.g., methyl), an optionally substituted $C_{3-10}$ cycloalkyl group (e.g., cyclopentyl, cyclohexyl), or an optionally substituted 3- to 14-membered non-aromatic heterocyclic group (e.g., tetrahydropyranyl); and ring A is a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring), each of which is optionally further substituted.

[Compound I-2]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl) or a $C_{1-6}$ alkoxy group (e.g., methoxy); or the partial structure:

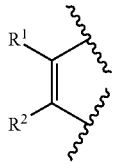

is

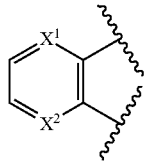

(wherein $X^1$ and $X^2$ are each CH);

$R^3$ is (1) a hydrogen atom, (2) a $C_{1-6}$ alkyl group (e.g., methyl) optionally substituted by 1 to 3 substituents selected from a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine), or (5) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., pyrrolidine ring, piperidine ring, morpholine ring, thiomorpholine ring) or a 5- to 14-membered aromatic heterocycle (e.g., pyridine ring), each of which is optionally further substituted by 1 to 5 (preferably 1 to 3) substituents selected from a halogen atom (e.g., fluorine, chlorine), a cyano group, an oxo group, a $C_{1-6}$ alkyl group (e.g., methyl, ethyl), a $C_{2-6}$ alkenyl group (e.g., ethenyl), a $C_{1-6}$ alkoxy group (e.g., methoxy) and a 5- to 14-membered aromatic heterocyclic group (e.g., pyrazolyl, imidazolyl, triazolyl) which is optionally substituted (preferably, by 1 to 3 substituents selected from a $C_{1-6}$ alkyl group (e.g., methyl)).

[Compound I-2A]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); or the partial structure:

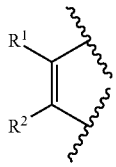

is

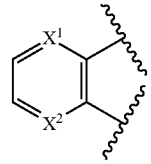

(wherein $X^1$ and $X^2$ are each CH);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., pyrrolidine ring, piperidine ring, morpholine ring, thiomorpholine ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) an oxo group, (iv) a $C_{1-6}$ alkyl group (e.g., methyl, ethyl), (v) a $C_{2-6}$ alkenyl group (e.g., ethenyl), (vi) a $C_{2-6}$ alkynyl group (e.g., ethynyl) optionally substituted by a tri-$C_{1-6}$ alkylsilyl group (e.g., trimethylsilyl), (vii) a $C_{1-6}$ alkoxy group (e.g., methoxy) and (viii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2B]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); or the partial structure:

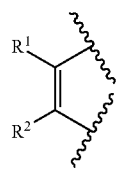

is

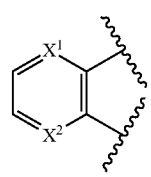

(wherein $X^1$ and $X^2$ are each CH);

R³ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) an oxo group, (iv) a $C_{1-6}$ alkyl group (e.g., methyl, ethyl) optionally substituted by 1 to 3 halogen atoms (e.g., fluorine), (v) a $C_{2-6}$ alkenyl group (e.g., ethenyl), (vi) a $C_{2-6}$ alkynyl group (e.g., ethynyl) optionally substituted by a tri-$C_{1-6}$ alkylsilyl group (e.g., trimethylsilyl), (vii) a $C_{1-6}$ alkoxy group (e.g., methoxy), (viii) a $C_{1-6}$ alkoxy-carbonyl group (e.g., methoxycarbonyl) and (ix) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2B-1]

Compound (I) wherein

R¹ is a hydrogen atom, a halogen atom (e.g., fluorine, chlorine) or a $C_{1-6}$ alkyl group (e.g., methyl);

R² is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both R¹ and R² are not hydrogen atoms at the same time (at least one of R¹ and R² is a substituent); or the partial structure:

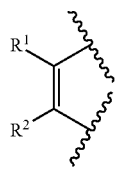

is

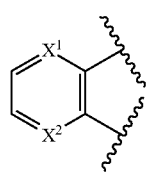

(wherein X¹ and X² are each CH);

R³ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) an oxo group, (iv) a $C_{1-6}$ alkyl group (e.g., methyl, ethyl) optionally substituted by 1 to 3 halogen atoms (e.g., fluorine), (v) a $C_{2-6}$ alkenyl group (e.g., ethenyl), (vi) a $C_{2-6}$ alkynyl group (e.g., ethynyl) optionally substituted by a tri-$C_{1-6}$ alkylsilyl group (e.g., trimethylsilyl), (vii) a $C_{1-6}$ alkoxy group (e.g., methoxy), (viii) a $C_{1-6}$ alkoxy-carbonyl group (e.g., methoxycarbonyl) and (ix) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2B-2]

Compound (I) wherein

R¹ is a hydrogen atom, a halogen atom (e.g., fluorine, chlorine) or a $C_{1-6}$ alkyl group (e.g., methyl);

R² is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

R³ is (1) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopentyl, cyclohexyl) optionally substituted by 1 to 3 hydroxy groups, (3) a $C_{6-14}$ aryl group (e.g., phenyl) optionally substituted by 1 to 3 halogen atoms (e.g., fluorine) or (4) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) a $C_{1-6}$ alkyl group (e.g., methyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2B-3]

Compound (I) wherein

R¹ is a hydrogen atom, a halogen atom (e.g., fluorine, chlorine) or a $C_{1-6}$ alkyl group (e.g., methyl);

R² is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

provided that both R¹ and R² are not hydrogen atoms at the same time (at least one of R¹ and R² is a substituent);

R³ is (1) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopentyl, cyclohexyl) optionally substituted by 1 to 3 hydroxy groups, (3) a $C_{6-14}$ aryl group (e.g., phenyl) optionally substituted by 1 to 3 halogen atoms (e.g., fluorine) or (4) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) a $C_{1-6}$ alkyl group (e.g., methyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2B-4]
Compound (I) wherein
the partial structure:

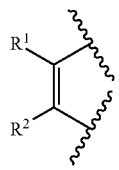

is

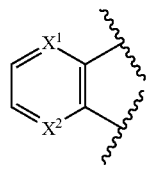

(wherein X¹ and X² are each CH);

R³ is (1) a hydrogen atom, (2) a $C_{1-6}$ alkyl group (e.g., methyl) optionally substituted by one to three, 3- to 14-membered non-aromatic heterocyclic groups (e.g., tetrahydrofuranyl), (3) a $C_{3-10}$ cycloalkyl group (e.g., cyclopentyl, cyclohexyl) optionally substituted by 1 to 3 hydroxy groups, or (4) a 3- to 14-membered non-aromatic heterocyclic group (e.g., tetrahydropyranyl) optionally substituted by 1 to 3 hydroxy groups; and ring A is a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring), each of which is optionally further substituted by 1 to 5 (preferably 1 to 3) substituents selected from (i) a halogen atom (e.g., fluorine, chlorine), (ii) a cyano group, (iii) an oxo group, (iv) a $C_{1-6}$ alkyl group (e.g., methyl, ethyl) optionally substituted by 1 to 3 halogen atoms (e.g., fluorine), (v) a $C_{2-6}$ alkenyl group (e.g., ethenyl), (vi) a $C_{1-6}$ alkoxy group (e.g., methoxy), (vii) a $C_{1-6}$ alkoxycarbonyl group (e.g., methoxycarbonyl) and (viii) a 5- to 14-membered aromatic heterocyclic group (e.g., pyrazolyl) optionally substituted by 1 to 3 $C_{1-6}$ alkyl groups (e.g., methyl).

[Compound I-2C]
Compound (I) wherein
R¹ is a hydrogen atom, a halogen atom (e.g., fluorine, chlorine) or a $C_{1-6}$ alkyl group (e.g., methyl);
R² is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); or
the partial structure:

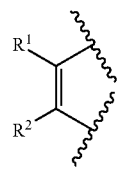

is

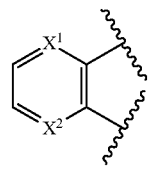

(wherein X¹ and X² are each CH);

R³ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a 6-membered aromatic ring (e.g., benzene ring, pyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2C-1]
Compound (I) wherein
R¹ is a hydrogen atom, a halogen atom (e.g., fluorine, chlorine) or a $C_{1-6}$ alkyl group (e.g., methyl);
R² is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent); or the partial structure:

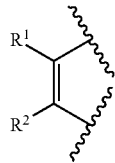

is

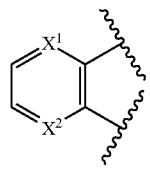

(wherein $X^1$ and $X^2$ are each CH);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a 6-membered aromatic ring (e.g., benzene ring, pyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl)

[Compound I-2C-2]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

$R^3$ is (1) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopentyl, cyclohexyl) optionally substituted by 1 to 3 hydroxy groups, (3) a $C_{6-14}$ aryl group (e.g., phenyl) optionally substituted by 1 to 3 halogen atoms (e.g., fluorine) or (4) a 3- to 14-membered non-aromatic heterocyclic group (e.g., tetrahydropyranyl) optionally substituted by 1 to 3 hydroxy groups; and ring A is a 6-membered aromatic ring (e.g., benzene ring, pyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2C-3]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent);

$R^3$ is (1) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopentyl, cyclohexyl) optionally substituted by 1 to 3 hydroxy groups, (3) a $C_{6-14}$ aryl group (e.g., phenyl) optionally substituted by 1 to 3 halogen atoms (e.g., fluorine) or (4) a 3- to 14-membered non-aromatic heterocyclic group (e.g., tetrahydropyranyl) optionally substituted by 1 to 3 hydroxy groups; and ring A is a 6-membered aromatic ring (e.g., benzene ring, pyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-2C-4]

Compound (I) wherein the partial structure:

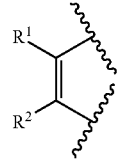

is

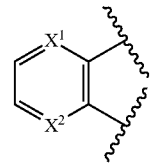

(wherein $X^1$ and $X^2$ are each CH);

$R^3$ is (1) a hydrogen atom, (2) a $C_{1-6}$ alkyl group (e.g., methyl) optionally substituted by one to three, 3- to 14-membered non-aromatic heterocyclic groups (e.g., tetrahydrofuranyl), (3) a $C_{3-10}$ cycloalkyl group (e.g., cyclopentyl, cyclohexyl) optionally substituted by 1 to 3 hydroxy groups or (4) a 3- to 14-membered non-aromatic heterocyclic group (e.g., tetrahydropyranyl) optionally substituted by 1 to 3 hydroxy groups; and ring A is a 6-membered aromatic ring (e.g., pyridine ring) optionally further substituted by 1 to 5 (preferably 1 to 3) substituents selected from (i) a halogen atom (e.g., chlorine), (ii) a $C_{1-6}$ alkyl group (e.g., methyl, ethyl), (iii) a $C_{2-6}$ alkenyl group (e.g., ethenyl), (iv) a $C_{1-6}$ alkoxy group (e.g., methoxy) and (v) a 5- to 14-membered aromatic heterocyclic group (e.g., pyrazolyl) optionally substituted by 1 to 3 $C_{1-6}$ alkyl groups (e.g., methyl).

[Compound I-3]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl) or a $C_{1-6}$ alkoxy group (e.g., methoxy); or the partial structure:

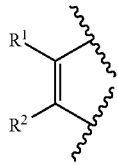

is

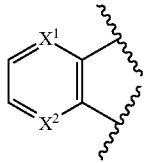

(wherein $X^1$ and $X^2$ are each CH);

$R^3$ is (1) a hydrogen atom, (2) a $C_{1-6}$ alkyl group (e.g., methyl) optionally substituted by 1 to 3 substituents selected from a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl) optionally substituted by 1 to 3 $C_{1-6}$ alkyl groups (e.g., methyl), (2) a 3- to 14-membered non-aromatic heterocycle (e.g., pyrrolidine ring, piperidine ring, morpholine ring, thiomorpholine ring) optionally further substituted by 1 to 5 (preferably 1 to 3) substituents selected from a halogen atom (e.g., fluorine), a cyano group and an oxo group, or (3) a 5- to 14-membered aromatic heterocycle (e.g., pyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{1-6}$ alkoxy group (e.g., methoxy) and (vi) a 5- to 14-membered aromatic heterocyclic group (e.g., pyrazolyl, imidazolyl, triazolyl) optionally substituted by 1 to 3 $C_{1-6}$ alkyl groups (e.g., methyl).

[Compound I-3A]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); or the partial structure:

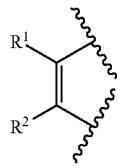

is

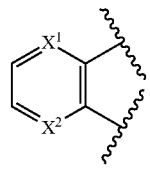

(wherein $X^1$ and $X^2$ are each CH);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., pyrrolidine ring, piperidine ring, morpholine ring, thiomorpholine ring) optionally further substituted by 1 to 5 (preferably 1 to 3) substituents selected from (i) a halogen atom (e.g., fluorine), (ii) a cyano group and (iii) an oxo group, or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl).

[Compound I-3B]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); or the partial structure:

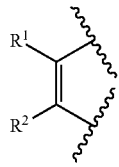

is

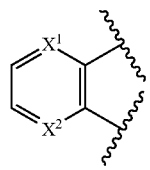

(wherein $X^1$ and $X^2$ are each CH);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., azetidine ring, pyrrolidine ring, piperidine ring, piperazine ring, morpholine ring, thiomorpholine ring, oxaazaspirononane ring) optionally further substituted by 1 to 5 (preferably 1 to 3) substituents selected from (i) a halogen atom (e.g., fluorine), (ii) a cyano group, (iii) an oxo group, (iv) a $C_{1-6}$ alkyl group (e.g., methyl) optionally substituted by 1 to 3 halogen atoms (e.g., fluorine), (v) a $C_{1-6}$ alkoxy group (e.g., methoxy) and (vi) a $C_{1-6}$ alkoxy-carbonyl group (e.g., methoxycarbonyl), or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl).

[Compound I-3B-1]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent); or the partial structure:

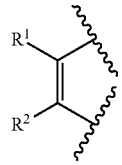

is

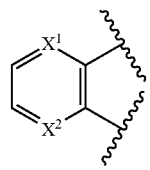

(wherein $X^1$ and $X^2$ are each CH);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., azetidine ring, pyrrolidine ring, piperidine ring, piperazine ring, morpholine ring, thiomorpholine ring, oxaazaspirononane ring) optionally further substituted by 1 to 5 (preferably 1 to 3) substituents selected from (i) a halogen atom (e.g., fluorine), (ii) a cyano group, (iii) an oxo group, (iv) a $C_{1-6}$ alkyl group (e.g., methyl) optionally substituted by 1 to 3 halogen atoms (e.g., fluorine), (v) a $C_{1-6}$ alkoxy group (e.g., methoxy) and (vi) a $C_{1-6}$ alkoxy-carbonyl group (e.g., methoxycarbonyl), or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl).

[Compound I-3B-2]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

$R^3$ is (1) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopentyl, cyclohexyl) optionally substituted by 1 to 3 hydroxy groups, (3) a $C_{6-14}$ aryl group (e.g., phenyl) optionally substituted by 1 to 3 halogen atoms (e.g., fluorine) or (4) a 3- to 14-membered non-aromatic heterocyclic group (e.g., tetrahydropyranyl) optionally substituted by 1 to 3 hydroxy groups; and ring A is (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., piperidine ring) optionally further substituted by 1 to 5 (preferably 1 to 3) halogen atoms (e.g., fluorine), or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a $C_{1-6}$ alkyl group (e.g., methyl), (iii) a $C_{2-6}$ alkenyl group (e.g., ethenyl), (iv) a $C_{2-6}$ alkynyl group (e.g., ethynyl) optionally substituted by a tri-$C_{1-6}$ alkylsilyl group (e.g., trimethylsilyl), (v) a $C_{1-6}$ alkoxy group (e.g., methoxy) and (vi) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl).

[Compound I-3B-3]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

provided that both $R^1$ and $R^2$ are not hydrogen atoms at the same time (at least one of $R^1$ and $R^2$ is a substituent);

$R^3$ is (1) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopentyl, cyclohexyl) optionally substituted by 1 to 3 hydroxy groups, (3) a $C_{6-14}$ aryl group (e.g., phenyl) optionally substituted by 1 to 3 halogen atoms (e.g., fluorine) or (4) a 3- to 14-membered non-aromatic heterocyclic group (e.g., tetrahydropyranyl) optionally substituted by 1 to 3 hydroxy groups; and ring A is (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., piperidine ring) optionally further substituted by 1 to 5 (preferably 1 to 3) halogen atoms (e.g., fluorine), or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a $C_{1-6}$ alkyl group (e.g., methyl), (iii) a $C_{2-6}$ alkenyl group (e.g., ethenyl), (iv) a $C_{2-6}$ alkynyl group (e.g., ethynyl) optionally substituted by a tri-$C_{1-6}$ alkylsilyl group (e.g., trimethylsilyl), (v) a $C_{1-6}$ alkoxy group (e.g., methoxy) and (vi) a 5- to 14-membered aromatic heterocyclic group (e.g., pyrazolyl, imidazolyl, pyridyl) optionally substituted by 1 to 3 substituents selected from a halogen atom (e.g., fluorine) and a $C_{1-6}$ alkyl group (e.g., methyl, ethyl).

[Compound I-3B-4]

Compound (I) wherein the partial structure:

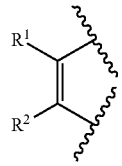

is

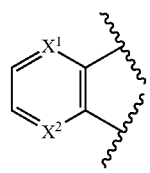

(wherein $X^1$ and $X^2$ are each CH);

$R^3$ is (1) a hydrogen atom, (2) a $C_{1-6}$ alkyl group (e.g., methyl) optionally substituted by one to three, 3- to 14-membered non-aromatic heterocyclic groups (e.g., tetrahydrofuranyl), (3) a $C_{3-10}$ cycloalkyl group (e.g., cyclopentyl, cyclohexyl) optionally substituted by 1 to 3 hydroxy groups, or (4) a 3- to 14-membered non-aromatic heterocyclic group (e.g., tetrahydropyranyl) optionally substituted by 1 to 3 hydroxy groups; and ring A is (1) a 3- to 14-membered non-aromatic heterocycle (e.g., azetidine ring, pyrrolidine ring, piperidine ring, piperazine ring, morpholine ring, thiomorpholine ring, oxaazaspirononane ring) optionally further substituted by 1 to 5 (preferably 1 to 3) substituents selected from (i) a halogen atom (e.g., fluorine), (ii) a cyano group, (iii) an oxo group, (iv) a $C_{1-6}$ alkyl group (e.g., methyl) optionally substituted by 1 to 3 halogen atoms (e.g., fluorine), (v) a $C_{1-6}$ alkoxy group (e.g., methoxy) and (vi) a $C_{1-6}$ alkoxy-carbonyl group (e.g., methoxycarbonyl), or (2) a 5- to 14-membered aromatic heterocycle (e.g., pyridine ring) optionally further substituted by 1 to 5 (preferably 1 to 3) substituents selected from (i) a halogen atom (e.g., chlorine), (ii) a $C_{1-6}$ alkyl group (e.g., methyl, ethyl), (iii) a $C_{2-6}$ alkenyl group (e.g., ethenyl), (iv) a $C_{1-6}$ alkoxy group (e.g., methoxy) and (v) a 5- to 14-membered aromatic heterocyclic group (e.g., pyrazolyl) optionally substituted by 1 to 3 $C_{1-6}$ alkyl groups (e.g., methyl).

[Compound I-4]

Compound (I) wherein $R^1$ is a hydrogen atom, a halogen atom (e.g., fluorine, chlorine) or a $C_{1-6}$ alkyl group (e.g., methyl);

$R^2$ is a $C_{1-6}$ alkyl group (e.g., methyl) or a $C_{1-6}$ alkoxy group (e.g., methoxy); or the partial structure:

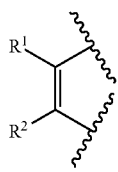

is

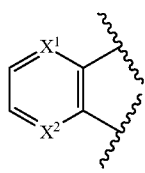

(wherein $X^1$ and $X^2$ are each CH);

$R^3$ is a $C_{3-10}$ cycloalkyl group (e.g., cyclopentyl, cyclohexyl) optionally substituted by 1 to 3 hydroxy groups or a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring), each of which is optionally further substituted by 1 to 5 (preferably 1 to 3) substituents selected from a halogen atom (e.g., fluorine, chlorine), a cyano group, a $C_{1-6}$ alkyl group (e.g., methyl), a $C_{1-6}$ alkoxy group (e.g., methoxy) and a 5- to 14-membered aromatic heterocyclic group (e.g., pyrazolyl) which is optionally substituted (preferably, by 1 to 3 substituents selected from a $C_{1-6}$ alkyl group (e.g., methyl)).

[Compound I-4A]

Compound (I) wherein $R^1$ is a hydrogen atom, a halogen atom (e.g., fluorine, chlorine) or a $C_{1-6}$ alkyl group (e.g., methyl);

$R^2$ is a $C_{1-6}$ alkyl group (e.g., methyl, ethyl), a $C_{2-6}$ alkenyl group (e.g., ethenyl) or a $C_{1-6}$ alkoxy group (e.g., methoxy); or the partial structure:

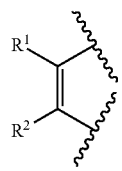

is

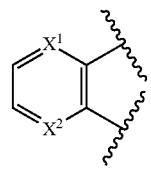

(wherein $X^1$ and $X^2$ are each CH);

$R^3$ is a $C_{3-10}$ cycloalkyl group (e.g., cyclopentyl, cyclohexyl) optionally substituted by 1 to 3 hydroxy groups or a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring, indazole ring, pyrazolopyridine ring), each of which is optionally further substituted by 1 to 5 (preferably 1 to 3) substituents selected from a halogen atom (e.g., fluorine, chlorine), a cyano group, a $C_{1-6}$ alkyl group (e.g., methyl), a $C_{2-6}$ alkenyl group (e.g., ethenyl), a $C_{1-6}$ alkoxy group (e.g., methoxy) and a 5- to 14-membered aromatic heterocyclic group (e.g., pyrazolyl) which is optionally substituted (preferably, by 1 to 3 substituents selected from a $C_{1-6}$ alkyl group (e.g., methyl)).

[Compound I-4B]

Compound (I) wherein $R^1$ is a hydrogen atom, a halogen atom (e.g., fluorine, chlorine) or a $C_{1-6}$ alkyl group (e.g., methyl);

$R^2$ is a $C_{1-6}$ alkyl group (e.g., methyl, ethyl), a $C_{2-6}$ alkenyl group (e.g., ethenyl) or a $C_{1-6}$ alkoxy group (e.g., methoxy); or the partial structure:

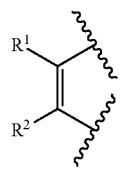

is

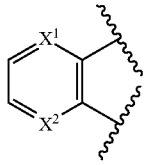

(wherein X¹ and X² are each CH);

R³ is (1) a $C_{3-10}$ cycloalkyl group (e.g., cyclopentyl, cyclohexyl) optionally substituted by 1 to 3 hydroxy groups or (2) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring), each of which is optionally further substituted by 1 to 5 (preferably 1 to 3) substituents selected from (i) a halogen atom (e.g., fluorine, chlorine), (ii) a cyano group, (iii) a $C_{1-6}$ alkyl group (e.g., methyl), (iv) a $C_{1-6}$ alkoxy group (e.g., methoxy) and (v) a 5- to 14-membered aromatic heterocyclic group (e.g., pyrazolyl) optionally substituted by 1 to 3 $C_{1-6}$ alkyl groups (e.g., methyl).

[Compound I-4B-1]

Compound (I) wherein

R¹ is a hydrogen atom, a halogen atom (e.g., fluorine, chlorine) or a $C_{1-6}$ alkyl group (e.g., methyl);

R² is a $C_{1-6}$ alkyl group (e.g., methyl, ethyl), a $C_{2-6}$ alkenyl group (e.g., ethenyl) or a $C_{1-6}$ alkoxy group (e.g., methoxy);

R³ is (1) a $C_{3-10}$ cycloalkyl group (e.g., cyclopentyl, cyclohexyl) optionally substituted by 1 to 3 hydroxy groups or (2) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring), each of which is optionally further substituted by 1 to 5 (preferably 1 to 3) substituents selected from (i) a halogen atom (e.g., chlorine), (ii) a cyano group, (iii) a $C_{1-6}$ alkyl group (e.g., methyl), (iv) a $C_{1-6}$ alkoxy group (e.g., methoxy) and (v) a 5- to 14-membered aromatic heterocyclic group (e.g., pyrazolyl) optionally substituted by 1 to 3 $C_{1-6}$ alkyl groups (e.g., methyl).

[Compound I-4B-2]

Compound (I) wherein the partial structure:

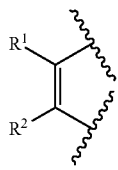

is

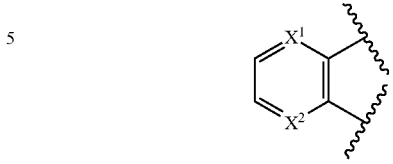

(wherein X¹ and X² are each CH);

R³ is (1) a $C_{3-10}$ cycloalkyl group (e.g., cyclopentyl) optionally substituted by 1 to 3 hydroxy groups or (2) a 3- to 14-membered non-aromatic heterocyclic group (e.g., tetrahydropyranyl) optionally substituted by 1 to 3 hydroxy groups; and ring A is a 3- to 14-membered non-aromatic heterocycle (e.g., piperidine ring) or a 5- to 14-membered aromatic heterocycle (e.g., pyridine ring), each of which is optionally further substituted by 1 to 5 (preferably 1 to 3) substituents selected from (i) a halogen atom (e.g., fluorine, chlorine) and (ii) a $C_{1-6}$ alkyl group (e.g., methyl).

[Compound I-5]

Compound (I) wherein

R¹ is a hydrogen atom, a halogen atom (e.g., fluorine, chlorine) or a $C_{1-6}$ alkyl group (e.g., methyl);

R² is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); (preferably, both R¹ and R² are not hydrogen atoms at the same time (at least one of R¹ and R² is a substituent));

R³ is a hydrogen atom, an optionally substituted $C_{1-6}$ alkyl group (e.g., methyl, isobutyl), an optionally substituted $C_{3-10}$ cycloalkyl group (e.g., cyclopentyl, cyclohexyl), an optionally substituted $C_{6-14}$ aryl group (e.g., phenyl), or an optionally substituted 3- to 14-membered non-aromatic heterocyclic group (e.g., tetrahydropyranyl); and ring A is a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted.

[Compound I-5A]

Compound (I) wherein

R¹ is a hydrogen atom, a halogen atom (e.g., fluorine, chlorine) or a $C_{1-6}$ alkyl group (e.g., methyl);

R² is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

R³ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) an oxo group, (iv) a $C_{1-6}$ alkyl group (e.g., methyl, ethyl) optionally substituted by 1 to 3 halogen atoms (e.g., fluorine), (v) a $C_{2-6}$ alkenyl group (e.g., ethenyl), (vi) a $C_{2-6}$ alkynyl group (e.g., ethynyl) optionally substituted by a tri-$C_{1-6}$ alkylsilyl group (e.g., trimethylsilyl), (vii) a $C_{1-6}$ alkoxy group (e.g., methoxy), (viii) a $C_{1-6}$ alkoxy-carbonyl group (e.g., methoxycarbonyl) and (ix) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-5B]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring), a 3- to 14-membered non-aromatic heterocycle (e.g., azetidine ring, pyrrolidine ring, piperidine ring, piperazine ring, morpholine ring, thiomorpholine ring, oxaazaspirononane ring) or a 5- to 14-membered aromatic heterocycle (e.g., pyridine ring, indazole ring, pyrazolopyridine ring), each of which is optionally further substituted by 1 to 5 (preferably 1 to 3) substituents selected from (i) a halogen atom (e.g., fluorine, chlorine), (ii) a cyano group, (iii) an oxo group, (iv) a $C_{1-6}$ alkyl group (e.g., methyl, ethyl) optionally substituted by 1 to 3 halogen atoms (e.g., fluorine), (v) a $C_{2-6}$ alkenyl group (e.g., ethenyl), (vi) a $C_{2-6}$ alkynyl group (e.g., ethynyl) optionally substituted by a tri-$C_{1-6}$ alkylsilyl group (e.g., trimethylsilyl), (vii) a $C_{1-6}$ alkoxy group (e.g., methoxy), (viii) a $C_{1-6}$ alkoxy-carbonyl group (e.g., methoxycarbonyl) and (ix) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-5C]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a 6-membered aromatic ring (e.g., benzene ring, pyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl).

[Compound I-5D]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is a 6-membered aromatic ring (e.g., benzene ring, pyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl, pyridazinyl) optionally substituted by 1 to 3 substituents selected from a halogen atom (e.g., fluorine) and a $C_{1-6}$ alkyl group (e.g., methyl, ethyl)

[Compound I-5E]

Compound (I) wherein $R^1$ is a hydrogen atom, a halogen atom (e.g., fluorine, chlorine) or a $C_{1-6}$ alkyl group (e.g., methyl);

$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy);

$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and ring A is (1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl), (2) a 3- to 14-membered non-aromatic heterocycle (e.g., azetidine ring, pyrrolidine ring, piperidine ring, piperazine ring, morpholine ring, thiomorpholine ring, oxaazaspirononane ring) optionally further substituted by 1 to 5 (preferably 1 to 3) substituents selected from (i) a halogen atom (e.g., fluorine), (ii) a cyano group, (iii) an oxo group, (iv) a $C_{1-6}$ alkyl group (e.g., methyl) optionally substituted by 1 to 3 halogen atoms (e.g., fluorine), (v) a $C_{1-6}$ alkoxy group (e.g., methoxy) and (vi) a $C_{1-6}$ alkoxy-carbonyl group (e.g., methoxycarbonyl), or (3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl).

[Compound I-5F]
Compound (I) wherein
$R^1$ is a hydrogen atom, a halogen atom (e.g., fluorine, chlorine) or a $C_{1-6}$ alkyl group (e.g., methyl);
$R^2$ is a hydrogen atom, a halogen atom (e.g., chlorine), a $C_{1-6}$ alkyl group (e.g., methyl, ethyl), a $C_{2-6}$ alkenyl group (e.g., ethenyl) or a $C_{1-6}$ alkoxy group (e.g., methoxy); provided that both $R^1$ and $R^2$ are not hydrogen atoms at the same time (at least one of $R^1$ and $R^2$ is a substituent);
$R^3$ is (1) a hydrogen atom, (2) a $C_{1-6}$ alkyl group (e.g., methyl, isobutyl) optionally substituted by 1 to 3 substituents selected from a hydroxy group and a 3- to 14-membered non-aromatic heterocyclic group (e.g., tetrahydrofuranyl), (3) a $C_{3-10}$ cycloalkyl group (e.g., cyclopentyl, cyclohexyl) optionally substituted by 1 to 3 hydroxy groups, (4) a $C_{6-14}$ aryl group (e.g., phenyl) optionally substituted by 1 to 3 halogen atoms (e.g., fluorine) or (5) a 3- to 14-membered non-aromatic heterocyclic group (e.g., tetrahydropyranyl) optionally substituted by 1 to 3 hydroxy groups; and
ring A is
(1) a $C_{6-14}$ aromatic hydrocarbon ring (e.g., benzene ring) optionally further substituted by 1 to 5 (preferably 1 to 3) substituents selected from (i) a cyano group, (ii) a $C_{1-6}$ alkoxy group (e.g., methoxy) and (iii) a 5- to 14-membered aromatic heterocyclic group (e.g., pyrazolyl, triazolyl, pyridazinyl) optionally substituted by 1 to 3 $C_{1-6}$ alkyl groups (e.g., methyl),
(2) a 3- to 14-membered non-aromatic heterocycle (e.g., azetidine ring, pyrrolidine ring, piperidine ring, piperazine ring, morpholine ring, thiomorpholine ring, oxaazaspirononane ring) optionally further substituted by 1 to 5 (preferably 1 to 3) substituents selected from (i) a halogen atom (e.g., fluorine), (ii) a cyano group, (iii) an oxo group, (iv) a $C_{1-6}$ alkyl group (e.g., methyl) optionally substituted by 1 to 3 halogen atoms (e.g., fluorine), (v) a $C_{1-6}$ alkoxy group (e.g., methoxy) and (vi) a $C_{1-6}$ alkoxy-carbonyl group (e.g., methoxycarbonyl), or
(3) a 5- to 14-membered aromatic heterocycle (e.g., pyridine ring, indazole ring, pyrazolopyridine ring) optionally further substituted by 1 to 5 (preferably 1 to 3) substituents selected from (i) a halogen atom (e.g., chlorine), (ii) a cyano group, (iii) a $C_{1-6}$ alkyl group (e.g., methyl, ethyl), (iv) a $C_{2-6}$ alkenyl group (e.g., ethenyl), (v) a $C_{2-6}$ alkynyl group (e.g., ethynyl) optionally substituted by a tri-$C_{1-6}$ alkylsilyl group (e.g., trimethylsilyl), (vi) a $C_{1-6}$ alkoxy group (e.g., methoxy) and (vii) a 5- to 14-membered aromatic heterocyclic group (e.g., pyrazolyl, imidazolyl, triazolyl, pyridyl) optionally substituted by 1 to 3 substituents selected from a halogen atom (e.g., fluorine) and a $C_{1-6}$ alkyl group (e.g., methyl, ethyl).

[Compound I-5G]
Compound (I) wherein
$R^1$ is a hydrogen atom, a halogen atom (e.g., fluorine, chlorine) or a $C_{1-6}$ alkyl group (e.g., methyl);
$R^2$ is a $C_{1-6}$ alkyl group (e.g., methyl, ethyl), a $C_{2-6}$ alkenyl group (e.g., ethenyl) or a $C_{1-6}$ alkoxy group (e.g., methoxy);
$R^3$ is (1) a $C_{3-10}$ cycloalkyl group (e.g., cyclopentyl, cyclohexyl) optionally substituted by 1 to 3 hydroxy groups or (2) a 3- to 14-membered non-aromatic heterocyclic group (e.g., tetrahydropyranyl) optionally substituted by 1 to 3 hydroxy groups; and
ring A is a $C_{6-14}$ aromatic hydrocarbon ring (e.g., benzene ring), a 3- to 14-membered non-aromatic heterocycle (e.g., piperidine ring) or a 5- to 14-membered aromatic heterocycle (e.g., pyridine ring), each of which is optionally further substituted by 1 to 5 (preferably 1 to 3) substituents selected from (i) a halogen atom (e.g., fluorine, chlorine), (ii) a cyano group, (iii) a $C_{1-6}$ alkyl group (e.g., methyl), (iv) a $C_{1-6}$ alkoxy group (e.g., methoxy) and (v) a 5- to 14-membered aromatic heterocyclic group (e.g., pyrazolyl) optionally substituted by 1 to 3 $C_{1-6}$ alkyl groups (e.g., methyl).

[Compound I-6]
Compound (I) wherein
$R^1$ is a halogen atom (e.g., fluorine) or a $C_{1-6}$ alkyl group (e.g., methyl);
$R^2$ is a $C_{1-6}$ alkyl group (e.g., methyl);
$R^3$ is a $C_{3-10}$ cycloalkyl group (e.g., cyclopentyl) optionally substituted by 1 to 3 hydroxy groups or a 3- to 14-membered non-aromatic heterocyclic group (e.g., tetrahydropyranyl) optionally substituted by 1 to 3 hydroxy groups; and
ring A is a $C_{6-14}$ aromatic hydrocarbon ring (e.g., benzene ring) or a 5- to 14-membered aromatic heterocycle (e.g., pyridine ring), each of which is optionally further substituted by 1 to 5 (preferably 1 to 3) substituents selected from a $C_{1-6}$ alkoxy group (e.g., methoxy) and a 5- to 14-membered aromatic heterocyclic group (e.g., pyrazolyl) which is optionally substituted (preferably, by 1 to 3 substituents selected from a $C_{1-6}$ alkyl group (e.g., methyl)).

[Compound I-6A]
Compound (I) wherein
$R^1$ is a hydrogen atom, a halogen atom (e.g., chlorine, fluorine) or a $C_{1-6}$ alkyl group (e.g., methyl);
$R^2$ is a $C_{1-6}$ alkyl group (e.g., methyl);
$R^3$ is (1) a $C_{3-10}$ cycloalkyl group (e.g., cyclopentyl, cyclohexyl) optionally substituted by 1 to 3 hydroxy groups or (2) a 3- to 14-membered non-aromatic heterocyclic group (e.g., tetrahydropyranyl) optionally substituted by 1 to 3 hydroxy groups; and
ring A is a $C_{6-14}$ aromatic hydrocarbon ring (e.g., benzene ring) or a 5- to 14-membered aromatic heterocycle (e.g., pyridine ring), each of which is optionally further substituted by 1 to 5 (preferably 1 to 3) substituents selected from (i) a halogen atom (e.g., chlorine), (ii) a $C_{1-6}$ alkyl group (e.g., methyl), (iii) a $C_{1-6}$ alkoxy group (e.g., methoxy) and (iv) a 5- to 14-membered aromatic heterocyclic group (e.g., pyrazolyl) optionally substituted by 1 to 3 $C_{1-6}$ alkyl groups (e.g., methyl).

[Compound I-6B]

Compound (I) wherein $R^1$ is a hydrogen atom or a halogen atom (e.g., fluorine, chlorine);

$R^2$ is a $C_{1-6}$ alkyl group (e.g., methyl);

$R^3$ is (1) a $C_{3-10}$ cycloalkyl group (e.g., cyclopentyl, cyclohexyl) optionally substituted by 1 to 3 hydroxy groups or (2) a 3- to 14-membered non-aromatic heterocyclic group (e.g., tetrahydropyranyl) optionally substituted by 1 to 3 hydroxy groups; and ring A is a $C_{6-14}$ aromatic hydrocarbon ring (e.g., benzene ring) or a 5- to 14-membered aromatic heterocycle (e.g., pyridine ring), each of which is optionally further substituted by 1 to 5 (preferably 1 to 3) substituents selected from (i) a halogen atom (e.g., chlorine), (ii) a $C_{1-6}$ alkyl group (e.g., methyl) and (iii) a 5- to 14-membered aromatic heterocyclic group (e.g., pyrazolyl) optionally substituted by 1 to 3 $C_{1-6}$ alkyl groups (e.g., methyl).

Preferable specific examples of the compound represented by the formula (I) include the compounds of Examples 1-82 and 84-142. Of those, 8-fluoro-3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one or a salt thereof;

8-chloro-6-((6-chloropyridin-3-yl)methyl)-3-((1S,2S)-2-hydroxycyclopentyl)-7-methyl-2,3-dihydro-4H-1,3-benzoxazin-4-one or a salt thereof;

3-(trans-2-hydroxycyclohexyl)-7-methyl-6-((6-methylpyridin-3-yl)methyl)-2,3-dihydro-4H-1,3-benzoxazin-4-one or a salt thereof; and 3-((3S,4S)-4-hydroxytetrahydro-2H-pyran-3-yl)-7-methyl-6-(4-(l-methyl-1H-pyrazol-3-yl)benzyl)-2,3-dihydro-4H-1,3-benzoxazin-4-one or a salt thereof are preferable.

When compound (I) is in a form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, preferable examples of the pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. Compound (I) may be a compound labeled or substituted with an isotope (e.g., $^2H$, $^3H$, $^{11}C$, $^{14}C$, $^{18}F$, $^{35}S$, $^{125}I$). A compound labeled with or substituted by an isotope may be able to be used, for example, as a tracer used for Positron Emission Tomography (PET) (PET tracer), and may be useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are all encompassed in compound (I) of the present invention.

The production methods of the compound of the present invention are explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the free form or the objective other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalents-1 equivalent, preferably 0.01 equivalents-0.2 equivalents, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane, heptane and the like;
amides: N,N-dimethylformamide, N,N-dimethylacetamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate, cesium carbonate, lithium hydroxide, potassium acetate and the like;
organic bases: triethylamine, diethylamine, N,N-diisopropylethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, 2,2,6,6-tetramethylpiperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & SonsInc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in EXAMPLES.

In each step, protection or deprotection reaction of functional groups is performed according to a method known per se, for example, the methods described in Wiley-Interscience, 2007, "Protective Groups in Organic Synthesis, 4th Ed." (Theodora W. Greene, Peter G. M. Wuts); Thieme, 2004, "Protecting Groups 3rd Ed." (P. J. Kocienski) and the like, or the methods described in the Examples.

Examples of the protecting group for hydroxy group of alcohol and the like and phenolic hydroxyl group include ether-type protecting groups such as methoxymethyl ether, benzyl ether, tert-butyldimethylsilyl ether, tetrahydropyranyl ether and the like; carboxylate-type protecting groups such as acetate, benzoate and the like; sulfonate-type protecting groups such as methanesulfonate and the like; carbonate-type protecting groups such as tert-butyl carbonate and the like; and the like.

Examples of the protecting group for carbonyl group of aldehyde include acetal-type protecting groups such as dimethyl acetal and the like; cyclic acetal-type protecting groups such as 1,3-dioxane and the like; and the like.

Examples of the protecting group for carbonyl group of ketone include ketal-type protecting groups such as dimethyl ketal and the like; cyclic ketal-type protecting groups such as 1,3-dioxane and the like; oxime-type protecting groups such as O-methyloxime and the like; hydrazone-type protecting groups such as N,N-dimethylhydrazone and the like; and the like.

Examples of the protecting group for carboxy group include ester-type protecting groups such as methyl ester and the like; amide-type protecting groups such as N,N-dimethylamide and the like; and the like.

Examples of the protecting group for thiol include ether-type protecting groups such as benzyl thioether and the like; ester-type protecting groups such as thioacetate, thiocarbonate, thiocarbamate and the like; and the like.

Examples of the protecting group for amino group, and aromatic heterocycle such as imidazole, pyrrole, indole and the like include carbamate-type protecting groups such as benzyl carbamate, tert-butyl carbamate and the like; amide-type protecting groups such as acetamide and the like; alkylamine-type protecting groups such as N-triphenylmethylamine and the like; sulfonamide-type protecting groups such as methanesulfonamide and the like; and the like.

Protecting groups can be removed by a method known per se, for example, methods using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), reduction methods and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an acid anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbanion, nucleophilic 1,4-addition reaction (Michael addition reaction) by a carbanion or nucleophilic substitution reaction by a carbanion is carried out in each step, examples of the base to be used for generation of the carbanion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate ester is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate ester (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as acid anhydrides, activated esters, sulfate esters and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; oxalyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium (II) acetate, tetrakis(triphenylphosphine)palladium (0), dichlorobis(triphenylphosphine)palladium (II), dichlorobis(triethylphosphine)palladium (II), tris(dibenzylideneacetone)dipalladium (0), 1,1'-bis(diphenylphosphino)ferrocene palladium (II) chloride, bis(tri-tert-butylphosphine)palladium (0) and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson's reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting heat, light, a radical initiator such as benzoyl peroxide, azobisisobutyronitrile and the like to the reaction system.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate ester, and then reacting the sulfonate ester with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride, N-phenylbis(trifluoromethanesulfonimide) and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When oxazinone ring formation reaction of salicylamide is carried out in each step, examples of the reagent to be used include formaldehyde, paraformaldehyde, 1,3,5-trioxane, dibromomethane, diiodomethane, chloroiodomethane and the like. Examples of the acid to be used include formic acid, p-toluenesulfonic acid, camphorsulfonic acid and the like, and examples of the base to be used include cesium carbonate and the like.

When ester-amide exchange reaction is carried out in each step, examples of the base to be used include triethylamine, N,N-diisopropylethylamine, 1,8-diazabicyclo[5.4.0]-7-undecene, sodium hydrogen carbonate and the like.

When halogenation reaction is carried out in each step, examples of the halogenating agent to be used include N-chlorosuccinimide (NCS), sulfuryl chloride and the like for chlorination, and N-bromosuccinimide (NBS), bromine and the like for bromination.

Compound (I) can be produced by the methods shown in the following schemes or a method analogous thereto or a method described in the Examples.

Compound (I) can be produced from compound (1) by the following method.

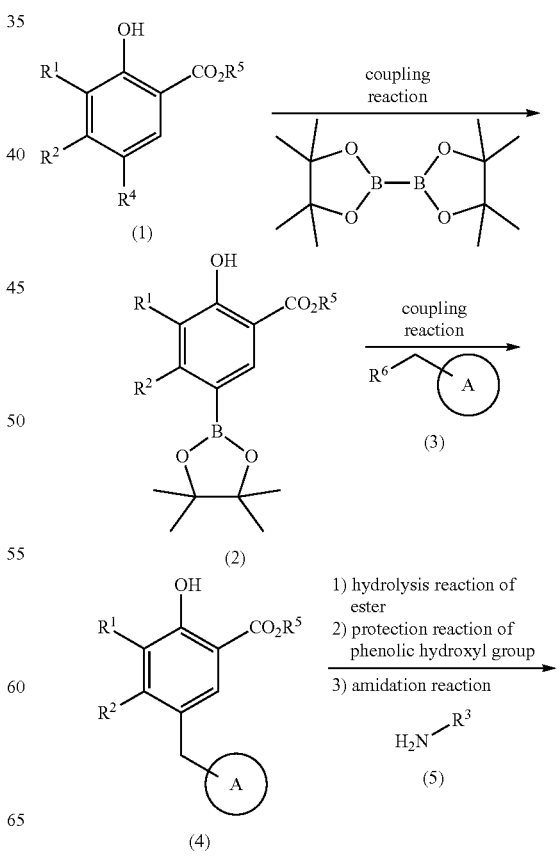

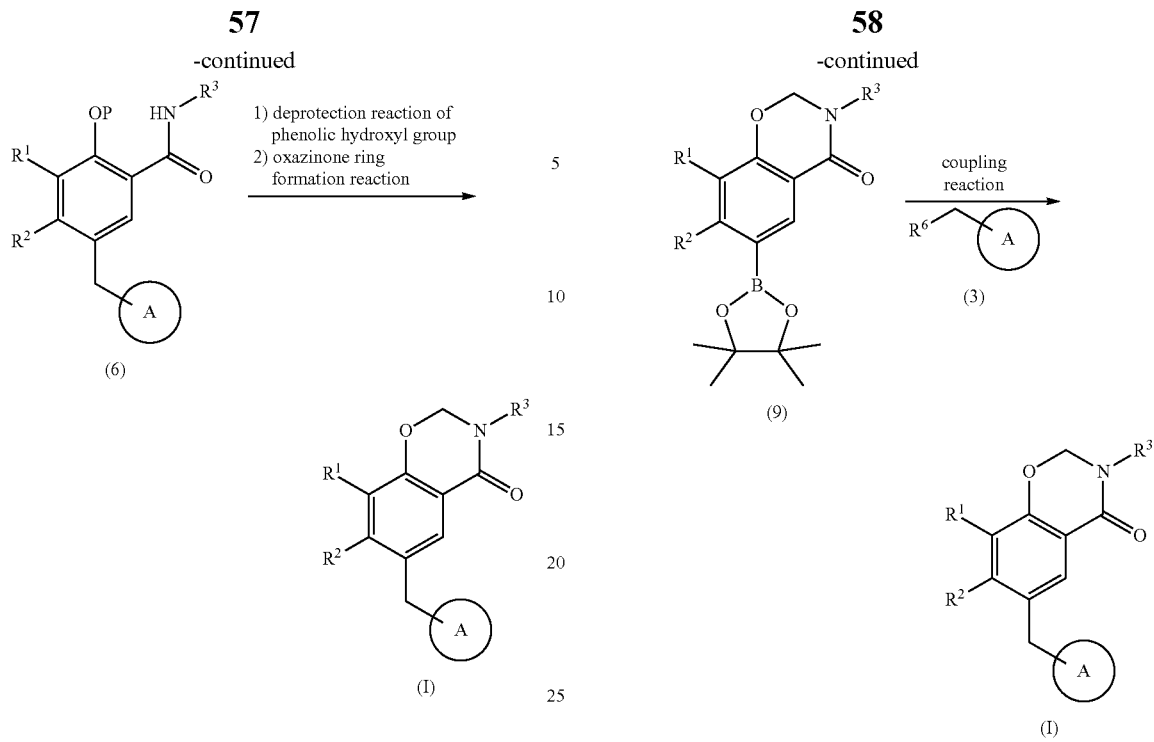
wherein $R^4$ and $R^6$ are halogen atoms, $R^5$ is a lower alkyl group, P is a protecting group such as a benzoyl group and the like, and ring A and $R^1$-$R^3$ are as defined above.
Compound (I) can also be produced from compound (1) by the following method.
wherein ring A, $R^1$-$R^6$ and P are as defined above.
Compound (I) can also be produced from compound (1) by the following method.
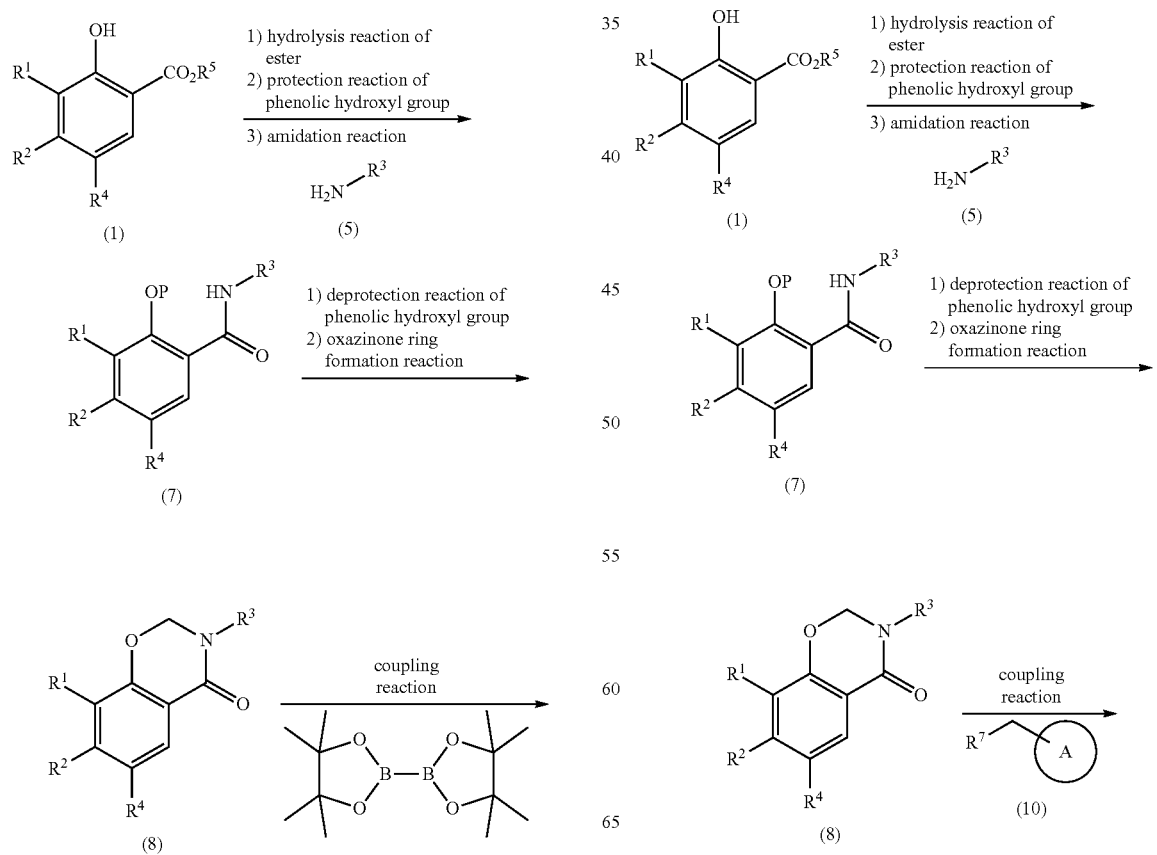

59

-continued

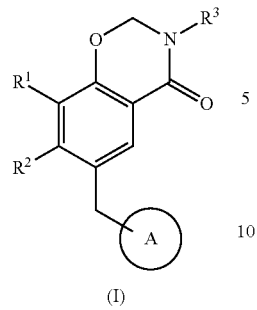

(I)

wherein $R^7$ is zinc halide, and ring A, $R^1$-$R^5$ and P are as defined above.

Compound (I) can also be produced from compound (1) by the following method.

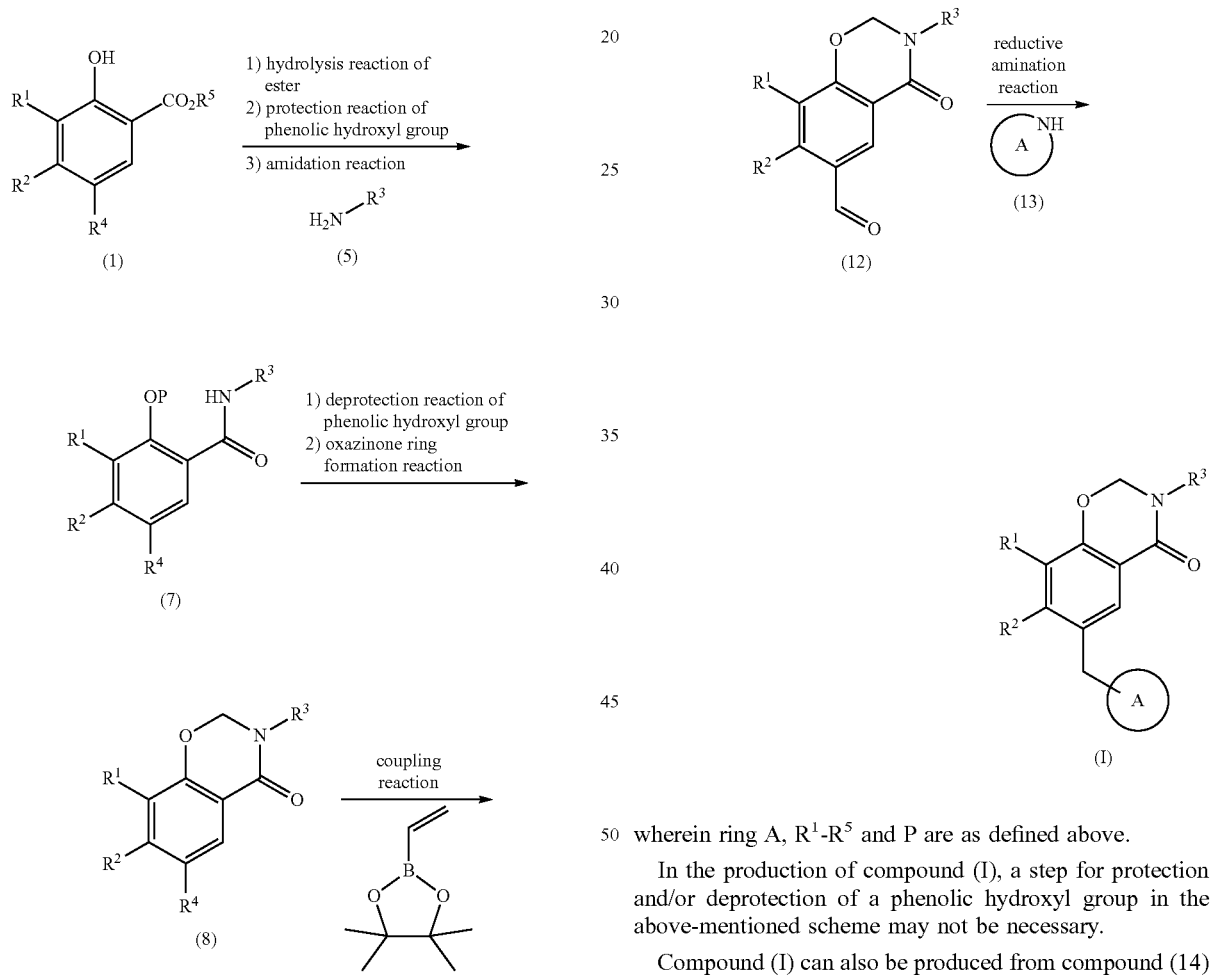

60

-continued

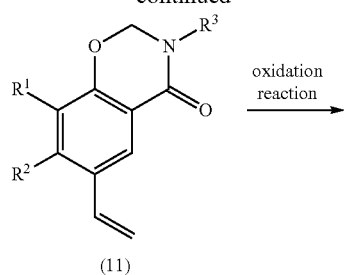

(I)

wherein ring A, $R^1$-$R^5$ and P are as defined above.

In the production of compound (I), a step for protection and/or deprotection of a phenolic hydroxyl group in the above-mentioned scheme may not be necessary.

Compound (I) can also be produced from compound (14) by the following method.

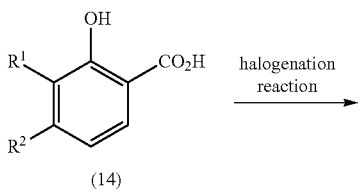

(14)

halogenation reaction

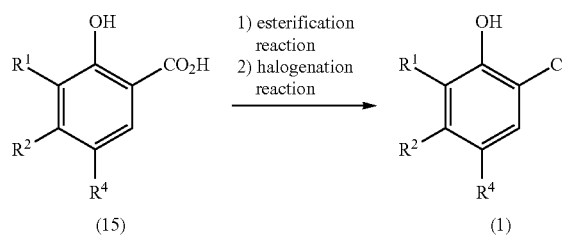
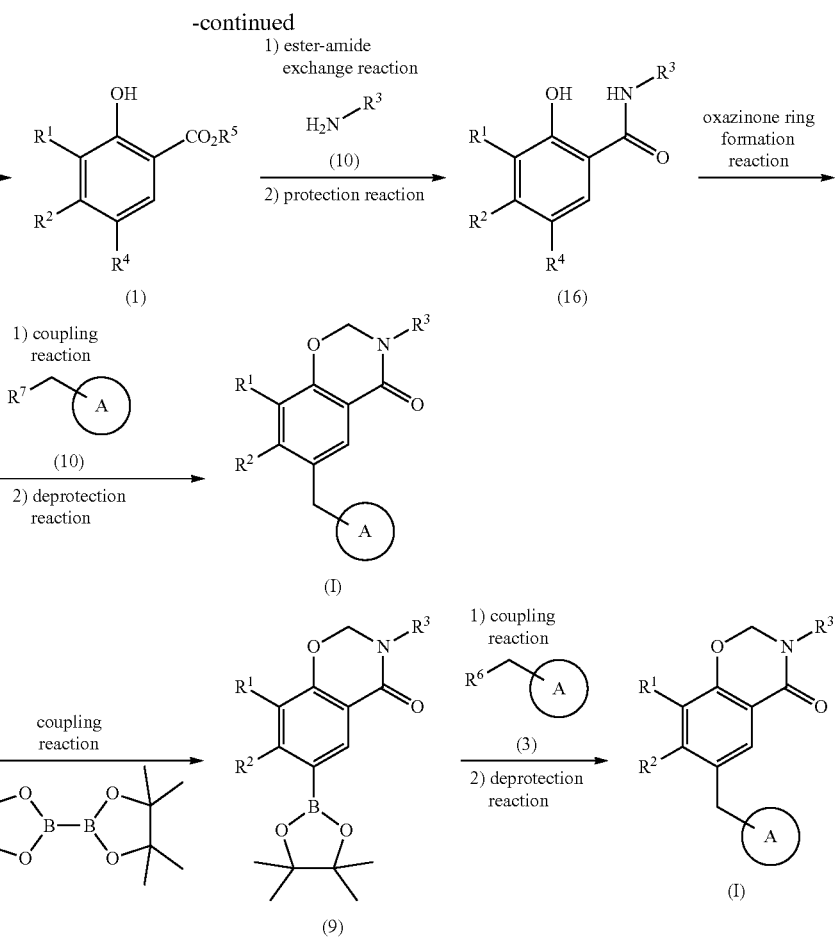

wherein ring A and $R^1$-$R^7$ are as defined above.

In the reaction scheme from compound (15) to (1), a step for halogenation reaction in the above-mentioned scheme may not be necessary.

In the production of compound (I), a step for protection reaction and/or deprotection reaction in the above-mentioned scheme may not be necessary.

In the production of compound (I), a compound having a benzene ring, a pyridine ring and a pyrazine ring formed between $R^1$ and $R^2$ can also be produced in the above-mentioned scheme.

Where necessary, in any of the above-mentioned reaction schemes, ring A and $R^1$-$R^7$ in the reaction schemes of compounds (1) to (16) can also be converted by using general organic reactions, such as halogenation reaction, acylation reaction, sulfonylation reaction, alkylation reaction, hydrolysis reaction, amination reaction, amidation reaction, esterification reaction, etherification reaction, oxidation reaction, reduction reaction, protection reaction, deprotection reaction, coupling reaction, addition reaction, elimination reaction, substitution reaction and the like, singly or in combination of a plurality thereof.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I)

The optical isomer can be produced according to a method known per se. To be specific, the optical isomer is obtained using an optically active synthetic intermediate, or subjecting the final racemate product to an optical resolution according to a conventional method.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (-)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When compound (I) is obtained as a free compound, the compound can be converted to an objective salt according to a method known per se or a method analogous thereto. Conversely, when it is obtained in the form of a salt, the salt can be converted to a free form or other objective salt according to a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or t-butylation, and the like); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like); a compound obtained by subjecting a carboxy group in compound (I) to esterification or amidation (e.g., a compound obtained by subjecting a carboxy group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autism spectrum syndrome, fragile X syndrome, Rett syndrome, adjustment disorder, bipolar disorder, neurosis, schizophrenia (e.g., positive symptom, negative symptom, and cognitive impairment), cognitive impairment associated with schizophrenia, chronic fatigue syndrome, anxiety neurosis, compulsive neurosis, epilepsy, anxiety symptom, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Parkinson's disease dementia, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's syndrome, vascular dementia, post-encephalitic parkinsonism, dementia with Lewy bodies, HIV dementia, amyotrophic lateral sclerosis (ALS), motor neurogenesis disease (MND), Creutzfeldt-Jakob disease or prion disease, cerebral palsy, multiple sclerosis], (3) age-related cognition and memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nerological vomiting, diarrhea, constipation, postoperative ileus, and (7) pain.

A cholinergic muscarinic M1 receptor positive allosteric modulator may be particularly preferably useful for the prophylaxis or treatment of Alzheimer's disease, schizophrenia, pain, sleep disorder, Parkinson's disease dementia, dementia with Lewy bodies and the like.

Compound (I) may have a high cholinergic muscarinic M1 receptor positive allosteric modulator activity, and it may be expected to provide an excellent prophylactic or therapeutic effect for the above-mentioned diseases.

Compound (I) may show excellent solubility in water, the second solution of Japanese Pharmacopeia Elution Test, or the second solution of Japanese Pharmacopoeia Disintegration Test, may show excellent in vivo kinetics (e.g., plasma drug half-life, intracerebral migration, metabolic stability, CYP inhibition), may show low toxicity (e.g., more excellent as a medicament in terms of acute toxicity, chronic toxicity, genetic toxicity, reproductive toxicity, cardiotoxicity, drug interaction, carcinogenicity, phototoxicity, and the like), and may also have excellent properties as a pharmaceutical product such as a few side effects. Therefore, compound (I) may be able to be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A preparation containing compound (I) may be any of a solid preparation such as powder, granule, tablet, capsule, orally disintegrable film and the like, or a liquid agent such as syrup, emulsion, injection and the like.

The medicament of the present invention may be able to be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation may be able to be produced according to the method described in JP-A-H9-263545.

In the preparation of the present invention, the content of compound (I) varies depending on the form of the preparation, but may be generally 0.01 to 100% by weight, preferably 0.1 to 50% by weight, more preferably 0.5 to 20% by weight, as the amount of compound (I) relative to the whole preparation.

When compound (I) is used as the above-mentioned pharmaceutical products, it may be used alone or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and safely administered orally or parenterally. When compound (I) is formed as a preparation for topical administration, it may also be directly administered to the affected part of an articular disease. In this case, an injection is preferable. The compound may also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension may be obtained by dispersing the compound together with vegetable oil such as sesame oil, corn oil and the like or a mixture thereof with a phospholipid such as lecithin and the like, or medium-chain triglyceride (e.g., miglyol 812 etc.) to give an injection to be actually used.

The dose of compound (I) may vary depending on the subject of administration, administration route and symptoms and is not particularly limited. For example, for oral administration to adult patients (body weight adult 40 to 80 kg, for example, 60 kg) with Alzheimer's disease, the dose may be, for example, 0.001 to 1000 mg/kg body weight/day, preferably 0.01 to 100 mg/kg body weight/day, more preferably 0.1 to 10 mg/kg body weight/day, as compound (I). This amount may be administered in one to three portions per day.

A medicament containing the compound of the present invention may be able to use the compound of the present invention solely or as a pharmaceutical composition of the compound of the present invention mixed with a pharmaceutically acceptable carrier according to a method known per se (e.g., the method described in the Japanese Pharmacopoeia etc.) as the production method of a pharmaceutical preparation. The medicament containing the compound of the present invention may be able to be administered safely as, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) may be used. For example, excipient, lubricant, binder, disintegrant and the like are used for solid preparations, and solvent, solubilizing agent, suspending agent, isotonic agent, buffer, soothing agent and the like are used for liquid preparations. Where necessary, preparation additives such as preservative, antioxidant, colorant, sweetening agent and the like may also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salt, ascorbic acid, α-tocopherol and the like.

While the pharmaceutical composition may vary according to the dosage form, administration method, carrier and the like, it may be able to be produced according to a conventional method by adding the compound of the present invention in a proportion of generally 0.01-100% (w/w), preferably 0.1-95% (w/w), of the total amount of the preparation.

The compound of the present invention may be able to be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrochloride etc.), 5-$HT_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (aprepitant, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autisma, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination of those drugs etc.), therapeutic drug for Parkinson's disease dementia (rivastigmine), therapeutic drug for dementia with Lewy bodies (donepezil), therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as
(1) the dose may be able to be reduced as compared to single administration of the compound of the present invention or a concomitant drug,
(2) the drug to be combined with the compound of the present invention may be able to be selected according to the condition of patients (mild case, severe case and the like),
(3) the period of treatment may be able to be set longer by selecting a concomitant drug having different action and mechanism from the compound of the present invention,
(4) a sustained treatment effect may be able to be designed by selecting a concomitant drug having different action and mechanism from the compound of the present invention,
(5) a synergistic effect may be able to be afforded by a combined use of the compound of the present invention and a concomitant drug, and the like, may be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof may be able to be administered to an administration subject simultaneously, or may be administered at different times. The dosage of the concomitant drug may be determined according to the dose clinically used, and may be appropriately selected depending on an administration subject, administration route, disease, combination and the like.

The administration mode of the combination agent of the present invention is not particularly restricted, and it may be sufficient that the compound of the present invention and the concomitant drug may be combined in administration. Examples of such administration mode include the following methods:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The combination agent of the present invention may exhibit low toxicity. For example, the compound of the present invention or(and) the aforementioned concomitant drug may be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions may be administered safely orally or non-orally (e.g., topical, rectal, intravenous administration etc.). Injection may be administered intravenously, intramuscularly, subcutaneously, or by intraorgan administration or directly to the lesion.

Examples of the pharmacologically acceptable carriers usable for the production of a combination agent in the present invention, various organic or inorganic carrier substances conventionally used as preparation materials may be mentioned. For solid preparations, for example, excipient, lubricant, binder and disintegrant may be used. For liquid preparations, for example, solvent, solubilizing agent, suspending agent, isotonic agent, buffering agent, soothing agent and the like may be used. Where necessary, additives such as conventional preservative, antioxidant, colorant, sweetening agent, adsorbent, wetting agent and the like may be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salt, ascorbic acid, α-tocopherol and the like.

The mixing ratio of the compound of the present invention to the concomitant drug in the combination agent of the present invention may be able to be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the whole preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The "osmium oxide (fixed catalyst I)" in Example means osmium oxide (VIII) (about 7% content) fixed to high solvent resistance polymer, which is commercially available from Wako Pure Chemical Industries, Ltd., unless otherwise specified. In addition, "sodium hydride" means a 60% oil dispersion (mineral mixture).

In the following Examples, the following abbreviations are used.
mp: melting point
MS: mass spectrum
M: molar concentration
N: normal concentration
$CDCl_3$: deuterated chloroform
DMSO: dimethyl sulfoxide
DMSO-$d_6$: deuterated dimethyl sulfoxide
$^1$H NMR: proton nuclear magnetic resonance
LC/MS: liquid chromatography mass spectrometer
ESI: electrospray ionization
APCI: atmospheric chemical ionization
DME: 1,2-dimethoxyethane
DMF: N,N-dimethylformamide
DMA: N,N-dimethylacetamide
THF: tetrahydrofuran
HATU: O-(7-azabenzotriazol-1-yl)-N,N,N',N'-tetramethyluronium hexafluorophosphorate
HOBt: 1-hydroxybenzotriazole
WSC: 1-ethyl-3-(3-dimethylaminopropyl) carbodiimide $^1$H NMR was measured by Fourier-transform NMR. For the analysis, ACD/SpecManager (trade name) and the like were used. Very mild peaks for protons of a hydroxy group, an amino group and the like are not described.

MS was measured by LC/MS. As ionization, ESI method or APCI method was used. The data indicates those actual measured (found). Generally, molecular ion peaks ([M+H]$^+$, [M−H]$^-$ and the like) are observed. In the case of a compound having a tert-butoxycarbonyl group, a peak after elimination of a tert-butoxycarbonyl group or tert-butyl group may be observed as a fragment ion. In the case of a compound having a hydroxy group, a peak after elimination of $H_2O$ may be observed as a fragment ion. In the case of a salt, a molecular ion peak or fragment ion peak of free form is generally observed.

X-ray powder diffraction patterns were generated using a Rigaku Ultima IV (Rigaku, Tokyo, Japan) with Copper K-alpha radiation.

In the following Examples, all reactions are conducted at room temperature unless otherwise noted.

Example 1

8-fluoro-3-((3S,4S)-4-hydroxytetrahydro-2H-pyran-3-yl)-7-methyl-6-(4-(1H-pyrazol-1-yl)benzyl)-2,3-dihydro-4H-1,3-benzoxazin-4-one Alias; 1,5-anhydro-2,4-dideoxy-2-(8-fluoro-7-methyl-4-oxo-6-(4-(1H-pyrazol-1-yl)benzyl)-2H-1,3-benzoxazin-3(4H)-yl)-L-threo-pentitol A) 3-fluoro-2-hydroxy-4-methylbenzaldehyde To a mixture of 2-fluoro-3-methylphenol (14.9 g), triethylamine (99 mL) and 1,2-dichloroethane (150 mL) was added magnesium chloride (56.2 g), and the mixture was stirred at 40° C. for 1 hr. To this reaction mixture was added paraformaldehyde (35.4 g), and the mixture was stirred at 70° C. for 4 hr. Under ice-cooling, the reaction mixture was poured into 1N hydrochloric acid (450 mL), and the mixture was extracted with ethyl acetate. The organic layer was washed with water and brine, and dried over anhydrous magnesium sulfate. The solvent was evaporated under reduced pressure. The residue was purified by silica gel column chromatography (ethyl acetate/hexane) to give the title compound (9.47 g).

$^1$H NMR (300 MHz, $CDCl_3$) δ 2.35 (3H, d, J=2.5 Hz), 6.78-6.86 (1H, m), 7.25 (1H, dd, J=8.1, 1.5 Hz), 9.85 (1H, d, J=1.9 Hz), 10.99 (1H, brs).

B) Methyl 3-fluoro-2-hydroxy-4-methylbenzoate

To an aqueous solution (50.0 mL) of sodium chlorite (22.2 g) was added a mixture of 3-fluoro-2-hydroxy-4-methylbenzaldehyde (9.47 g), sodium dihydrogen phosphate (33.2 g) and 2-methyl-2-butene (32.5 mL) in tert-butanol (200 mL)-water (100 mL) under ice-cooling, and the mixture was stirred at the same temperature for 3 hr. To the reaction mixture was added 2N hydrochloric acid, and the mixture was adjusted to pH 2-3. To the reaction mixture was added water, and the mixture was extracted with ethyl acetate. The organic layer was washed with water and brine, and dried over anhydrous magnesium sulfate. The solvent was evaporated under reduced pressure to give a crude product (10.5 g). To a solution of the obtained crude product (10.5 g) in methanol (50.0 mL) was added sulfuric acid (5.00 mL) at room temperature, and the mixture was stirred at 60° C. for 24 hr. The solvent was evaporated under reduced pressure, water and ethyl acetate were added to the residue, and the mixture was extracted with ethyl acetate. The organic layer was washed with water and brine, and dried over anhydrous magnesium sulfate. The solvent was evaporated under reduced pressure. The residue was purified by silica gel column chromatography (ethyl acetate/hexane) to give the title compound (6.40 g).

MS: [M+H]$^+$ 185.0

C) Methyl 5-bromo-3-fluoro-2-hydroxy-4-methylbenzoate

To a solution of methyl 3-fluoro-2-hydroxy-4-methylbenzoate (6.40 g) in acetic acid (120 mL) was added bromine (1.87 mL) at room temperature, and the mixture was stirred at the same temperature for 2 hr. To the reaction mixture was added 10% aqueous sodium thiosulfate solution, and the mixture was extracted with ethyl acetate. The organic layer was washed with water and brine, and dried over anhydrous magnesium sulfate. The solvent was evaporated under reduced pressure to give a mixture of the title compound and the starting material at a ratio of about 2:1 (7.99 g). The obtained resultant product was used in the next step without further purification.

$^1$H NMR (300 MHz, CDCl$_3$) δ 2.38 (3H, d, J=2.8 Hz), 3.98 (3H, s), 7.82 (1H, d, J=2.1 Hz), 10.67 (1H, s).

D) Methyl 3-fluoro-2-hydroxy-4-methyl-5-(4,4,5,5-tetramethyl-1,3,2-dioxaborolan-2-yl)benzoate Dichlorobis(triphenylphosphine)palladium (II) (1.07 g) was added to a mixture of a 2:1 mixture (7.99 g) of methyl 5-bromo-3-fluoro-2-hydroxy-4-methylbenzoate and methyl 3-fluoro-2-hydroxy-4-methylbenzoate, bis(pinacolato)diboron (11.6 g), potassium acetate (8.94 g) and toluene (160 mL) under an argon atmosphere at room temperature, and the mixture was stirred at 100° C. for 2 hr. To the reaction mixture was added dichlorobis(triphenylphosphine)palladium (II) (1.07 g), and the mixture was stirred at 100° C. for 3 days. To the reaction mixture was further added dichlorobis(triphenylphosphine)palladium (II) (1.07 g), and the mixture was stirred at 100° C. overnight. The reaction mixture was cooled to room temperature, water was added, and the precipitates were collected by filtration. The filtrate was extracted with ethyl acetate, and the organic layer was washed with water and saturated brine, and dried over anhydrous magnesium sulfate. The solvent was evaporated under reduced pressure. The residue was purified by silica gel column chromatography (ethyl acetate/hexane) to give the title compound (2.20 g). Furthermore, the title compound (4.03 g) was obtained from the second fraction of column chromatography.

MS: [M+H]$^+$ 311.1

E) Methyl 5-(4-(1H-pyrazol-1-yl)benzyl)-3-fluoro-2-hydroxy-4-methylbenzoate

Tetrakis(triphenylphosphine)palladium (0) (0.40 g) was added to a mixture of methyl 3-fluoro-2-hydroxy-4-methyl-5-(4,4,5,5-tetramethyl-1,3,2-dioxaborolan-2-yl)benzoate (2.13 g), 1-(4-(chloromethyl)phenyl)-1H-pyrazole (1.32 g), sodium carbonate (1.46 g), DME (30.0 mL) and water (10.0 mL) under an argon atmosphere, and the mixture was stirred at 80° C. overnight. The reaction mixture was cooled to room temperature, water was added and the mixture was extracted with ethyl acetate. The organic layer was washed with brine, and dried over anhydrous magnesium sulfate. The solvent was evaporated under reduced pressure. The residue was purified by silica gel column chromatography (ethyl acetate/hexane) to give the title compound (0.33 g).

MS: [M+H]$^+$ 341.1

F) 5-(4-(1H-pyrazol-1-yl)benzyl)-3-fluoro-2-hydroxy-4-methylbenzoic Acid

A mixture of methyl 5-(4-(1H-pyrazol-1-yl)benzyl)-3-fluoro-2-hydroxy-4-methylbenzoate (1.54 g), 8N aqueous sodium hydroxide solution (15 mL), THF (15 mL) and methanol (15 mL) was stirred at 70° C. overnight. To the reaction mixture was added 6N hydrochloric acid in an ice bath to adjust pH to 4. The resulting precipitates were collected by filtration, and dried to give the title compound (1.44 g).

MS: [M+H]$^+$ 327.1

G) 5-(4-(1H-pyrazol-1-yl)benzyl)-3-fluoro-2-hydroxy-N-((3S,4S)-4-hydroxytetrahydro-2H-pyran-3-yl)-4-methylbenzamide To a mixture of 5-(4-(1H-pyrazol-1-yl)benzyl)-3-fluoro-2-hydroxy-4-methylbenzoic acid (0.16 g), (3S,4S)-3-aminotetrahydro-2H-pyran-4-ol (0.06 g), WSC hydrochloride (0.11 g), HOBt monohydrate (0.08 g) and DMF (3 mL) was added triethylamine (0.07 mL), and the mixture was stirred at room temperature overnight. To the reaction mixture was added water, and the mixture was extracted with ethyl acetate. The organic layer was washed with water and brine, dried over anhydrous magnesium sulfate and concentrated under reduced pressure to give the title compound (0.20 g). This was used in the next step without further purification.

MS: [M+H]$^+$ 426.4

H) 8-fluoro-3-((3S,4S)-4-hydroxytetrahydro-2H-pyran-3-yl)-7-methyl-6-(4-(1H-pyrazol-1-yl)benzyl)-2,3-dihydro-4H-1,3-benzoxazin-4-one Alias; 1,5-anhydro-2,4-dideoxy-2-(8-fluoro-7-methyl-4-oxo-6-(4-(1H-pyrazol-1-yl)benzyl)-2H-1,3-benzoxazin-3(4H)-yl)-L-threo-pentitol To a mixture of 5-(4-(1H-pyrazol-1-yl)benzyl)-3-fluoro-2-hydroxy-N-((3S,4S)-4-hydroxytetrahydro-2H-pyran-3-yl)-4-methylbenzamide (0.20 g) and formic acid (2 mL) was added formaldehyde (37% aqueous solution) (2 mL) at room temperature, and the mixture was stirred at 60° C. overnight, and further at 90° C. for 7 hr. The reaction mixture was neutralized with saturated aqueous sodium hydroxide solution at 0° C., and extracted with ethyl acetate. The organic layer was washed with water and brine, dried over anhydrous magnesium sulfate, and concentrated under reduced pressure. The residue was purified by NH silica gel column chromatography (ethyl acetate/hexane) to give the title compound (0.01 g).

$^1$H NMR (300 MHz, CDCl$_3$) δ 1.65-1.90 (1H, m), 1.95-2.14 (2H, m), 2.18 (3H, d, J=2.6 Hz), 3.41-3.52 (1H, m), 3.60-3.78 (1H, m), 3.90-4.22 (6H, m), 5.30 (2H, d, J=1.1 Hz), 6.38-6.50 (1H, m), 7.12-7.21 (2H, m), 7.50-7.63 (3H, m), 7.70 (1H, d, J=1.5 Hz), 7.88 (1H, d, J=2.5 Hz).

Example 2

8-chloro-3-((1S,2S)-2-hydroxycyclohexyl)-7-methyl-6-((6-methylpyridin-3-yl)methyl)-2,3-dihydro-4H-1,3-benzoxazin-4-one A) Methyl 5-bromo-3-chloro-2-hydroxy-4-methylbenzoate To a mixture of methyl 5-bromo-2-hydroxy-4-methylbenzoate (13.4 g) and DMF (130 mL) was added N-chlorosuccinimide (7.27 g) at room temperature, and the mixture was stirred at the same temperature overnight. To the reaction mixture were added ethyl acetate and 10% aqueous sodium thiosulfate solution at room temperature, and the mixture was extracted with ethyl acetate. The organic layer was washed with water and brine, dried over anhydrous magnesium sulfate, and concentrated under reduced pressure. The residue was collected, washed with diisopropyl ether, and dried to give the title compound (9.95 g).

MS: [M–H]$^-$ 276.9

$^1$H NMR (300 MHz, CDCl$_3$) δ 2.57 (3H, s), 3.98 (3H, s), 7.96 (1H, s), 11.27 (1H, s).

B) 5-bromo-3-chloro-2-hydroxy-N-((1S,2S)-2-hydroxycyclohexyl)-4-methylbenzamide

To a mixture of methyl 5-bromo-3-chloro-2-hydroxy-4-methylbenzoate (1.0 g), THF (15 mL) and methanol (5 mL) was added 1N aqueous sodium hydroxide solution (7.87 mL) at room temperature, and the mixture was stirred at the same temperature for 1 hr, and at 60° C. for 3 hr. To the reaction mixture were added ethyl acetate and water, the aqueous layer was separated, 1N hydrochloric acid was added to adjust pH to 2-3, and the mixture was extracted with ethyl acetate. The organic layer was washed with water and brine, dried over anhydrous magnesium sulfate and concentrated under reduced pressure. To a mixture of the residue and DMA (20 mL) was added benzoyl chloride (0.42 mL) at room temperature, and the mixture was stirred at the same temperature for 1 hr. The reaction mixture was poured into water, and the mixture was extracted with ethyl acetate. The organic layer was washed with water and brine, dried over anhydrous magnesium sulfate and concentrated under reduced pressure. To a mixture of the residue, (1S,2S)-2-aminocyclohexanol (0.41 g), HOBt monohydrate (0.55 g), triethylamine (0.50 mL) and DMA (20 mL) was added WSC hydrochloride (0.69 g) at 0° C., and the mixture was stirred at room temperature overnight. The reaction mixture was poured into water, and the mixture was extracted with ethyl acetate. The organic layer was washed with water and brine, dried over anhydrous magnesium sulfate and concentrated under reduced pressure.

To a mixture of the residue, THF (15 mL) and methanol (5 mL) was added 1N aqueous sodium hydroxide solution (7.16 mL) at room temperature, and the mixture was stirred at the same temperature overnight. To the reaction mixture were added ethyl acetate, water and 1N hydrochloric acid to adjust pH to 2-3, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.23 g).

MS: [M+H]$^+$ 362.1, 364.0

C) 6-bromo-8-chloro-3-((1S,2S)-2-hydroxycyclohexyl)-7-methyl-2H-benzo[e][1,3]oxazin-4 (3H)-one To a mixture of 5-bromo-3-chloro-2-hydroxy-N-((1S,2S)-2-hydroxycyclohexyl)-4-methylbenzamide (0.23 g), paraformaldehyde (0.05 g) and toluene (5 mL) was added D(+)-10-camphorsulfonic acid (0.02 g) at room temperature, and the mixture was stirred at 110° C. for 2 hr. The reaction mixture was diluted with saturated aqueous sodium hydrogen carbonate solution and extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.08 g).

MS: [M+H]$^+$ 374.1, 376.0

D) 8-chloro-3-((1S,2S)-2-hydroxycyclohexyl)-7-methyl-6-((6-methylpyridin-3-yl)methyl)-2,3-dihydro-4H-1,3-benzoxazin-4-one To a mixture of 6-bromo-8-chloro-3-((1S,2S)-2-hydroxycyclohexyl)-7-methyl-2H-benzo [e][1,3]oxazin-4 (3H)-one (0.08 g), bis(tri-tert-butylphosphine)palladium (0) (0.01 g) and THF (1 mL) was added ((6-chloropyridin-3-yl)methyl) zinc (II) chloride (0.5 M THF solution) (0.85 mL) under an argon atmosphere at room temperature, and the mixture was stirred at the same temperature overnight. The reaction mixture was poured into water, and the mixture was extracted with ethyl acetate. The organic layer was washed with water and brine, dried over anhydrous magnesium sulfate and concentrated under reduced pressure.

To a mixture of the residue, 1,1'-bis(diphenylphosphino) ferrocene palladium (II) chloride dichloromethane complex (0.02 g) and THF (1 mL) was added methylzinc (II) chloride (2 M THF solution) (0.27 mL) under an argon atmosphere at room temperature, and the mixture was stirred at 60° C. for 3 hr, and further at room temperature overnight. To the reaction mixture were added ethyl acetate and saturated aqueous ammonium chloride solution, and the mixture was extracted with ethyl acetate. The organic layer was washed with water and brine, dried over anhydrous magnesium sulfate and concentrated under reduced pressure. The residue was purified by NH silica gel column chromatography (ethyl acetate/hexane) to give the title compound (0.01 g).

$^1$H NMR (300 MHz, CDCl$_3$) δ 1.25-1.48 (3H, m), 1.56-1.63 (1H, m), 1.81 (2H, d, J=9.4 Hz), 1.87-1.96 (2H, m), 2.12-2.22 (1H, m), 2.31 (3H, s), 2.51 (3H, s), 3.52-3.64 (1H, m), 3.98 (2H, s), 4.17 (1H, ddd, J=12.2, 10.4, 4.0 Hz), 5.23-5.33 (2H, m), 7.04 (1H, d, J=8.1 Hz), 7.21-7.26 (1H, m), 7.69 (1H, s), 8.32 (1H, d, J=2.1 Hz).

Example 3

1,5-anhydro-2,4-dideoxy-2-(6-((6-methylpyridin-3-yl)methyl)-4-oxo-2H-naphtho[2,1-e][1,3]oxazin-3(4H)-yl)-threo-pentitol Monohydrochloride (Optical Isomer)

A) 4-bromo-1-hydroxy-N-(trans-4-hydroxytetrahydro-2H-pyran-3-yl)-2-naphthamide To a mixture of 4-bromo-1-hydroxy-2-naphthoic acid (1.2 g), trans-3-aminotetrahydro-2H-pyran-4-ol hydrochloride (0.76 g), WSC hydrochloride (0.95 g), HOBt monohydrate (0.69 g) and DMF (10 mL) was added triethylamine (0.75 mL), and the mixture was stirred at room temperature for 5 days. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.90 g).

MS: [M−H]⁻ 363.9, 365.9

B) 6-bromo-3-(trans-4-hydroxytetrahydro-2H-pyran-3-yl)-2H-naphtho[2,1-e][1,3]oxazin-4(3H)-one To a mixture of 4-bromo-1-hydroxy-N-(trans-4-hydroxytetrahydro-2H-pyran-3-yl)-2-naphthamide (0.90 g) and formic acid (2 mL) was added formaldehyde (37% aqueous solution) (2 mL), and the mixture was stirred at 80° C. overnight. The reaction mixture was neutralized with saturated aqueous sodium hydroxide solution at 0° C., and extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.12 g).

MS: [M+H]⁺ 378.1, 380.1

C) 6-((6-chloropyridin-3-yl)methyl)-3-(trans-4-hydroxytetrahydro-2H-pyran-3-yl)-2H-naphtho[2,1-e][1,3]oxazin-4(3H)-one To a mixture of 6-bromo-3-(trans-4-hydroxytetrahydro-2H-pyran-3-yl)-2H-naphtho[2,1-e][1,3]oxazin-4(3H)-one (0.12 g), bis(tri-tert-butylphosphine)palladium (0) (0.01 g) and THF (1 mL) was added (6-chloro-3-pyridyl)methylzinc chloride (0.5 M THF solution) (1.27 mL), and the mixture was stirred under an argon atmosphere at 90° C. for 4 hr. To the reaction mixture was added water, and the mixture was extracted with a mixed solvent of ethyl acetate and THF. The organic layer was washed with water and brine, dried over anhydrous magnesium sulfate and concentrated under reduced pressure. The residue was purified by silica gel column chromatography (ethyl acetate/hexane) to give the title compound (0.10 g).

MS: [M+H]⁺ 425.1

D) 1,5-anhydro-2,4-dideoxy-2-(6-((6-methylpyridin-3-yl)methyl)-4-oxo-2H-naphtho[2,1-e][1,3]oxazin-3(4H)-yl)-threo-pentitol To a mixture of 6-((6-chloropyridin-3-yl)methyl)-3-(trans-4-hydroxytetrahydro-2H-pyran-3-yl)-2H-naphtho[2,1-e][1,3]oxazin-4(3H)-one (0.09 g), 1,1'-bis(diphenylphosphino)ferrocene palladium (II) chloride dichloromethane complex (0.01 g) and THF (2 mL) was added methylzinc chloride (2 M THF solution) (0.21 mL), and the mixture was stirred under an argon atmosphere at 80° C. overnight. Furthermore, methylzinc chloride (2 M THF solution) (0.11 mL) was added and the mixture was stirred at 80° C. overnight. To the reaction mixture was added water, and the mixture was extracted with a mixed solvent of ethyl acetate and THF. The organic layer was washed with water and brine, dried over anhydrous magnesium sulfate and concentrated under reduced pressure. The residue was purified by NH silica gel column chromatography (ethyl acetate/hexane) to give the title compound (0.07 g).

MS: [M+H]⁺ 405.2

E) 1,5-anhydro-2,4-dideoxy-2-(6-((6-methylpyridin-3-yl)methyl)-4-oxo-2H-naphtho[2,1-e][1,3]oxazin-3(4H)-yl)-threo-pentitol Monohydrochloride (Optical Isomer)

1,5-Anhydro-2,4-dideoxy-2-(6-((6-methylpyridin-3-yl)methyl)-4-oxo-2H-naphtho[2,1-e][1,3]oxazin-3(4H)-yl)-threo-pentitol (0.044 g) was optically resolved by HPLC (Chiral PAK AD, 50 mm ID×500 mm L, mobile phase: ethanol) to give a product with a longer retention time (0.026 g). To a mixture of the obtained crude product (0.022 g), ethyl acetate (1 mL) and ethanol (0.2 mL) was added 4N hydrogen chloride (ethyl acetate solution) (0.01 mL), and the mixture was stirred for 10 min. The resulting solid was collected by filtration, washed with ethyl acetate, and dried under reduced pressure to give the title compound (0.017 g).

$^1$H NMR (300 MHz, DMSO-d$_6$) δ 1.53 (1H, d, J=12.9 Hz), 1.95 (1H, d, J=8.3 Hz), 2.62 (3H, s), 3.48-3.57 (2H, m), 3.73-4.07 (5H, m), 4.57 (2H, s), 5.49-5.62 (2H, m), 7.56-7.76 (3H, m), 7.78 (1H, s), 8.12 (2H, d, J=8.4 Hz), 8.20 (1H, d, J=7.5 Hz), 8.74 (1H, s). The peak of one proton was not observed.

Example 4

1,5-anhydro-2-(6-((6-chloropyridin-3-yl)methyl)-4-oxo-2H-naphtho[2,1-e][1,3]oxazin-3(4H)-yl)-2,4-dideoxy-L-threo-pentitol

A) 4-bromo-1-hydroxy-N-((3S,4S)-4-hydroxytetrahydro-2H-pyran-3-yl)-2-naphthamide To a mixture of 4-bromo-1-hydroxy-2-naphthoic acid (3.0 g), (3S,4S)-3-aminotetrahydro-2H-pyran-4-ol (1.38 g), WSC hydrochloride (2.58 g), HOBt monohydrate (1.89 g) and DMF (10 mL) was added triethylamine (2.19 mL), and the mixture was stirred at room temperature for 5 days. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (1.47 g).

MS: [M+H]⁺ 366.1, 368.1

B) 6-bromo-3-((3S,4S)-4-hydroxytetrahydro-2H-pyran-3-yl)-2H-naphtho[2,1-e][1,3]oxazin-4(3H)-one To a mixture of 4-bromo-1-hydroxy-N-((3S,4S)-4-hydroxytetrahydro-2H-pyran-3-yl)-2-naphthamide (1.0 g) and formic acid (4 mL) was added formaldehyde (37% aqueous solution) (4 mL), and the mixture was stirred at 80° C.

overnight. The reaction mixture was neutralized with saturated aqueous sodium hydroxide solution at 0° C., and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.25 g).

MS: [M+H]$^+$ 378.1, 380.1

C) 1,5-anhydro-2-(6-((6-chloropyridin-3-yl)methyl)-4-oxo-2H-naphtho[2,1-e][1,3]oxazin-3(4H)-yl)-2,4-dideoxy-L-threo-pentitol To a mixture of 6-bromo-3-((3S,4S)-4-hydroxytetrahydro-2H-pyran-3-yl)-2H-naphtho[2,1-e][1,3]oxazin-4(3H)-one (0.25 g), bis(tri-tert-butylphosphine)palladium (0) (0.02 g) and THF (1 mL) was added (6-chloro-3-pyridyl)methylzinc chloride (0.5 M THF solution) (2.67 mL), and the mixture was stirred under an argon atmosphere at 90° C. for 4 hr. To the reaction mixture was added water at room temperature, and the mixture was extracted with a mixed solution of ethyl acetate and THF. The organic layer was washed with water and brine, dried over anhydrous magnesium sulfate and concentrated under reduced pressure. The residue was purified by silica gel column chromatography (ethyl acetate/hexane) and crystallized from ethanol to give the title compound (0.10 g).

$^1$H NMR (300 MHz, CDCl$_3$) δ 1.69-1.88 (1H, m), 2.08-2.20 (1H, m), 2.28-2.35 (1H, m), 3.52 (1H, td, J=11.6, 2.4 Hz), 3.69-3.80 (1H, m), 3.97-4.11 (3H, m), 4.12-4.26 (1H, m), 4.34 (2H, s), 5.41-5.53 (2H, m), 7.17 (1H, d, J=8.3 Hz), 7.37 (1H, dd, J=8.2, 2.5 Hz), 7.57 (2H, td, J=7.3, 1.5 Hz), 7.77 (1H, s), 7.79-7.85 (1H, m), 8.20-8.27 (1H, m), 8.32 (1H, d, J=2.5 Hz).

Example 5

8-fluoro-3-((1S,2S)-2-hydroxycyclopentyl)-7-methyl-6-(4-(1H-pyrazol-1-yl)benzyl)-2,3-dihydro-4H-1,3-benzoxazin-4-one A) 3-fluoro-2-hydroxy-4-methylbenzoic acid A mixture of 2,3-difluoro-4-methylbenzoic acid (5.2 g), sodium hydroxide (4.83 g) and DMSO (60 mL) was stirred under a nitrogen atmosphere at 140° C. for 6 hr. The reaction mixture was partly concentrated, diluted with water, and added to 2N hydrochloric acid (150 mL) at 0° C. The resulting precipitates were collected by filtration to give the title compound (5.14 g).

MS: [M−H]$^-$ 169.1

B) 5-bromo-3-fluoro-2-hydroxy-4-methylbenzoic Acid

To a mixture of 3-fluoro-2-hydroxy-4-methylbenzoic acid (5.14 g) and acetic acid (70 mL) was added dropwise bromine (1.55 mL), and the mixture was stirred at room temperature for 4 hr. The reaction mixture was poured into water, and the resulting precipitates were collected by filtration, and dried under reduced pressure to give the title compound (6.34 g).

MS: [M−H]$^-$ 247.0, 249.1

C) 5-bromo-3-fluoro-2-hydroxy-N-((1S,2S)-2-hydroxycyclopentyl)-4-methylbenzamide To a suspension of 5-bromo-3-fluoro-2-hydroxy-4-methylbenzoic acid (1 g) in THF (20 mL) was added dropwise a mixture of oxalyl chloride (0.53 mL) and THF (4 mL) at 0° C. To the reaction mixture was added one drop of DMF, and the mixture was stirred at 16° C. for 1.5 hr. The reaction mixture was concentrated under reduced pressure, and the obtained acid chloride residue was dissolved in THF (20 mL). To a mixture of (1S,2S)-2-aminocyclopentanol hydrochloride (0.55 g), triethylamine (2.80 mL), THF (20 mL) and water (20 mL) was added dropwise a mixture of the above-mentioned acid chloride and THF at 0° C., and the mixture was stirred at room temperature overnight. To the reaction mixture was added water and the mixture was extracted with ethyl acetate. The organic layer was concentrated under reduced pressure. The residue was purified by silica gel column chromatography (ethyl acetate/hexane) to give the title compound (0.59 g).

MS: [M+H]$^+$ 332.0, 334.1

D) 6-bromo-8-fluoro-3-((1S,2S)-2-hydroxycyclopentyl)-7-methyl-2H-benzo[e][1,3]oxazin-4(3H)-one A mixture of 5-bromo-3-fluoro-2-hydroxy-N-((1S,2S)-2-hydroxycyclopentyl)-4-methylbenzamide (0.41 g), formaldehyde (37% aqueous solution) (1.5 g) and formic acid (2.5 g) was stirred under a nitrogen atmosphere at 50° C. overnight. The reaction mixture was neutralized by adding to ice and saturated sodium hydrogen carbonate solution, and the mixture was extracted with ethyl acetate. The organic layer was washed with brine, dried over anhydrous sodium sulfate, and concentrated under reduced pressure. The residue was purified by silica gel column chromatography (ethyl acetate/hexane) to give the title compound (0.28 g).

MS: [M+H]$^+$ 344.0, 346.0

E) 8-fluoro-3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one To a mixture of 6-bromo-8-fluoro-3-((1S,2S)-2-hydroxycyclopentyl)-7-methyl-2H-benzo[e][1,3]oxazin-4(3H)-one (1.45 g), bis(pinacolato)diboron (1.39 g), palladium (II) acetate (0.05 g) and DMF (10 mL) was added potassium acetate (0.83 g) at room temperature and the mixture was stirred under an argon atmosphere at 80° C. overnight. The reaction mixture was neutralized with saturated aqueous sodium hydrogen carbonate solution, and extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (1.73 g).

MS: [M+H]$^+$ 392.2

F) 8-fluoro-3-((1S,2S)-2-hydroxycyclopentyl)-7-methyl-6-(4-(1H-pyrazol-1-yl)benzyl)-2,3-dihydro-4H-1,3-benzoxazin-4-one To a mixture of 8-fluoro-3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one (0.07 g), sodium carbonate (0.04 g), 1-(4-(bromomethyl)phenyl)-1H-pyrazole (0.04 g), DME (1 mL) and water (0.33 mL) was added tetrakis(triphenylphosphine)palladium (0) (0.01 g) under an argon atmosphere and the mixture was stirred at 85° C. for 1 hr. The reaction mixture was diluted with ethyl acetate, dried over anhydrous sodium sulfate, and concentrated under reduced pressure. The residue was purified by silica gel column chromatography (ethyl acetate/hexane) and crystallized from ethyl acetate and hexane to give the title compound (0.06 g).

$^1$H NMR (300 MHz, CDCl$_3$) δ 1.65-1.95 (4H, m), 2.01-2.12 (2H, m), 2.18 (3H, d, J=2.5 Hz), 2.98 (1H, d, J=3.6 Hz), 4.01 (2H, s), 4.23 (1H, s), 4.36 (1H, t, J=7.5 Hz), 5.20-5.29 (2H, m), 6.43-6.47 (1H, m), 7.18 (2H, d, J=8.7 Hz), 7.58 (2H, s), 7.60-7.63 (1H, m), 7.71 (1H, d, J=1.3 Hz), 7.88 (1H, d, J=2.0 Hz).

Example 6

1,5-anhydro-2-(8-chloro-7-methyl-6-((6-methylpyridin-3-yl)methyl)-4-oxo-2H-1,3-benzoxazin-3(4H)-yl)-2,4-dideoxy-L-threo-pentitol A) 5-bromo-3-chloro-2-hydroxy-N-((3S,4S)-4-hydroxytetrahydro-2H-pyran-3-yl)-4-methylbenzamide To a mixture of 5-bromo-3-chloro-2-hydroxy-4-methyl-benzoic acid (4.48 g), (3S,4S)-3-aminotetrahydro-2H-pyran-4-ol (1.98 g), HOBt monohydrate (2.84 g), triethylamine (2.59 mL) and DMA (90 mL) was added WSC hydrochloride (3.56 g) at 0° C., and the mixture was stirred at 50° C. for 1 hr, and at 60° C. overnight. To the reaction mixture were added ethyl acetate and water, and the aqueous layer was extracted with ethyl acetate. The organic layer was washed with water and brine, dried over anhydrous magnesium sulfate and concentrated under reduced pressure. The residue was crudely purified by silica gel column chromatography (ethyl acetate/hexane) to give a mixture of the title compound and a byproduct (dechlorinated form) (0.64 g).

MS: [M-H]$^-$ 361.9, 363.9

B) 6-bromo-8-chloro-3-((3S,4S)-4-hydroxytetrahydro-2H-pyran-3-yl)-7-methyl-2H-benzo[e][1,3]oxazin-4(3H)-one To a mixture of 5-bromo-3-chloro-2-hydroxy-N-((3S,4S)-4-hydroxytetrahydro-2H-pyran-3-yl)-4-methylbenzamide (mixture with dechlorinated form) (0.64 g), paraformaldehyde (0.26 g) and toluene (15 mL) was added D(+)-10-camphorsulfonic acid (0.04 g) at room temperature, and the mixture was stirred at 110° C. overnight. The reaction mixture was diluted with saturated aqueous sodium hydrogen carbonate solution, and the mixture was extracted with ethyl acetate. The organic layer was washed with water and brine, dried over anhydrous magnesium sulfate and concentrated under reduced pressure. To a mixture of the residue, THF (10 mL) and methanol (5 mL) was added 1N aqueous sodium hydroxide solution (1.76 mL) at room temperature, and the mixture was stirred at the same temperature for 2 hr. To the reaction mixture were added ethyl acetate and water, and 1N hydrochloric acid was added to adjust pH to 2-3, and the mixture was extracted with ethyl acetate. The organic layer was washed with water and brine, dried over anhydrous magnesium sulfate and concentrated under reduced pressure. The residue was crudely purified by silica gel column chromatography (ethyl acetate/hexane) to give a mixture (1.0 g) of the title compound and a byproduct (dechlorinated form).

MS: [M+H]$^+$ 376.0, 378.1

C) 1,5-anhydro-2-(8-chloro-7-methyl-6-((6-methylpyridin-3-yl)methyl)-4-oxo-2H-1,3-benzoxazin-3(4H)-yl)-2,4-dideoxy-L-threo-pentitol To a mixture of 6-bromo-8-chloro-3-((3S,4S)-4-hydroxytetrahydro-2H-pyran-3-yl)-7-methyl-2H-benzo[e][1,3]oxazin-4(3H)-one (mixture with dechlorinated form) (0.66 g), bis(tri-tert-butylphosphine)palladium (0) (0.09 g) and THF (7 mL) was added ((6-chloropyridin-3-yl)methyl)zinc (II) chloride (0.5 M THF solution) (7.01 mL) under an argon atmosphere at room temperature, and the mixture was stirred at the same temperature overnight. To the reaction mixture were added ethyl acetate and water, and the insoluble material was filtered off. The filtrate was extracted with ethyl acetate, and the organic layer was washed with water and brine, dried over anhydrous magnesium sulfate and concentrated under reduced pressure.

To a mixture of the residue, 1,1'-bis(diphenylphosphino)ferrocene palladium (II) chloride dichloromethane complex (0.14 g) and THF (7 mL) was added methylzinc (II) chloride (0.5 M THF solution) (5.26 mL) under an argon atmosphere at room temperature, and the mixture was stirred at 80° C. for 2 hr. To the reaction mixture were added ethyl acetate and saturated aqueous ammonium chloride solution, and the insoluble material was filtered off. The filtrate was extracted with ethyl acetate, and the organic layer was washed with water and brine, dried over anhydrous magnesium sulfate and concentrated under reduced pressure. The residue was purified by NH silica gel column chromatography (ethyl acetate/hexane/methanol) and HPLC (L-Column 2, mobile phase: water/acetonitrile (containing 0.1% trifluoroacetic acid)) to give the title compound (0.01 g).

$^1$H NMR (300 MHz, CDCl$_3$) δ 1.67-1.82 (1H, m), 2.05-2.20 (2H, m), 2.31 (3H, s), 2.51 (3H, s), 3.48 (1H, td, J=11.7, 2.4 Hz), 3.62-3.73 (1H, m), 3.92-4.17 (6H, m), 5.28-5.36 (2H, m), 7.05 (1H, d, J=7.9 Hz), 7.21-7.25 (1H, m), 7.65 (1H, s), 8.31 (1H, d, J=1.9 Hz).

Example 7

1,5-anhydro-2,4-dideoxy-2-(7,8-dimethyl-6-((6-methylpyridin-3-yl)methyl)-4-oxo-2H-1,3-benzoxazin-3(4H)-yl)-threo-pentitol Monohydrochloride (Optical Isomer)

A) 5-bromo-2-hydroxy-N-(trans-4-hydroxytetrahydro-2H-pyran-3-yl)-3,4-dimethylbenzamide To a mixture of 5-bromo-2-hydroxy-3,4-dimethylbenzoic acid (1.5 g), trans-3-aminotetrahydro-2H-pyran-4-ol (0.79 g), WSC hydrochloride (1.41 g), HOBt monohydrate (0.94 g) and DMF (10 mL) was added triethylamine (1.28 mL), and the mixture was stirred at room temperature for 2 days. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (1.26 g).

MS: [M+H]$^+$ 344.0, 346.0

B) 6-bromo-3-(trans-4-hydroxytetrahydro-2H-pyran-3-yl)-7,8-dimethyl-2H-benzo[e][1,3]oxazin-4(3H)-one To a mixture of 5-bromo-2-hydroxy-N-(trans-4-hydroxytetrahydro-2H-pyran-3-yl)-3,4-dimethylbenzamide (0.99 g), paraformaldehyde (0.43 g) and toluene (20 mL) was added p-toluenesulfonic acid monohydrate (0.16 g), and the mixture was stirred at 50° C. overnight. The reaction mixture was neutralized with saturated aqueous sodium hydrogen carbonate solution at 0° C., and extracted with ethyl acetate. The organic layer was washed with water and brine, dried over anhydrous magnesium sulfate and concentrated under reduced pressure. The resulting residue was collected by filtration, and washed with hexane to give the title compound (0.42 g).

MS: [M+H]$^+$ 356.1, 358.2

C) 6-((6-chloropyridin-3-yl)methyl)-3-(trans-4-hydroxytetrahydro-2H-pyran-3-yl)-7,8-dimethyl-2H-benzo[e][1,3]oxazin-4 (3H)-one To a mixture of 6-bromo-3-(trans-4-hydroxytetrahydro-2H-pyran-3-yl)-7,8-dimethyl-2H-benzo[e][1,3]oxazin-4 (3H)-one (0.38 g), bis(tri-tert-butylphosphine)palladium (0) (0.03 g) and THF (1 mL) was added (6-chloro-3-pyridyl) methylzinc chloride (0.5 M THF solution) (4.27 mL), and the mixture was stirred under an argon atmosphere at 80° C. for 3 hr. To the reaction mixture was added water, and the mixture was extracted with a mixed solution of ethyl acetate and THF. The organic layer was washed with water and brine, dried over anhydrous magnesium sulfate and concentrated under reduced pressure. The residue was purified by silica gel column chromatography (ethyl acetate/hexane) to give the title compound (0.37 g).

MS: [M+H]$^+$ 403.2

D) 3-(trans-4-hydroxytetrahydro-2H-pyran-3-yl)-7,8-dimethyl-6-((6-methylpyridin-3-yl)methyl)-2H-benzo[e][1,3]oxazin-4(3H)-one To a mixture of 6-((6-chloropyridin-3-yl)methyl)-3-(trans-4-hydroxytetrahydro-2H-pyran-3-yl)-7,8-dimethyl-2H-benzo[e][1,3]oxazin-4 (3H)-one (0.20 g), 1,1'-bis(diphenylphosphino)ferrocene palladium (II) chloride dichloromethane complex (0.02 g) and THF (2 mL) was added methylzinc chloride (2 M THF solution) (0.75 mL), and the mixture was stirred under an argon atmosphere at 80° C. overnight. To the reaction mixture was added water at room temperature, and the mixture was extracted with a mixed solution of ethyl acetate and THF. The organic layer was washed with water and brine, dried over anhydrous magnesium sulfate and concentrated under reduced pressure. The residue was purified by NH silica gel column chromatography (ethyl acetate/hexane) to give the title compound (0.11 g).

MS: [M+H]$^+$ 383.2

E) 1,5-anhydro-2,4-dideoxy-2-(7,8-dimethyl-6-((6-methylpyridin-3-yl)methyl)-4-oxo-2H-1,3-benzoxazin-3(4H)-yl)-threo-pentitol Hydrochloride (Optical Isomer)

3-(trans-4-Hydroxytetrahydro-2H-pyran-3-yl)-7,8-dimethyl-6-((6-methylpyridin-3-yl)methyl)-2H-benzo[e][1,3] oxazin-4 (3H)-one (0.10 g) was optically resolved by HPLC (Chiral PAK AD, 50 mm ID×500 mm L, mobile phase: ethanol/hexane=80/20) to give a product with a longer retention time (0.05 g). To a mixture of the obtained crude product and ethyl acetate (1 mL) was added 4N hydrogen chloride (ethyl acetate solution) (0.03 mL), and the mixture was stirred for 10 min. The resulting solid was collected by filtration, washed with ethyl acetate, and dried under reduced pressure to give the title compound (0.04 g).

$^1$H NMR (300 MHz, DMSO-d$_6$) δ 1.38-1.63 (1H, m), 1.86-1.96 (1H, m), 2.12 (3H, s), 2.16 (3H, s), 2.68 (3H, s), 3.27-3.39 (1H, m), 3.45 (1H, t, J=10.7 Hz), 3.69 (1H, dd, J=11.0, 4.2 Hz), 3.76-3.99 (4H, m), 4.18 (2H, s), 5.22-5.39 (2H, m), 7.53 (1H, s), 7.78 (1H, d, J=8.3 Hz), 8.07-8.15 (1H, m), 8.61 (1H, d, J=1.9 Hz). The peak of one proton was not observed.

Example 8

6-((6-chloropyridin-3-yl)methyl)-3-((1S,2S)-2-hydroxycyclopentyl)-7,8-dimethyl-2,3-dihydro-4H-1,3-benzoxazin-4-one A) 5-bromo-2-hydroxy-N-((1S,2S)-2-hydroxycyclopentyl)-3,4-dimethylbenzamide A mixture of 5-bromo-2-hydroxy-3,4-dimethylbenzoic acid (0.52 g), (1S,2S)-2-aminocyclopentanol hydrochloride (0.32 g), HATU (0.97 g), triethylamine (1.48 mL) and DMF (6 mL) was stirred at room temperature overnight, and at 80° C. for 5 hr. To the reaction mixture was added water, and the mixture was extracted with ethyl acetate. The organic layer was washed with brine, dried over anhydrous sodium sulfate, and concentrated under reduced pressure. The residue was purified by silica gel column chromatography (ethyl acetate/hexane) to give the title compound (0.18 g).

MS: [M+H]$^+$ 328.0, 330.0

B) 6-bromo-3-((1S,2S)-2-hydroxycyclopentyl)-7,8-dimethyl-2H-benzo[e][1,3]oxazin-4(3H)-one A mixture of 5-bromo-2-hydroxy-N-((1S,2S)-2-hydroxycyclopentyl)-3,4-dimethylbenzamide (0.18 g), paraformaldehyde (0.08 g), p-toluenesulfonic acid monohydrate (0.05 g) and toluene (3 mL) was stirred under an argon atmosphere at 50° C. for 2 hr. The reaction solvent was evaporated under reduced pressure, and the residue was purified by silica gel column chromatography (ethyl acetate/hexane) to give the title compound (0.06 g).

MS: [M+H]$^+$ 340.0, 342.0

C) 6-((6-chloropyridin-3-yl)methyl)-3-((1S,2S)-2-hydroxycyclopentyl)-7,8-dimethyl-2,3-dihydro-4H-1,3-benzoxazin-4-one To a mixture of 6-bromo-3-((1S,2S)-2-hydroxycyclopentyl)-7,8-dimethyl-2H-benzo[e][1,3]oxazin-4(3H)-one (0.06 g), bis(tri-tert-butylphosphine)palladium (0) (0.01 g) and THF (2 mL) was added ((6-chloropyridin-3-yl)methyl)zinc (II) chloride (0.5 M THF solution) (0.84 mL), and the mixture was stirred under an argon atmosphere at room temperature overnight. The reaction mixture was diluted with ethyl acetate, washed with water and brine, dried over anhydrous sodium sulfate, and concentrated under reduced pressure. The residue was purified by silica gel column chromatography (ethyl acetate/hexane) to give the title compound (0.05 g).

$^1$H NMR (300 MHz, DMSO-d$_6$) δ 1.38-1.52 (1H, m), 1.53-1.73 (3H, m), 1.74-1.94 (2H, m), 2.13 (6H, d, J=8.9 Hz), 4.11 (3H, brs), 4.34 (1H, q, J=8.7 Hz), 4.87 (1H, d, J=5.3 Hz), 5.15-5.32 (2H, m), 7.33-7.49 (2H, m), 7.53 (1H, dd, J=8.3, 2.5 Hz), 8.25 (1H, d, J=1.9 Hz).

Example 9

8-fluoro-3-((1S,2S)-2-hydroxycyclopentyl)-7-methyl-6-(4-(1-methyl-1H-pyrazol-3-yl)benzyl)-2,3-dihydro-4H-1,3-benzoxazin-4-one A) 3-(4-(chloromethyl)phenyl)-1-methyl-1H-pyrazole Hydrochloride A mixture of (4-(1-methyl-1H-pyrazol-3-yl)phenyl) methanol (1.21 g) and thionyl chloride (3 mL) was stirred at 60° C. for 10 min. The reaction mixture was allowed to cool to room temperature, and diluted with ethyl acetate. The resulting precipitates were collected by filtration, washed with ethyl acetate, and dried under reduced pressure to give the title compound (1.43 g).

MS: [M+H]$^+$ 206.9

B) 8-fluoro-3-((1S,2S)-2-hydroxycyclopentyl)-7-methyl-6-(4-(1-methyl-1H-pyrazol-3-yl)benzyl)-2,3-dihydro-4H-1,3-benzoxazin-4-one A mixture of 8-fluoro-3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one (1.0 g), 2 M aqueous sodium carbonate solution (3.83 mL), 3-(4-(chloromethyl)phenyl)-1-methyl-1H-pyrazole hydrochloride (0.85 g), tetrakis(triphenylphosphine)palladium (0) (0.30 g) and DME (10 mL) was stirred under an argon atmosphere at 90° C. for 2 hr. The reaction mixture was diluted with ethyl acetate, and the organic layer was washed with brine, dried over anhydrous sodium sulfate, and concentrated under reduced pressure. The residue was purified by silica gel column chromatography (ethyl acetate/hexane) and solidified with ethyl acetate and diisopropyl ether to give the title compound (0.71 g).

$^1$H NMR (300 MHz, DMSO-d$_6$) δ 1.34-1.53 (1H, m), 1.54-1.73 (3H, m), 1.74-1.94 (2H, m), 2.18 (3H, d, J=2.5 Hz), 3.86 (3H, s), 3.96-4.14 (3H, m), 4.35 (1H, q, J=8.7 Hz), 4.90 (1H, d, J=5.1 Hz), 5.25-5.42 (2H, m), 6.62 (1H, d, J=2.3 Hz), 7.15 (2H, d, J=8.3 Hz), 7.42 (1H, s), 7.62-7.76 (3H, m).

Example 10

1,5-anhydro-2-(6-((6-chloropyridin-3-yl)methyl)-7,8-dimethyl-4-oxo-2H-1,3-benzoxazin-3(4H)-yl)-2,4-dideoxy-L-threo-pentitol A) 5-bromo-2-hydroxy-N-((3S,4S)-4-hydroxytetrahydro-2H-pyran-3-yl)-3,4-dimethylbenzamide To a mixture of 5-bromo-2hydroxy-3,4-dimethylbenzoic acid (2.50 g), (3S,4S)-3-aminotetrahydro-2H-pyran-4-ol (1.20 g), triethylamine (2.84 mL) and DMF (10 mL) was added HATU (5.82 g), and the mixture was stirred at room temperature overnight. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (1.80 g).

MS: [M+H]$^+$ 344.1, 345.9

B) 6-bromo-3-((3S,4S)-4-hydroxytetrahydro-2H-pyran-3-yl)-7,8-dimethyl-2H-benzo[e][1,3]oxazin-4(3H)-one To a mixture of 5-bromo-2-hydroxy-N-((3S,4S)-4-hydroxytetrahydro-2H-pyran-3-yl)-3,4-dimethylbenzamide (1.80 g), paraformaldehyde (0.47 g) and toluene (20 mL) was added p-toluenesulfonic acid monohydrate (0.20 g), and the mixture was stirred at 50° C. overnight. The reaction mixture was neutralized with saturated aqueous sodium hydrogen carbonate solution at 0° C., and extracted with ethyl acetate. The organic layer was washed with water and brine, dried over anhydrous magnesium sulfate and concentrated under reduced pressure. The residue was collected by filtration, and washed with hexane to give the title compound (1.52 g).

MS: [M+H]$^+$ 356.1, 358.1

C) 1,5-anhydro-2-(6-((6-chloropyridin-3-yl)methyl)-7,8-dimethyl-4-oxo-2H-1,3-benzoxazin-3(4H)-yl)-2,4-dideoxy-L-threo-pentitol To a mixture of 6-bromo-3-((3S,4S)-4-hydroxytetrahydro-2H-pyran-3-yl)-7,8-dimethyl-2H-benzo[e][1,3]oxazin-4(3H)-one (0.40 g), bis(tri-tert-butylphosphine)palladium (0) (0.029 g) and THF (1 mL) was added (6-chloro-3-pyridyl)methylzinc chloride (0.5 M THF solution) (4.49 mL), and the mixture was stirred under an argon atmosphere at 80° C. overnight. To the reaction mixture was added water, and the mixture was extracted with a mixed solution of ethyl acetate and THF. The organic layer was washed with water and brine, dried over anhydrous magnesium sulfate and concentrated under reduced pressure. The residue was purified by silica gel column chromatography (ethyl acetate/hexane) and crystallized from ethanol to give the title compound (0.13 g). In addition, as the second crystal, the title compound (0.08 g) was obtained.

$^1$H NMR (300 MHz, CDCl$_3$) δ 1.67-1.83 (1H, m), 2.03-2.10 (1H, m), 2.13 (3H, s), 2.15 (3H, s), 3.48 (1H, td, J=11.7, 2.4 Hz), 3.58-3.76 (2H, m), 3.93-4.05 (5H, m), 4.06-4.23 (1H, m), 5.18-5.28 (2H, m), 7.17-7.23 (1H, m), 7.29-7.37 (1H, m), 7.61 (1H, s), 8.20 (1H, d, J=2.1 Hz).

Example 11

3-((1S,2S)-2-hydroxycyclopentyl)-7,8-dimethyl-6-((6-methylpyridin-3-yl)methyl)-2,3-dihydro-4H-1,3-benzoxazin-4-one To a mixture of 6-((6-chloropyridin-3-yl)methyl)-3-((1S,2S)-2-hydroxycyclopentyl)-7,8-dimethyl-2H-benzo[e][1,3]oxazin-4(3H)-one (0.05 g), 1,1'-bis(diphenylphosphino)ferrocene palladium (II) chloride dichloromethane complex (0.005 g) and THF (2 mL) was added methylzinc chloride (2 M THF solution) (0.18 mL), and the mixture was stirred under an argon atmosphere at 80° C. overnight. To the reaction mixture was added water, and the mixture was extracted with ethyl acetate. The organic layer was washed with water and brine, dried over anhydrous sodium sulfate, and concentrated under reduced pressure. The residue was purified by NH silica gel column chromatography (ethyl acetate/hexane) to give the title compound (0.02 g).

$^1$H NMR (300 MHz, DMSO-d$_6$) δ 1.34-1.53 (1H, m), 1.55-1.71 (3H, m), 1.73-1.95 (2H, m), 2.11 (3H, s), 2.15 (3H, s), 2.41 (3H, s), 3.97 (2H, s), 4.01-4.14 (1H, m), 4.34 (1H, q, J=8.7 Hz), 4.87 (1H, d, J=5.1 Hz), 5.14-5.29 (2H, m), 7.15 (1H, d, J=8.1 Hz), 7.34 (1H, dd, J=7.9, 2.3 Hz), 7.43 (1H, s), 8.27 (1H, d, J=1.7 Hz).

Example 12

4-((8-fluoro-3-((1S,2S)-2-hydroxycyclopentyl)-7-methyl-4-oxo-3,4-dihydro-2H-1,3-benzoxazin-6-yl)methyl)benzonitrile To a mixture of 8-fluoro-3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one (0.18 g), 2 M aqueous sodium carbonate solution (0.47 mL), 4-(bromomethyl)benzonitrile (0.10 g) and DME (4 mL) was added 1,1'-bis (diphenylphosphino)ferrocene palladium (II) chloride dichloromethane complex (0.02 g) under an argon atmosphere and the mixture was stirred at 80° C. overnight. The reaction mixture was diluted with ethyl acetate, and the organic layer was washed with brine, dried over anhydrous sodium sulfate and concentrated under reduced pressure. The residue was purified by silica gel column chromatography (ethyl acetate/hexane) and solidified with ethyl acetate, diisopropyl ether and hexane to give the title compound (0.09 g).

$^1$H NMR (300 MHz, DMSO-d$_6$) δ 1.36-1.73 (4H, m), 1.74-1.94 (2H, m), 2.14 (3H, d, J=2.5 Hz), 3.99-4.17 (3H, m), 4.27-4.44 (1H, m), 4.91 (1H, d, J=5.1 Hz), 5.26-5.43 (2H, m), 7.34 (2H, d, J=8.1 Hz), 7.44 (1H, s), 7.77 (2H, d, J=8.3 Hz).

Example 13

8-fluoro-3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one To a mixture of 8-fluoro-3-((1S,2S)-2-hydroxycyclopentyl)-7-methyl-6-(4,4,5,5-tetramethyl-, 3,2-dioxaborolan-2-yl)-2H-benzo[e][1,3]oxazin-4 (3H)-one (0.10 g), sodium carbonate (0.05 g), 5-(bromomethyl)-2-(1H-pyrazol-1-yl)pyridine (0.06 g), DME (1 mL) and water (0.33 mL) was added under an argon atmosphere tetrakis(triphenylphosphine)palladium (0) (0.01 g) and the mixture was stirred at 85° C. for 1 hr. The reaction mixture was diluted with ethyl acetate, dried over anhydrous sodium sulfate and concentrated under reduced pressure. The residue was purified by silica gel column chromatography (ethyl acetate/hexane) and crystallized from ethyl acetate and hexane to give the title compound (0.07 g).

$^1$H NMR (300 MHz, CDCl$_3$) δ 1.61-1.95 (4H, m), 1.99-2.13 (2H, m), 2.20 (3H, d, J=2.5 Hz), 2.92 (1H, d, J=2.5 Hz), 4.00 (2H, s), 4.15-4.27 (1H, m), 4.31-4.44 (1H, m), 5.18-5.29 (2H, m), 6.45 (1H, dd, J=2.5, 1.7 Hz), 7.51 (1H, dd, J=8.5, 2.4 Hz), 7.58 (1H, s), 7.72 (1H, d, J=1.0 Hz), 7.89 (1H, d, J=8.6 Hz), 8.20 (1H, d, J=1.8 Hz), 8.52 (1H, d, J=2.5 Hz).

Example 14

3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one A) 5-bromo-2-hydroxy-N-((1S,2S)-2-hydroxycyclopentyl)-4-methylbenzamide To a suspension of 5-bromo-2-hydroxy-4-methylbenzoic acid (3.06 g) in THF (30 mL) was added dropwise oxalyl chloride (1.74 mL) at 0° C. To the reaction mixture was added one drop of DMF, and the mixture was stirred at 16° C. for 1.5 hr. The reaction mixture was concentrated under reduced pressure, and THF (15 mL) was added to the residue. To a mixture of (1S,2S)-2-aminocyclopentanol hydrochloride (1.82 g), triethylamine (9.23 mL), THF (15 mL) and methanol (10 mL) was added dropwise a mixture of the above-mentioned residue and THF at 0° C., and the mixture was stirred at room temperature for 2 hr. The reaction mixture was diluted with ethyl acetate, washed with brine, dried over anhydrous sodium sulfate, and concentrated under reduced pressure. The residue was purified twice by silica gel column chromatography (ethyl acetate/hexane) to give the title compound (2.38 g).

$^1$H NMR (300 MHz, DMSO-d$_6$) δ 1.38-1.57 (2H, m), 1.60-1.76 (2H, m), 1.78-1.92 (1H, m), 1.95-2.10 (1H, m), 2.30 (3H, s), 3.93-4.12 (2H, m), 4.82 (1H, d, J=4.3 Hz), 6.91 (1H, s), 8.15 (1H, s), 8.60 (1H, d, J=6.6 Hz), 12.75 (1H, s).

B) 6-bromo-3-((1S,2S)-2-hydroxycyclopentyl)-7-methyl-2H-benzo[e][1,3]oxazin-4 (3H)-one A mixture of 5-bromo-2-hydroxy-N-((1S,2S)-2-hydroxycyclopentyl)-4-methylbenzamide (1.56 g), paraformaldehyde (0.75 g), p-toluenesulfonic acid monohydrate (0.47 g) and toluene (20 mL) was heated under reflux for 2 hr. The reaction mixture was concentrated under reduced pressure, and the residue was purified by silica gel column chromatography (ethyl acetate/hexane) to give the title compound (0.27 g).

MS: [M+H]$^+$ 326.0, 328.0

C) 3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one A mixture of 6-bromo-3-((1S,2S)-2-hydroxycyclopentyl)-7-methyl-2H-benzo[e][1,3]oxazin-4(3H)-one (0.10 g), potassium acetate (0.09 g), bis(pinacolato)diboron (0.09 g), dichlorobis(triphenylphosphine)palladium (II) (0.01 g) and toluene (3 mL) was stirred under an argon atmosphere at 100° C. overnight. The reaction mixture was diluted with ethyl acetate, and the organic layer was washed with brine, dried over anhydrous sodium sulfate and concentrated under reduced pressure. The residue was purified by silica gel column chromatography (ethyl acetate/hexane) to give the title compound (0.11 g).

MS: [M+H]$^+$ 374.2

D) 3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one A mixture of 3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one (0.08 g), sodium carbonate (0.05 g), 5-(bromomethyl)-2-(1H-pyrazol-1-yl)pyridine (0.07 g), tetrakis(triphenylphosphine)palladium (0) (0.03 g), DME (3 mL) and water (1 mL) was stirred under an argon atmosphere at 90° C. overnight. The reaction mixture was diluted with ethyl acetate, washed with brine, dried over anhydrous sodium sulfate and concentrated under reduced pressure. The residue was purified by NH silica gel column chromatography (ethyl acetate/hexane) and solidified with ethyl acetate and hexane to give the title compound (0.06 g).

$^1$H NMR (300 MHz, DMSO-d$_6$) δ 1.38-1.52 (1H, m), 1.56-1.71 (3H, m), 1.75-1.91 (2H, m), 2.27 (3H, s), 3.98-4.10 (3H, m), 4.34 (1H, q, J=8.5 Hz), 4.87 (1H, d, J=5.1 Hz), 5.19-5.30 (2H, m), 6.56 (1H, dd, J=2.5, 1.7 Hz), 6.91 (1H, s), 7.57 (1H, s), 7.69 (1H, dd, J=8.5, 2.3 Hz), 7.79 (1H, d, J=1.1 Hz), 7.86 (1H, d, J=8.3 Hz), 8.32 (1H, d, J=1.9 Hz), 8.58 (1H, d, J=2.5 Hz).

Example 15

8-fluoro-3-(trans-2-hydroxycyclopentyl)-7-methoxy-6-((6-(1H-pyrazol-1-yl)pyridin-3-yl)methyl)-2,3-dihydro-4H-1,3-benzoxazin-4-one A) 2-fluoro-3-methoxyphenol To a mixture of (2-fluoro-3-methoxyphenyl)boronic acid (3.40 g) and THF (30 mL) was added dropwise hydrogen peroxide (30% aqueous solution, 10.0 mL), and the mixture was heated under reflux for 1 hr. Separately, to a mixture of (2-fluoro-3-methoxyphenyl)boronic acid (27.0 g) and THF (270 mL) was added dropwise hydrogen peroxide (30% aqueous solution, 90.0 mL), and the mixture was heated under reflux for 1 hr. The both batches were cooled to room temperature and combined, saturated aqueous sodium sulfite solution (100 mL) was added, and the mixture was extracted with ethyl acetate. The organic layer was dried over anhydrous sodium sulfate, concentrated under reduced pressure and the residue was purified by silica gel column chromatography (ethyl acetate/petroleum ether) to give the title compound (24.8 g).

$^1$H NMR (400 MHz, CDCl$_3$) δ 3.88 (3H, s), 5.23 (1H, brs), 6.53 (1H, t, J=8.4 Hz), 6.62 (1H, t, J=8.4 Hz), 6.93 (1H, td, J=8.4, 2.0 Hz).

B) 3-fluoro-2-hydroxy-4-methoxybenzaldehyde

To a mixture of 2-fluoro-3-methoxyphenol (22.0 g), triethylamine (93.9 g) and 1,2-dichloroethane (250 mL) was added magnesium chloride (71.7 g) and the mixture was stirred at 40° C. for 1 hr. To the reaction mixture was added paraformaldehyde (46.5 g) and the mixture was stirred at 40° C. for 16 hr. The reaction mixture was cooled to room temperature, 1N hydrochloric acid (500 mL) was added and the mixture was extracted with dichloromethane. The organic layer was dried over anhydrous sodium sulfate, concentrated under reduced pressure and the residue was purified by silica gel column chromatography (ethyl acetate/petroleum ether) to give the title compound (26.0 g).

$^1$H NMR (400 MHz, CDCl$_3$) δ 3.98 (3H, s), 6.64 (1H, dd, J=8.8, 6.8 Hz), 7.32 (1H, dd, J=8.8, 1.6 Hz), 9.77 (1H, d, J=2.0 Hz). The peak of one proton was not observed.

C) 3-fluoro-2-hydroxy-4-methoxybenzoic Acid

To a mixture of 3-fluoro-2-hydroxy-4-methoxybenzaldehyde (10.0 g), sodium dihydrogen phosphate (22.9 g), DMSO (100 mL) and water (25 mL) was added a mixture of sodium chlorite (14.5 g) and water (30 mL), and the mixture was stirred at 20° C. for 16 hr. DMSO was evaporated under reduced pressure, and the residue was diluted with water (100 mL) and extracted with ethyl acetate. The organic layer was washed with brine, dried over anhydrous sodium sulfate, and concentrated under reduced pressure to give the title compound (7.42 g).

$^1$H NMR (400 MHz, DMSO-d$_6$) δ 3.89 (3H, s), 6.75 (1H, t, J=8.4 Hz), 7.59 (1H, dd, J=9.2, 2.0 Hz). The peak of two protons was not observed.

D) 5-bromo-3-fluoro-2-hydroxy-4-methoxybenzoic Acid

To a mixture of 3-fluoro-2-hydroxy-4-methoxybenzoic acid (7.30 g) and DMF (70 mL) was added N-bromosuccinimide (7.00 g) and the mixture was stirred at 25° C. for 2 hr. DMF was evaporated under reduced pressure, and the residue was diluted with ethyl acetate, and washed with water brine. The organic layer was dried over anhydrous sodium sulfate, and concentrated under reduced pressure to give the title compound (8.86 g).

$^1$H NMR (400 MHz, DMSO-d$_6$) δ 4.00 (3H, s), 7.74 (1H, d, J=2.0 Hz). The peak of two protons was not observed.

E) 5-bromo-3-fluoro-2-hydroxy-N-(trans-2-hydroxycyclopentyl)-4-methoxybenzamide

A mixture of 5-bromo-3-fluoro-2-hydroxy-4-methoxybenzoic acid (2.90 g), trans-2-aminocyclopentanol hydrochloride (2.26 g), WSC hydrochloride (3.17 g), HOBt (2.23 g), triethylamine (4.44 g) and dichloromethane (100 mL) was stirred at 29° C. for 16 hr. The reaction mixture was diluted with dichloromethane (100 mL) and washed with brine (200 mL). The organic layer was dried over anhydrous sodium sulfate, concentrated under reduced pressure and the residue was purified by silica gel column chromatography (ethyl acetate/petroleum ether) to give the title compound (1.90 g).

$^1$H NMR (400 MHz, CDCl$_3$) δ 1.50-1.93 (4H, m), 2.01-2.13 (1H, m), 2.20-2.32 (1H, m), 3.66 (1H, brs), 3.95-4.18 (5H, m), 6.40 (1H, brs), 7.37 (1H, s), 12.25 (1H, brs).

F) 6-bromo-8-fluoro-3-(trans-2-hydroxycyclopentyl)-7-methoxy-2H-benzo[e][1,3]oxazin-4 (3H)-one A mixture of 5-bromo-3-fluoro-2-hydroxy-N-(trans-2-hydroxycyclopentyl)-4-methoxybenzamide (1.00 g), formaldehyde (37% aqueous solution, 10 mL) and formic acid (10 mL) was stirred at 50° C. for 16 hr. This reaction was performed in parallel in two batches. After cooling to room temperature, the reaction mixtures in both batches were poured into saturated sodium hydrogen carbonate solution (400 mL), and the mixtures were extracted with ethyl acetate. The organic layer was dried over anhydrous sodium sulfate, concentrated under reduced pressure and the residue was purified by silica gel column chromatography (ethyl acetate/petroleum ether) to give the title compound (0.95 g).

$^1$H NMR (400 MHz, CDCl$_3$) δ 1.62-1.95 (4H, m), 2.00-2.17 (2H, m), 3.19 (1H, brs), 4.09 (3H, d, J=2.4 Hz), 4.14-4.25 (1H, m), 4.41 (1H, q, J=8.4 Hz), 5.28 (2H, s), 7.92 (1H, d, J=1.6 Hz).

G) 8-fluoro-3-(trans-2-hydroxycyclopentyl)-7-methoxy-6-(4,4,5,5-tetramethyl-1,3,2-dioxaborolan-2-yl)-2H-benzo[e][1,3]oxazin-4 (3H)-one A mixture of 6-bromo-8-fluoro-3-(trans-2-hydroxycyclopentyl)-7-methoxy-2H-benzo[e][1,3]oxazin-4(3H)-one (0.75 g), bis(pinacolato)diboron (0.58 g), 1,1'-bis(diphenylphosphino)ferrocene palladium (II) chloride dichloromethane complex (0.17 g), potassium acetate (0.59 g) and 1,4-dioxane (10 mL) was stirred under a nitrogen atmosphere at 80° C. for 16 hr. The reaction mixture was cooled to room temperature, filtered, and the filtrate was concentrated under reduced pressure. The residue was diluted with ethyl acetate, and the organic layer was washed with brine, dried over anhydrous sodium sulfate and concentrated under reduced pressure. The residue was purified by silica gel column chromatography (ethyl acetate/petroleum ether) to give the title compound (0.27 g).

$^1$H NMR (400 MHz, CDCl$_3$) δ 1.34 (12H, s), 1.70-1.92 (4H, m), 1.95-2.15 (2H, m), 3.31 (1H, brs), 4.01 (3H, d, J=2.0 Hz), 4.20 (1H, q, J=6.8 Hz), 4.34 (1H, q, J=8.0 Hz), 5.17-5.32 (2H, m), 8.09 (1H, s).

H) 8-fluoro-3-(trans-2-hydroxycyclopentyl)-7-methoxy-6-((6-(1H-pyrazol-1-yl)pyridin-3-yl)methyl)-2,3-dihydro-4H-1,3-benzoxazin-4-one To a mixture of 8-fluoro-3-(trans-2-hydroxycyclopentyl)-7-methoxy-6-(4,4,5,5-tetramethyl-1,3,2-dioxaborolan-2-yl)-2H-benzo[e][1,3]oxazin-4(3H)-one (0.15 g), DME (9 mL) and water (3 mL) were added sodium carbonate (0.39 g), 5-(bromomethyl)-2-(1H-pyrazol-1-yl)pyridine (0.18 g) and tetrakis(triphenylphosphine)palladium (0) (0.02 g), and the mixture immediately heated to 85° C. in an oil bath heated in advance and stirred at the same temperature under a nitrogen atmosphere for 15 min. The reaction mixture was cooled to room temperature and ethyl acetate and brine were added. The organic layer was separated, the aqueous layer was further extracted with ethyl acetate, and the mixed organic layer was dried over anhydrous sodium sulfate and concentrated under reduced pressure. The residue was purified by HPLC (C18, mobile phase:water/acetonitrile (containing 0.1% ammonium hydrogen carbonate)) and supercritical fluid chromatography (column: CHIRALCEL OJ-3 (trade name), 4.6 mm ID×50 mm L, mobile phase:ethanol/carbon dioxide=5%-40%). The solvent was evaporated under reduced pressure, acetonitrile (5 mL) and water (30 mL) were added to the residue, and the mixture was lyophilized to give the title compound (0.05 g).

$^1$H NMR (400 MHz, DMSO-$d_6$) δ 1.35-1.70 (4H, m), 1.72-1.92 (2H, m), 3.91 (3H, s), 4.01 (2H, s), 4.02-4.10 (1H, m), 4.35 (1H, q, J=8.4 Hz), 4.91 (1H, d, J=4.8 Hz), 5.30-5.42 (2H, m), 6.56 (1H, s), 7.54 (1H, s), 7.72-7.82 (2H, m), 7.82-7.88 (1H, m), 8.37 (1H, s), 8.58 (1H, d, J=2.4 Hz).

Example 16

6-((6-chloropyridin-3-yl)methyl)-8-fluoro-3-((1S,2S)-2-hydroxycyclopentyl)-7-methyl-2,3-dihydro-4H-1,3-benzoxazin-4-one To a mixture of 6-bromo-8-fluoro-3-((1S,2S)-2-hydroxycyclopentyl)-7-methyl-2H-benzo[e][1,3]oxazin-4(3H)-one (0.50 g), bis(tri-tert-butylphosphine)palladium (0) (0.04 g) and THF (1 mL) was added (6-chloro-3-pyridyl)methylzinc chloride (0.5 M THF solution) (4.36 mL), and the mixture was stirred under an argon atmosphere at 80° C. overnight. To the reaction mixture was added water, and the mixture was extracted with a mixed solution of ethyl acetate and THF. The organic layer was washed with water and brine, dried over anhydrous magnesium sulfate and concentrated under reduced pressure. The residue was purified by silica gel column chromatography (ethyl acetate/hexane), and crystallized from ethyl acetate to give the title compound (0.31 g).

$^1$H NMR (300 MHz, CDCl$_3$) δ 1.62-1.87 (4H, m), 1.99-2.12 (2H, m), 2.17 (3H, d, J=2.5 Hz), 2.88 (1H, d, J=3.8 Hz), 3.95 (2H, s), 4.15-4.29 (1H, m), 4.30-4.49 (1H, m), 5.24 (2H, d, J=1.9 Hz), 7.19-7.25 (1H, m), 7.31-7.39 (1H, m), 7.53 (1H, d, J=1.3 Hz), 8.21 (1H, d, J=2.1 Hz).

Example 17

1,5-anhydro-2,4-dideoxy-2-(6-(4-methoxybenzyl)-7,8-dimethyl-4-oxo-2H-1,3-benzoxazin-3(4H)-yl)-threo-pentitol (Optical Isomer)

A) 3-(trans-4-hydroxytetrahydro-2H-pyran-3-yl)-6-(4-methoxybenzyl)-7,8-dimethyl-2H-benzo[e][1,3]oxazin-4 (3H)-one To a mixture of 6-bromo-3-(trans-4-hydroxytetrahydro-2H-pyran-3-yl)-7,8-dimethyl-2H-benzo[e][1,3]oxazin-4 (3H)-one (0.16 g), bis(tri-tert-butylphosphine)palladium (0) (0.01 g) and THF (1 mL) was added 4-methoxybenzylzinc chloride (0.5 M THF solution) (1.80 mL), and the mixture was stirred under an argon atmosphere at 80° C. for 3 hr. To the reaction mixture was added water, and the mixture was extracted with a mixed solution of ethyl acetate and THF. The organic layer was washed with water and brine, dried over anhydrous magnesium sulfate and concentrated under reduced pressure. The residue was purified by silica gel column chromatography (ethyl acetate/hexane), and crystallized from ethyl acetate to give the title compound (0.13 g). MS: [M+H]$^+$ 398.2

B) 1,5-anhydro-2,4-dideoxy-2-(6-(4-methoxybenzyl)-7,8-dimethyl-4-oxo-2H-1,3-benzoxazin-3(4H)-yl)-threo-pentitol (Optical Isomer)

3-(trans-4-Hydroxytetrahydro-2H-pyran-3-yl)-6-(4-methoxybenzyl)-7,8-dimethyl-2H-benzo[e][1,3]oxazin-4 (3H)-one (0.12 g) was optically resolved by HPLC (Chiral PAK IA, 50 mm ID×500 mm L, mobile phase:ethanol/hexane=50/50), and a product with a longer retention time was solidified with ethyl acetate to give the title compound (0.05 g).

$^1$H NMR (300 MHz, CDCl$_3$) δ 1.66-1.83 (1H, m), 2.04-2.13 (1H, m), 2.15 (6H, d, J=1.1 Hz), 2.16-2.21 (1H, m), 3.40-3.55 (1H, m), 3.60-3.73 (1H, m), 3.77 (3H, s), 3.93 (2H, s), 3.95-4.05 (3H, m), 4.13 (1H, td, J=9.8, 4.9 Hz), 5.15-5.29 (2H, m), 6.80 (2H, d, J=8.7 Hz), 6.97-7.04 (2H, m), 7.60 (1H, s).

Example 18

8-fluoro-3-((1S,2S)-2-hydroxycyclopentyl)-6-((6-methoxypyridin-3-yl)methyl)-7-methyl-2,3-dihydro-4H-1,3-benzoxazin-4-one To a mixture of 8-fluoro-3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one (0.40 g), 5-(chloromethyl)-2-methoxypyridine (0.17 g), 1,1'-bis(diphenylphosphino)ferrocene palladium (II) chloride dichloromethane complex (0.04 g) and DME (10 mL) was added 2 M aqueous sodium carbonate solution (1.02 mL), and the mixture was stirred under an argon atmosphere at 80° C. overnight. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane), and crystallized from ethanol to give the title compound (0.07 g). In addition, as the second crystal, the title compound (0.02 g) was obtained.

$^1$H NMR (300 MHz, CDCl$_3$) δ 1.62-1.94 (4H, m), 1.97-2.14 (2H, m), 2.19 (3H, d, J=2.6 Hz), 2.98 (1H, d, J=3.8 Hz), 3.88 (2H, s), 3.91 (3H, s), 4.14-4.26 (1H, m), 4.30-4.44 (1H, m), 5.15-5.31 (2H, m), 6.66 (1H, d, J=8.5 Hz), 7.27-7.32 (1H, m), 7.52 (1H, s), 7.94 (1H, d, J=2.1 Hz).

Example 19

1,5-anhydro-2-(6-((6-chloropyridin-3-yl)methyl)-8-fluoro-7-methyl-4-oxo-2H-1,3-benzoxazin-3(4H)-yl)-2,4-dideoxy-L-threo-pentitol A) 5-bromo-3-fluoro-2-hydroxy-N-((3S,4S)-4-hydroxytetrahydro-2H-pyran-3-yl)-4-methylbenzamide To a mixture of 5-bromo-3-fluoro-2-hydroxy-4-methylbenzoic acid (1.50 g), (3S,4S)-3-aminotetrahydro-2H-pyran-4-ol (0.71 g), WSC hydrochloride (1.39 g), HOBt monohydrate (1.02 g) and DMF (10 mL) was added triethylamine (1.26 mL), and the mixture was stirred at room temperature for 2 days. To the reaction mixture was added water, and the mixture was washed with ethyl acetate. The aqueous layer was separated, 1N hydrochloric acid was added to acidify the mixture (pH 5), and the mixture was extracted with ethyl acetate. The organic layer was washed with brine, dried over anhydrous magnesium sulfate and concentrated under reduced pressure. The residue was purified by silica gel column chromatography (methanol/ethyl acetate) to give the title compound (0.43 g).

MS: [M+H]$^+$ 348.0, 350.0

B) 6-bromo-8-fluoro-3-((3S,4S)-4-hydroxytetrahydro-2H-pyran-3-yl)-7-methyl-2H-benzo [e][1,3] oxazin-4 (3H)-one To a mixture of 5-bromo-3-fluoro-2-hydroxy-N-((3S,4S)-4-hydroxytetrahydro-2H-pyran-3-yl)-4-methylbenzamide (0.43 g), paraformaldehyde (0.11 g) and toluene (5 mL) was added p-toluenesulfonic acid monohydrate (0.07 g), and the mixture was stirred at 50° C. overnight, and then at 100° C. overnight. The reaction mixture was neutralized with saturated aqueous sodium hydrogen carbonate solution at 0° C., and extracted with ethyl acetate. The organic layer was washed with water and brine, dried over anhydrous magnesium sulfate and concentrated under reduced pressure to give the title compound (0.30 g).

MS: [M+H]$^+$ 360.1, 362.2

C) 1,5-anhydro-2-(6-((6-chloropyridin-3-yl)methyl)-8-fluoro-7-methyl-4-oxo-2H-1,3-benzoxazin-3(4H)-yl)-2,4-dideoxy-L-threo-pentitol To a mixture of 6-bromo-8-fluoro-3-((3S,4S)-4-hydroxytetrahydro-2H-pyran-3-yl)-7-methyl-2H-benzo[e][1,3]oxazin-4(3H)-one (0.30 g), bis(tri-tert-butylphosphine) palladium (0) (0.02 g) and THF (1 mL) was added (6-chloro-3-pyridyl)methylzinc chloride (0.5 M THF solution) (3.33 mL), and the mixture was stirred under an argon atmosphere at 80° C. overnight. To the reaction mixture was added water, and the mixture was extracted with a mixed solution of ethyl acetate and THF. The organic layer was washed with water and brine, dried over anhydrous magnesium sulfate and concentrated under reduced pressure. The residue was purified by silica gel column chromatography (ethyl acetate/hexane) and crystallized from ethyl acetate to give the title compound (0.06 g). In addition, as the second crystal, the title compound (0.08 g) was obtained.

$^1$H NMR (300 MHz, DMSO-d$_6$) δ 1.41-1.61 (1H, m), 1.83-1.96 (1H, m), 2.17 (3H, d, J=2.6 Hz), 3.39-3.50 (1H, m), 3.56-3.64 (1H, m), 3.66-3.74 (1H, m), 3.78-3.97 (3H, m), 4.05 (2H, s), 5.09 (1H, d, J=5.3 Hz), 5.32-5.45 (2H, m), 7.38-7.47 (2H, m), 7.59 (1H, dd, J=8.2, 2.5 Hz), 8.28 (1H, d, J=2.1 Hz).

Example 20

8-fluoro-3-((1S,2S)-2-hydroxycyclopentyl)-7-methyl-6-((6-methylpyridin-3-yl)methyl)-2,3-dihydro-4H-1,3-benzoxazin-4-one To a mixture of tetramethyltin (IV) (0.26 mL), tetrakis (triphenylphosphine)palladium (0) (0.07 g) and DMF (2 mL) was added 6-((6-chloropyridin-3-yl)methyl)-8-fluoro-3-((1S,2S)-2-hydroxycyclopentyl)-7-methyl-2,3-dihydro-4H-1,3-benzoxazin-4-one (0.08 g), and the mixture was subjected to microwave irradiation at 150° C. for 40 min. The reaction mixture was diluted with ethyl acetate, and the organic layer was washed with brine, dried over anhydrous sodium sulfate, and concentrated under reduced pressure. The residue was purified by NH silica gel column chromatography (ethyl acetate/hexane) and solidified with ethyl acetate and hexane to give the title compound (0.03 g).

$^1$H NMR (300 MHz, DMSO-d$_6$) δ 1.37-1.55 (1H, m), 1.58-1.71 (3H, m), 1.78-1.92 (2H, m), 2.18 (3H, d, J=2.5 Hz), 2.42 (3H, s), 3.98 (2H, s), 4.01-4.11 (1H, m), 4.34 (1H, q, J=8.7 Hz), 4.90 (1H, d, J=5.1 Hz), 5.27-5.40 (2H, m), 7.17 (1H, d, J=7.9 Hz), 7.33-7.43 (2H, m), 8.29 (1H, d, J=1.9 Hz).

Example 21

6-((4,4-difluoropiperidin-1-yl)methyl)-3-((1S,2S)-2-hydroxycyclopentyl)-2,3-dihydro-4H-naphtho[2,1-e][1,3]oxazin-4-one A) 4-bromo-1-hydroxy-N-((1S,2S)-2-hydroxycyclopentyl)-2-naphthamide To a mixture of 4-bromo-1-hydroxy-2-naphthoic acid (5.00 g), (1S,2S)-2-aminocyclopentanol hydrochloride (2.71 g), HATU (9.25 g) and DMF (30 mL) was added triethylamine (7.83 mL) at 0° C., and the mixture was stirred at room temperature overnight. To the reaction mixture was added water, and the mixture was extracted with a mixed solvent of ethyl acetate and THF. The organic layer was washed with water and brine, dried over anhydrous magnesium sulfate and concentrated under reduced pressure. The residue was purified by silica gel column chromatography (ethyl acetate/hexane) to give the title compound (1.69 g).

MS: [M−H]$^-$ 347.9, 349.9

B) 6-bromo-3-((1S,2S)-2-hydroxycyclopentyl)-2H-naphtho[2,1-e][1,3]oxazin-4(3H)-one To a mixture of 4-bromo-1-hydroxy-N-((1S,2S)-2-hydroxycyclopentyl)-2-naphthamide (1.69 g) and formic acid (12 mL) was added formaldehyde (37% aqueous solution) (6 mL), and the mixture was stirred at 80° C. overnight. The reaction mixture was neutralized with saturated aqueous sodium hydroxide solution at 0° C., and the mixture was extracted with a mixed solution of ethyl acetate and THF. The organic layer was washed with water and brine, dried over anhydrous magnesium sulfate and concentrated under reduced pressure. The residue was purified by silica gel column chromatography (ethyl acetate/hexane) to give the title compound (0.50 g).

MS: [M+H]$^+$ 362.0, 364.0

C) 3-((1S,2S)-2-hydroxycyclopentyl)-6-vinyl-2H-naphtho[2,1-e][1,3]oxazin-4(3H)-one To a mixture of 6-bromo-3-((1S,2S)-2-hydroxycyclopentyl)-2H-naphtho[2,1-e][1,3]oxazin-4(3H)-one (1.13 g), 4,4,5,5-tetramethyl-2-vinyl-1,3,2-dioxaborolane (0.63 g), 2 M aqueous sodium carbonate solution (3.12 mL), DME (10 mL) and water (1 mL) was added 1,1'-bis(diphenylphosphino)ferrocene palladium (II) chloride dichloromethane complex (0.13 g), and the mixture was stirred at 80° C. overnight. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.93 g).

MS: [M+H]$^+$ 310.1

D) 3-((1S,2S)-2-hydroxycyclopentyl)-4-oxo-3,4-dihydro-2H-naphtho[2,1-e][1,3]oxazin-6-carbaldehyde To a mixture of 3-((1S,2S)-2-hydroxycyclopentyl)-6-vinyl-2H-naphtho[2,1-e][1,3]oxazin-4(3H)-one (0.93 g), osmium oxide (fixed catalyst I) (0.16 g), acetonitrile (5 mL), acetone (5 mL) and water (5 mL) was added sodium periodate (2.57 g) and the mixture was stirred at room temperature overnight. The insoluble material was filtered off, the filtrate was poured into water, and the mixture was extracted with ethyl acetate. The organic layer was washed with water and brine, and dried over anhydrous magnesium sulfate. The solvent was evaporated under reduced pressure to give the title compound (0.75 g).

MS: [M+H]$^+$ 312.1

E) 6-((4,4-difluoropiperidin-1-yl)methyl)-3-((1S,2S)-2-hydroxycyclopentyl)-2,3-dihydro-4H-naphtho[2,1-e][1,3]oxazin-4-one A mixture of 3-((1S,2S)-2-hydroxycyclopentyl)-4-oxo-3,4-dihydro-2H-naphtho[2,1-e][1,3]oxazin-6-carbaldehyde (0.10 g), 4,4-difluoropiperidine hydrochloride (0.06 g), triethylamine (0.05 mL), THF (1.5 mL) and methanol (1.5 mL) was stirred at room temperature for 5 min. To the reaction mixture was added sodium triacetoxyborohydride (0.10 g), and the mixture was stirred at room temperature overnight. Sodium triacetoxyborohydride (0.10 g) was further added to the reaction mixture, and the mixture was stirred at room temperature for 1 hr. To the reaction mixture was added at room temperature saturated aqueous sodium hydrogen carbonate solution, and the mixture was extracted with ethyl acetate. The organic layer was washed with brine, and dried over anhydrous magnesium sulfate. The solvent was evaporated under reduced pressure. The residue was purified by NH silica gel column chromatography (ethyl acetate/hexane) and solidified with ethyl acetate and hexane to give the title compound (0.01 g).

$^1$H NMR (300 MHz, CDCl$_3$) δ 1.72-2.18 (11H, m), 2.61 (4H, t, J=5.1 Hz), 3.89 (2H, s), 4.18-4.52 (2H, m), 5.39 (2H, s), 7.52-7.70 (2H, m), 7.85 (1H, s), 8.21 (1H, d, J=8.1 Hz), 8.29 (1H, d, J=8.3 Hz).

Example 22

8-fluoro-3-((1S,2S)-2-hydroxycyclopentyl)-7-methyl-6-((6-(1-methyl-1H-pyrazol-3-yl)pyridin-3-yl)methyl)-2,3-dihydro-4H-1,3-benzoxazin-4-one To a mixture of 6-((6-chloropyridin-3-yl)methyl)-8-fluoro-3-((1S,2S)-2-hydroxycyclopentyl)-7-methyl-2,3-dihydro-4H-1,3-benzoxazin-4-one (0.12 g), 1-methyl-3-(4,4,5,5-tetramethyl-1,3,2-dioxaborolan-2-yl)-1H-pyrazole (0.09 g), 1,1'-bis(diphenylphosphino)ferrocene palladium (II) chloride dichloromethane complex (0.01 g) and DME (10 mL) was added 2 M aqueous sodium carbonate solution (0.31 mL), and the mixture was stirred under an argon atmosphere at 80° C. overnight. The reaction mixture was diluted with ethyl acetate, dried over anhydrous magnesium sulfate and concentrated under reduced pressure. The residue was purified by NH silica gel column chromatography (ethyl acetate/hexane) and solidified with ethanol to give the title compound (0.02 g). In addition, as the second crystal, the title compound (0.05 g) was obtained.

$^1$H NMR (300 MHz, CDCl$_3$) δ 1.63-1.93 (4H, m), 1.97-2.13 (2H, m), 2.18 (3H, d, J=2.5 Hz), 3.02 (1H, d, J=3.6 Hz), 3.97 (3H, s), 3.99 (2H, s), 4.23 (1H, dt, J=6.6, 3.2 Hz), 4.31-4.47 (1H, m), 5.24 (2H, d, J=1.7 Hz), 6.82 (1H, d, J=2.3 Hz), 7.34-7.48 (2H, m), 7.59 (1H, s), 7.80 (1H, d, J=8.3 Hz), 8.44 (1H, d, J=1.7 Hz).

Example 23

3-[(3S,4S)-4-hydroxytetrahydro-2H-pyran-3-yl]-7,8-dimethyl-6-[4-(1H-pyrazol-1-yl)benzyl]-2,3-dihydro-4H-1,3-benzoxazin-4-one Alias; 1,5-anhydro-2,4-dideoxy-2-(7,8-dimethyl-4-oxo-6-(4-(1H-pyrazol-1-yl)benzyl)-2H-1,3-benzoxazin-3(4H)-yl)-L-threo-pentitol

A) 3-((3S,4S)-4-hydroxytetrahydro-2H-pyran-3-yl)-7,8-dimethyl-6-(4,4,5,5-tetramethyl-1,3,2-dioxaborolan-2-yl)-2H-benzo[e][1,3]oxazin-4 (3H)-one To a mixture of 6-bromo-3-((3S,4S)-4-hydroxytetrahydro-2H-pyran-3-yl)-7,8-dimethyl-2H-benzo[e][1,3]oxazin-4 (3H)-one (1.10 g), bis(pinacolato)diboron (1.18 g), potassium acetate (0.61 g) and toluene (10 mL) was added dichlorobis(triphenylphosphine)palladium (II) (0.11 g), and the mixture was stirred under an argon atmosphere at 90° C. overnight. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.58 g).

MS: [M+H]$^+$ 404.2

B) 3-[(3S,4S)-4-hydroxytetrahydro-2H-pyran-3-yl]-7,8-dimethyl-6-[4-(1H-pyrazol-1-yl)benzyl]-2,3-dihydro-4H-1,3-benzoxazin-4-one Alias; 1,5-anhydro-2,4-dideoxy-2-(7,8-dimethyl-4-oxo-6-(4-(1H-pyrazol-1-yl)benzyl)-2H-1,3-benzoxazin-3(4H)-yl)-L-threo-pentitol To a mixture of 3-((3S,4S)-4-hydroxytetrahydro-2H-pyran-3-yl)-7,8-dimethyl-6-(4,4,5,5-tetramethyl-1,3,2-dioxaborolan-2-yl)-2H-benzo[e][1,3]oxazin-4 (3H)-one (0.19 g), 1-(4-(bromomethyl)phenyl)-1H-pyrazole (0.13 g), 1,1'-bis(diphenylphosphino)ferrocene palladium (II) chloride dichloromethane complex (0.02 g) and DME (3 mL) was added 2 M aqueous sodium carbonate solution (0.46 mL), and the mixture was stirred under an argon atmosphere at 80° C. overnight. The reaction mixture was diluted with ethyl acetate, dried over anhydrous magnesium sulfate and concentrated under reduced pressure. The residue was purified by silica gel column chromatography (ethyl acetate/hexane) and crystallized from ethyl acetate to give the title compound (0.08 g).

$^1$H NMR (300 MHz, CDCl$_3$) δ 1.64-1.85 (1H, m), 2.06-2.10 (1H, m), 2.11-2.13 (1H, m), 2.14-2.15 (3H, m), 2.16 (3H, s), 3.48 (1H, td, J=11.7, 2.3 Hz), 3.62-3.75 (1H, m), 3.92-4.06 (5H, m), 4.07-4.24 (1H, m), 5.24 (2H, d, J=2.1 Hz), 6.41-6.47 (1H, m), 7.17 (2H, d, J=8.5 Hz), 7.54-7.61 (2H, m), 7.65 (1H, s), 7.70 (1H, d, J=1.5 Hz), 7.87 (1H, d, J=2.3 Hz).

Example 24-1

8-chloro-6-((6-chloropyridin-3-yl)methyl)-3-((S,2S)-2-hydroxycyclopentyl)-7-methyl-2,3-dihydro-4H-1,3-benzoxazin-4-one

A) 5-bromo-3-chloro-2-hydroxy-4-methylbenzoic Acid

To a mixture of methyl 5-bromo-3-chloro-2-hydroxy-4-methylbenzoate (10 g) and THF (200 mL) was added 4 M aqueous lithium hydroxide solution (18.8 mL) at room temperature, and the mixture was stirred at the same temperature overnight. To the reaction mixture was added 2 M hydrochloric acid (39.4 mL) at 0° C. The mixture was poured into water at room temperature, and extracted with ethyl acetate. The organic layer was separated, washed with water and brine, dried over anhydrous magnesium sulfate, and concentrated under reduced pressure to give the title compound (9.50 g). The obtained resultant product was used in the next step without further purification.

MS: [M−H]⁻ 262.9, 264.8

B) 2-(benzoyloxy)-5-bromo-3-chloro-4-methylbenzoic Acid

To a mixture of 5-bromo-3-chloro-2-hydroxy-4-methylbenzoic acid (9.5 g) and DMA (200 mL) was added benzoyl chloride (5.39 mL) at 0° C., and the mixture was stirred at room temperature overnight. To the reaction mixture were added ethyl acetate and water at room temperature. The organic layer was separated, and the aqueous layer was extracted with ethyl acetate. The combined organic layer was washed with water and brine, dried over anhydrous magnesium sulfate, and concentrated under reduced pressure to give the title compound (13.2 g). The obtained resultant product was used in the next step without further purification.

MS: [M−H]⁻ 366.9, 368.9

C) 4-bromo-2-chloro-6-(((1S,2S)-2-hydroxycyclopentyl)carbamoyl)-3-methylphenyl Benzoate To a mixture of 2-(benzoyloxy)-5-bromo-3-chloro-4-methylbenzoic acid (13.2 g), (1S,2S)-2-aminocyclopentanol hydrochloride (4.93 g), triethylamine (16.5 mL), and DMF (250 mL) was added HATU (15.0 g) at 0° C., and the mixture was stirred at room temperature for 4 hr. To the reaction mixture were added ethyl acetate and water at 0° C. The organic layer was separated, and the aqueous layer was extracted with ethyl acetate. The combined organic layer was washed with water and brine, dried over anhydrous magnesium sulfate, and concentrated under reduced pressure. The residue was purified by silica gel column chromatography (ethyl acetate/hexane) to give the title compound (3.36 g).

MS: [M+H]⁺ 452.0, 454.0

D) 5-bromo-3-chloro-2-hydroxy-N-((1S,2S)-2-hydroxycyclopentyl)-4-methylbenzamide To a mixture of 4-bromo-2-chloro-6-(((1S,2S)-2-hydroxycyclopentyl)carbamoyl)-3-methylphenyl benzoate (3.36 g), THF (60 mL), and methanol (12 mL) was added 4 M aqueous lithium hydroxide solution (2.04 mL) at room temperature, and the mixture was stirred at the same temperature overnight. To the reaction mixture was added 4 M aqueous lithium hydroxide solution (0.93 mL) at room temperature, and the mixture was stirred at the same temperature for 5 hr. To the reaction mixture was added 4 M aqueous lithium hydroxide solution (0.19 mL) at room temperature, and the mixture was stirred at the same temperature overnight. To the reaction mixture was added 2 N hydrochloric acid to adjust pH to 2-3, and ethyl acetate and water were added. The organic layer was separated, and the aqueous layer was extracted with ethyl acetate. The combined organic layer was washed with water and brine, dried over anhydrous magnesium sulfate, and concentrated under reduced pressure to give the title compound (2.59 g). The obtained resultant product was used in the next step without further purification.

MS: [M+H]⁺ 348.0, 350.0

E) 6-bromo-8-chloro-3-((1S,2S)-2-hydroxycyclopentyl)-7-methyl-2H-benzo[e][1,3]oxazin-4(3H)-one To a mixture of 5-bromo-3-chloro-2-hydroxy-N-((1S,2S)-2-hydroxycyclopentyl)-4-methylbenzamide (2.59 g), paraformaldehyde (0.67 g), and toluene (50 mL) was added p-toluenesulfonic acid monohydrate (0.42 g) at room temperature, and the mixture was stirred at 100° C. for 2 hr. To the reaction mixture were added ethyl acetate and saturated aqueous sodium hydrogen carbonate solution at room temperature. The organic layer was separated, and the aqueous layer was extracted with ethyl acetate. The combined organic layer was washed with water and brine, dried over anhydrous magnesium sulfate, and concentrated under reduced pressure. The residue was purified by silica gel column chromatography (ethyl acetate/hexane) to give the title compound (0.61 g).

MS: [M+H]⁺ 360.0, 362.0

F) 8-chloro-6-((6-chloropyridin-3-yl)methyl)-3-((1S,2S)-2-hydroxycyclopentyl)-7-methyl-2,3-dihydro-4H-1,3-benzoxazin-4-one To a mixture of 6-bromo-8-chloro-3-((1S,2S)-2-hydroxycyclopentyl)-7-methyl-2H-benzo[e][1,3]oxazin-4 (3H)-one (0.61 g), bis(tri-tert-butylphosphine)palladium (0) (0.09 g), and THF (6 mL) was added ((6-chloropyridin-3-yl)methyl) zinc (II) chloride (0.5 M THF solution) (6.77 mL) under an argon atmosphere at room temperature, and the mixture was stirred at the same temperature for 2 hr under an argon atmosphere. To the reaction mixture were added ethyl acetate and water at room temperature. The organic layer was separated, and the aqueous layer was extracted with ethyl acetate. The combined organic layer was washed with water and brine, dried over anhydrous magnesium sulfate, and concentrated under reduced pressure. The residue was purified by silica gel column chromatography (ethyl acetate/hexane) to give the title compound (0.50 g).

¹H NMR (300 MHz, CDCl₃) δ 1.64-1.93 (4H, m), 1.99-2.15 (2H, m), 2.30 (3H, s), 2.92 (1H, d, J=3.8 Hz), 4.00 (2H, s), 4.17-4.28 (1H, m), 4.32-4.43 (1H, m), 5.22-5.33 (2H, m), 7.21-7.25 (1H, m), 7.30-7.35 (1H, m), 7.68 (1H, s), 8.21 (1H, d, J=1.9 Hz).

Example 24-2

8-chloro-6-((6-chloropyridin-3-yl)methyl)-3-((1S,2S)-2-hydroxycyclopentyl)-7-methyl-2,3-dihydro-4H-1,3-benzoxazin-4-one

A) 5-bromo-2-hydroxy-4-methylbenzoic Acid

To a mixture of 2-hydroxy-4-methylbenzoic acid (100 g) and acetic acid (1100 mL) was added dropwise bromine (34 mL) at room temperature, and the mixture was stirred at room temperature overnight. Water (800 mL) was added thereto, and the mixture was stirred at room temperature for 30 min. The precipitates were collected by filtration and washed with water to give the title compound (126 g).

MS: [M−H]⁻ 228.9, 230.9.

B) methyl 5-bromo-2-hydroxy-4-methylbenzoate

To a mixture of 5-bromo-2-hydroxy-4-methylbenzoic acid (126 g) and methanol (1000 mL) was added sulfuric acid (15 mL) at room temperature. The mixture was stirred at 55° C. overnight and refluxed for 10 hr. Sulfuric acid (15 mL) was added thereto. The mixture was stirred at 55° C. overnight, refluxed for 10 hr, stirred at 55° C. overnight, and refluxed for 10 hr in order. Sulfuric acid (15 mL) was added thereto, and the mixture was stirred at 55° C. overnight. After the mixture was allowed to be cooled to room temperature, methanol was removed by evaporation under reduced pressure. The residue was suspended in water (600 mL), and the mixture was stirred at room temperature for 30 min. The precipitates were collected by filtration to give the title compound (129 g).

$^1$H NMR (300 MHz, DMSO-$d_6$) δ 2.33 (3H, s), 3.87 (3H, s), 7.03 (1H, s), 7.87 (1H, s), 10.39 (1H, s).

C) Methyl 5-bromo-3-chloro-2-hydroxy-4-methylbenzoate

To a mixture of methyl 5-bromo-2-hydroxy-4-methylbenzoate (129 g) and DMF (1000 mL) was added N-chlorosuccinimide (74 g) at room temperature, and the mixture was stirred at room temperature overnight. N-Chlorosuccinimide (7.1 g) was added thereto, and the mixture was stirred at room temperature for 1.5 hr. After the mixture was allowed to be cooled to 0° C., water (800 mL) was added, and the mixture was stirred at room temperature for 1 hr. The precipitates were collected by filtration and washed with water to give the title compound (131 g).

MS: [M−H]⁻ 276.8, 278.8.

D) 5-bromo-3-chloro-2-hydroxy-N-((1S,2S)-2-hydroxycyclopentyl)-4-methylbenzamide A mixture of methyl 5-bromo-3-chloro-2-hydroxy-4-methylbenzoate (50 g), (1S,2S)-2-aminocyclopentanol hydrochloride (49 g), 1,8-diazabicyclo[5.4.0]undec-7-ene (81 mL), and DMA (350 mL) was stirred at 100° C. for 15 hr. 20% amount of the reaction mixture was poured into 0.1 N hydrochloric acid (1000 mL) at 00° C. The resulting mixture was stirred at room temperature for 3 hr. The precipitates were filtered, washed with water, and dried to give a crude product (12 g). 50% amount of the reaction mixture was poured into 0.1 N hydrochloric acid (1000 mL) and 6 N hydrochloric acid (10 mL) at 0° C. The resulting mixture was stirred at room temperature for 3 hr. The precipitates were filtered, washed with water, and dried to give a crude product (37 g). 30% amount of the reaction mixture was poured into 0.3 N hydrochloric acid (300 mL) and 6 N hydrochloric acid (5.0 mL) at 0° C. The resulting mixture was stirred at room temperature for 3 hr. The precipitates were filtered, washed with water, and dried to give a crude product (24 g). The combined crude products were dissolved in ethyl acetate and THF. The mixture was washed with 100:1 of water:1 N hydrochloric acid. The organic layer was washed with brine, dried over anhydrous sodium sulfate, and filtered. The filtrate was concentrated under reduced pressure, and crystallized from ethyl acetate and hexane to give the title compound (53 g). The mother liquor was concentrated under reduced pressure, purified by silica gel column chromatography (ethyl acetate/hexane), and crystallized from ethyl acetate and hexane to give the title compound (1.5 g).

MS: [M+H]⁺ 347.9, 349.9.

E) 5-bromo-N-((1S,2S)-2-((tert-butyldimethylsilyl)oxy)cyclopentyl)-3-chloro-2-hydroxy-4-methylbenzamide To a mixture of 5-bromo-3-chloro-2-hydroxy-N-((1S,2S)-2-hydroxycyclopentyl)-4-methylbenzamide (53 g), tert-butyldimethylsilyl chloride (34 g), and DMF (530 mL) was added imidazole (21 g) at room temperature, and the mixture was stirred at room temperature for 3 hr. The mixture was quenched with water (300 mL) and diluted with ethyl acetate (500 mL). The organic layer was separated. The aqueous layer was acidified with 1 N hydrochloric acid to pH=3. The mixture was extracted with ethyl acetate (500 mL). The combined organic extracts were washed with 0.001 N hydrochloric acid (200 mL) and brine (100 mL), dried over anhydrous magnesium sulfate, and concentrated under reduced pressure. The residue was purified by silica gel column chromatography (ethyl acetate/hexane) to give the title compound (41 g). The fractions containing a product with impurities were combined and concentrated under reduced pressure. To a mixture of the residue and methanol (300 mL) was added potassium carbonate (15 g) at room temperature, and the mixture was stirred at room temperature for 2.5 hr. Methanol was removed by evaporation under reduced pressure, and ethyl acetate (150 mL) and water (150 mL) were added thereto. The pH of aqueous layer was adjusted to 2-3 with 2 N hydrochloric acid, and the mixture was extracted with ethyl acetate (150 mL×2). The extracts were washed with brine (50 mL), dried over anhydrous magnesium sulfate, and concentrated under reduced pressure. The residue was purified by silica gel column chromatography (ethyl acetate/hexane) to give the title compound (28 g).

MS: [M+H]⁺ 462.1, 464.1.

F) 6-bromo-3-((1S,2S)-2-((tert-butyldimethylsilyl)oxy)cyclopentyl)-8-chloro-7-methyl-2H-benzo[e][1,3]oxazin-4 (3H)-one To a mixture of 5-bromo-N-((1S,2S)-2-((tert-butyldimethylsilyl)oxy)cyclopentyl)-3-chloro-2-hydroxy-4-methylbenzamide (68 g), chloroiodomethane (22 mL), and THF (1000 mL) was added cesium carbonate (145 g) at room temperature. The mixture was stirred at 60° C. overnight and refluxed for 4 hr. Chloroiodomethane (11 mL) was added thereto. The mixture was refluxed for 5 hr. Cesium carbonate (49 g) was added thereto, and the mixture was stirred at 60° C. overnight. After the mixture was allowed to be cooled to room temperature, water (500 mL) was added. The organic layer was separated, and the aqueous layer was extracted with ethyl acetate (300 mL). The organic layers were combined, washed with brine (100 mL), dried over anhydrous magnesium sulfate, and concentrated under reduced pressure. The residue was purified by NH silica gel column chromatography (ethyl acetate/hexane) and silica gel column chromatography (ethyl acetate/hexane) to give the title compound (29 g).

MS: [M+H]⁺ 474.0, 476.0.

G) 3-((1S,2S)-2-((tert-butyldimethylsilyl)oxy)cyclopentyl)-8-chloro-6-((6-chloropyridin-3-yl)methyl)-7-methyl-2H-benzo[e][1,3]oxazin-4 (3H)-one To a mixture of 6-bromo-3-((1S,2S)-2-((tert-butyldimethylsilyl)oxy)cyclopentyl)-8-chloro-7-methyl-2H-benzo[e][1,3]oxazin-4(3H)-one (29 g), bis(tri-tert-butylphosphine)palladium (0) (1.9 g), and THF (300 mL) was added dropwise a 0.5 M solution of ((6-chloropyridin-3-yl)methyl) zinc (II) chloride in THF (200 mL) at 0° C., and the mixture was stirred at room temperature for 2 hr under an argon atmosphere. The mixture was quenched with aqueous sodium hydrogen carbonate solution (500 mL), and the insoluble materials were removed by filtration through a pad of Celite. The organic layer of the filtrate was separated, and the aqueous layer was extracted with ethyl acetate (300 mL). The organic extracts were combined, washed with brine (100 mL), dried over anhydrous magnesium sulfate, and concentrated under reduced pressure. The residue was purified by NH silica gel column chromatography (ethyl acetate/hexane) and silica gel column chromatography (ethyl acetate/hexane) to give the title compound (20 g).

MS: [M+H]$^+$ 521.2.

H) 8-chloro-6-((6-chloropyridin-3-yl)methyl)-3-((1S,2S)-2-hydroxycyclopentyl)-7-methyl-2,3-dihydro-4H-1,3-benzoxazin-4-one To a mixture of 3-((1S,2S)-2-((tert-butyldimethylsilyl)oxy)cyclopentyl)-8-chloro-6-((6-chloropyridin-3-yl)methyl)-7-methyl-2H-benzo[e][1,3]oxazin-4(3H)-one (19 g) and THF (200 mL) was added a 1.0 M solution of tetrabutylammonium fluoride in THF (41 mL) at 0° C., and the mixture was stirred at 0° C. for 2.5 hr. A 1.0 M solution of tetrabutylammonium fluoride in THF (4 mL) was added thereto, and the mixture was stirred at 0° C. for 30 min. The mixture was quenched with aqueous sodium hydrogen carbonate solution (300 mL) and extracted with ethyl acetate (300 mL×2). The organic layer was separated, washed with brine (50 mL), dried over anhydrous magnesium sulfate, and concentrated under reduced pressure. The precipitates were collected by filtration and washed with diisopropyl ether/ethyl acetate=3/1 solution to give a crude product (13 g). The filtrate was concentrated under reduced pressure. The residue was purified by silica gel column chromatography (ethyl acetate/hexane) to give a crude product (1.6 g). A mixture of the crude product (13 g) in ethyl acetate (78 mL) was stirred at 60° C. for 30 min. Heptane (78 mL) was added dropwise at 60° C. thereto. The mixture was stirred at 60° C. for 1 hr and allowed to be cooled to room temperature for 2 hr. The precipitates were collected by filtration and washed with heptane/ethyl acetate=2/1 solution to give the title compound (11 g).

$^1$H NMR (300 MHz, DMSO-d$_6$) δ 1.37-1.55 (1H, m), 1.55-1.72 (3H, m), 1.74-1.97 (2H, m), 2.30 (3H, s), 4.01-4.15 (3H, m), 4.28-4.40 (1H, m), 4.91 (1H, d, J=5.1 Hz), 5.32-5.42 (2H, m), 7.44 (1H, dd, J=8.2, 0.6 Hz), 7.54-7.61 (2H, m), 8.28 (1H, d, J=2.0 Hz).

The obtained crystal was characterized by having specific peaks at the two theta of 7.8°±0.2°, 8.7°±0.2°, 10.8°±0.2°, 15.7°±0.2°, 16.1°±0.2°, 16.7°±0.2°, 19.2°±0.2° and 21.6°±0.2° degrees in a powder X-ray diffraction pattern.

Example 25

8-chloro-3-((1S,2S)-2-hydroxycyclopentyl)-7-methyl-6-((6-methylpyridin-3-yl)methyl)-2,3-dihydro-4H-1,3-benzoxazin-4-one To a mixture of 8-chloro-6-((6-chloropyridin-3-yl)methyl)-3-((1S,2S)-2-hydroxycyclopentyl)-7-methyl-2H-benzo[e][1,3]oxazin-4(3H)-one (0.45 g), 1,1'-bis(diphenylphosphino)ferrocene palladium (II) chloride dichloromethane complex (0.09 g) and THF (1 mL) was added methylzinc (II) chloride (2 M THF solution) (1.11 mL) under an argon atmosphere at room temperature, and the mixture was stirred at 60° C. overnight. To the reaction mixture were added 1,1'-bis(diphenylphosphino)ferrocene palladium (II) chloride dichloromethane complex (0.09 g) and methylzinc (II) chloride (2 M THF solution) (1.11 mL) at 60° C., and the mixture was stirred at the same temperature for 30 min. To the reaction mixture were added ethyl acetate and saturated aqueous ammonium chloride solution, the organic layer was separated, and the aqueous layer was extracted with ethyl acetate. The combined organic layer was washed with water and brine, dried over anhydrous magnesium sulfate and concentrated under reduced pressure. The residue was purified by NH silica gel column chromatography (ethyl acetate/hexane-methanol/ethyl acetate) and solidified with ethyl acetate and hexane to give the title compound (0.14 g).

$^1$H NMR (300 MHz, CDCl$_3$) δ 1.66-1.93 (4H, m), 1.99-2.16 (2H, m), 2.31 (3H, s), 2.51 (3H, s), 3.05 (1H, d, J=3.4 Hz), 3.97 (2H, s), 4.17-4.27 (1H, m), 4.32-4.42 (1H, m), 5.22-5.30 (2H, m), 7.05 (1H, d, J=7.9 Hz), 7.21-7.26 (1H, m), 7.68 (1H, s), 8.31 (1H, d, J=2.1 Hz).

Example 26

3-((1S,2S)-2-hydroxycyclopentyl)-7,8-dimethyl-6-((6-methylpyridin-3-yl)methyl)-2,3-dihydro-4H-1,3-benzoxazin-4-one Monohydrochloride $^1$H NMR (300 MHz, DMSO-d$_6$) δ 1.40-1.54 (1H, m), 1.56-1.72 (3H, m), 1.76-1.92 (2H, m), 2.12 (3H, s), 2.16 (3H, s), 2.69 (3H, s), 4.02-4.12 (1H, m), 4.19 (2H, s), 4.35 (1H, q, J=8.6 Hz), 5.22-5.31 (2H, m), 7.54 (1H, s), 7.79 (1H, d, J=8.3 Hz), 8.13 (1H, dd, J=8.3, 2.1 Hz), 8.60 (1H, d, J=1.7 Hz). The peak of two protons was not observed.

Example 27

8-fluoro-3-((1S,2S)-2-hydroxycyclohexyl)-7-methyl-6-((6-methylpyridin-3-yl)methyl)-2,3-dihydro-4H-1,3-benzoxazin-4-one

A) 2-(benzoyloxy)-5-bromo-3-fluoro-4-methylbenzoic Acid

To a mixture of 5-bromo-3-fluoro-2-hydroxy-4-methylbenzoic acid (3.30 g) and DMA (60 mL) was added benzoyl chloride (1.83 mL) at room temperature, and the mixture was stirred at the same temperature for 1 hr. To the reaction mixture was added benzoyl chloride (0.92 mL) at room temperature, and the mixture was stirred at the same temperature for 2 hr. To the reaction mixture were added ethyl acetate and water. The organic layer was separated, and the aqueous layer was extracted with ethyl acetate. The combined organic layer was washed with water and brine, dried over anhydrous magnesium sulfate and concentrated under reduced pressure to give the title compound (4.68 g). The obtained resultant product was used in the next step without further purification.

MS: [M–H]$^-$ 350.9, 352.9

B) 4-bromo-2-fluoro-6-(((1S,2S)-2-hydroxycyclohexyl)carbamoyl)-3-methylphenyl Benzoate To a mixture of 2-(benzoyloxy)-5-bromo-3-fluoro-4-methylbenzoic acid (4.68 g), (1S,2S)-2-aminocyclohexanol (1.53 g), triethylamine (2.03 mL) and DMF (50 mL) was added HATU (5.54 g) at 0° C., and the mixture was stirred at room temperature overnight. To the reaction mixture were added ethyl acetate and water at 0° C., the organic layer was separated, and the aqueous layer was extracted with ethyl acetate. The combined organic layer was washed with water and brine, dried over anhydrous magnesium sulfate and concentrated under reduced pressure. The residue was purified by silica gel column chromatography (ethyl acetate/hexane) to give the title compound (2.10 g).

MS: [M+H]$^+$ 450.1, 452.1

C) 6-bromo-8-fluoro-3-((1S,2S)-2-hydroxycyclohexyl)-7-methyl-2H-benzo[e][1,3]oxazin-4(3H)-one To a mixture of 4-bromo-2-fluoro-6-(((1S,2S)-2-hydroxycyclohexyl)carbamoyl)-3-methylphenyl benzoate (2.10 g), THF (40 mL) and methanol (5 mL) was added 1N aqueous sodium hydroxide solution (1.17 mL) at room temperature, and the mixture was stirred at the same temperature for 4 hr. To the reaction mixture was added 2N hydrochloric acid to adjust pH to 2-3, and ethyl acetate and water were added. The organic layer was separated, and the aqueous layer was extracted with ethyl acetate. The combined organic layer was washed with water and brine, dried over anhydrous magnesium sulfate and concentrated under reduced pressure.

To a mixture of the obtained residue, paraformaldehyde (0.42 g) and toluene (40 mL) was added p-toluenesulfonic acid monohydrate (0.27 g) at room temperature, and the mixture was stirred at 100° C. for 3 hr and then at room temperature for 60 hr. To the reaction mixture were added ethyl acetate and saturated aqueous sodium hydrogen carbonate solution, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.70 g).

MS: [M–H]$^-$ 356.0, 358.0

D) 6-((6-chloropyridin-3-yl)methyl)-8-fluoro-3-((1S,2S)-2-hydroxycyclohexyl)-7-methyl-2H-benzo[e][1,3]oxazin-4 (3H)-one To a mixture of 6-bromo-8-fluoro-3-((1S,2S)-2-hydroxycyclohexyl)-7-methyl-2H-benzo[e][1,3]oxazin-4 (3H)-one (0.70 g), bis(tri-tert-butylphosphine)palladium (0) (0.10 g) and THF (7 mL) was added ((6-chloropyridin-3-yl)methyl)zinc (II) chloride (0.5 M THF solution) (7.82 mL) under an argon atmosphere at room temperature, and the mixture was stirred at the same temperature overnight. To the reaction mixture were added ethyl acetate and water, the organic layer was separated, and the aqueous layer was extracted with ethyl acetate. The combined organic layer was washed with water and brine, dried over anhydrous magnesium sulfate and concentrated under reduced pressure. The residue was purified by silica gel column chromatography (ethyl acetate/hexane) to give the title compound (0.45 g).

MS: [M+H]$^+$ 405.2

E) 8-fluoro-3-((1S,2S)-2-hydroxycyclohexyl)-7-methyl-6-((6-methylpyridin-3-yl)methyl)-2,3-dihydro-4H-1,3-benzoxazin-4-one To a mixture of 6-((6-chloropyridin-3-yl)methyl)-8-fluoro-3-((1S,2S)-2-hydroxycyclohexyl)-7-methyl-2H-benzo[e][1,3]oxazin-4(3H)-one (0.20 g), 1,1'-bis(diphenylphosphino)ferrocene palladium (II) chloride dichloromethane complex (0.04 g) and THF (2 mL) was added methylzinc (II) chloride (2 M THF solution) (0.49 mL) under an argon atmosphere at room temperature, and the mixture was stirred at 60° C. for 2 hr. To the reaction mixture were added ethyl acetate and saturated aqueous ammonium chloride solution, and the organic layer was separated. The aqueous layer was extracted with ethyl acetate and the combined organic layer was washed with water and brine, dried over anhydrous magnesium sulfate and concentrated under reduced pressure. The residue was purified by NH silica gel column chromatography (ethyl acetate/hexane) and solidified with ethyl acetate and hexane to give the title compound (0.13 g).

$^1$H NMR (300 MHz, CDCl$_3$) δ 1.25-1.46 (3H, m), 1.50-1.66 (1H, m), 1.81 (2H, d, J=10.6 Hz), 1.86-1.99 (2H, m), 2.12-2.21 (4H, m), 2.51 (3H, s), 3.51-3.65 (1H, m), 3.90-3.97 (2H, m), 4.12-4.25 (1H, m), 5.21-5.30 (2H, m), 7.05 (1H, d, J=8.1 Hz), 7.24 (1H, d, J=2.3 Hz), 7.54 (1H, d, J=1.1 Hz), 8.32 (1H, d, J=1.9 Hz).

Example 28

3-(trans-2-hydroxycyclohexyl)-7-methyl-6-((6-methylpyridin-3-yl)methyl)-2,3-dihydro-4H-1,3-benzoxazin-4-one Monohydrochloride (Optical Isomer)

A) 6-bromo-3-(trans-2-hydroxycyclohexyl)-7-methyl-2H-benzo[e][1,3]oxazin-4 (3H)-one To a mixture of 5-bromo-2-hydroxy-4-methylbenzoic acid (6.3 g), trans-2-aminocyclohexanol hydrochloride (4.55 g), WSC hydrochloride (6.27 g), HOBt monohydrate (4.18 g) and DMF (50 mL) was added triethylamine (4.18 mL), and the mixture was stirred at room temperature overnight. To the reaction mixture was added water, and the mixture was extracted with ethyl acetate. The organic layer was washed with water, dried over anhydrous magnesium sulfate and concentrated under reduced pressure. A mixture of the obtained residue, paraformaldehyde (4.09 g), p-toluenesulfonic acid monohydrate (2.59 g) and toluene (100 mL) was heated under reflux for 2 hr. The reaction mixture was concentrated under reduced pressure, and the residue was purified by silica gel column chromatography (ethyl acetate/hexane) to give the title compound (2.03 g).

MS: [M+H]$^+$ 339.9, 341.9

B) 6-((6-chloropyridin-3-yl)methyl)-3-(trans-2-hydroxycyclohexyl)-7-methyl-2H-benzo[e][1,3]oxazin-4 (3H)-one To a mixture of 6-bromo-3-(trans-2-hydroxycyclohexyl)-7-methyl-2H-benzo[e][1,3]oxazin-4 (3H)-one (0.30 g) and THF (10 mL) were added ((6-chloropyridin-3-yl)methyl) zinc (II) chloride (0.5 M THF solution) (4.41 mL) and bis(tri-tert-butylphosphine)palladium (0) (0.05 g) under an argon atmosphere at 0° C., and the mixture was stirred at room temperature overnight. To the reaction mixture was added saturated aqueous sodium carbonate solution, and the mixture was stirred for 1 hr. The insoluble material was filtered off through celite. The filtrate was extracted with ethyl acetate, and the organic layer was washed with brine, dried over anhydrous magnesium sulfate and concentrated under reduced pressure. The residue was purified by silica gel column chromatography (ethyl acetate/hexane) and solidified with ethyl acetate to give the title compound (0.18 g).

MS: [M+H]$^+$ 387.0

C) 3-(trans-2-hydroxycyclohexyl)-7-methyl-6-((6-methylpyridin-3-yl)methyl)-2H-benzo [e][1,3]oxazin-4 (3H)-one To a mixture of 6-((6-chloropyridin-3-yl)methyl)-3-(trans-2-hydroxycyclohexyl)-7-methyl-2H-benzo[e][1,3] oxazin-4(3H)-one (0.16 g), 1,1'-bis(diphenylphosphino)ferrocene palladium (II) chloride dichloromethane complex (0.02 g) and THF (2 mL) was added methylzinc (II) chloride (2 M THF solution) (0.62 mL) under an argon atmosphere at room temperature, and the mixture was stirred at 80° C. overnight. Water was added to the reaction mixture at room temperature, and the mixture was extracted with a mixed solvent of ethyl acetate and THF. The organic layer was washed with water and brine, dried over anhydrous magnesium sulfate and concentrated under reduced pressure. The residue was purified by NH silica gel column chromatography (ethyl acetate/hexane) and crystallized from ethyl acetate to give the title compound (0.11 g).

MS: [M+H]$^+$ 367.2

D) 3-(trans-2-hydroxycyclohexyl)-7-methyl-6-((6-methylpyridin-3-yl)methyl)-2,3-dihydro-4H-1,3-benzoxazin-4-one Monohydrochloride (Optical Isomer)

3-(trans-2-Hydroxycyclohexyl)-7-methyl-6-((6-methylpyridin-3-yl)methyl)-2H-benzo[e][1,3]oxazin-4(3H)-one (0.11 g) was optically resolved by HPLC (Chiral PAK IC, 50 mm ID×500 mm L, mobile phase:ethanol) to give a product with a longer retention time (0.05 g). To a mixture of the obtained optically active form and ethyl acetate (1 mL) was added 4N hydrogen chloride (ethyl acetate solution) (0.036 mL), and the mixture was stirred for 10 min. The resulting solid was collected by filtration, washed with ethyl acetate, and dried under reduced pressure to give the title compound (0.05 g).

$^1$H NMR (300 MHz, DMSO-d$_6$) δ 1.13-1.28 (3H, m), 1.54-1.73 (4H, m), 1.91 (1H, s), 2.25 (3H, s), 2.38-2.46 (1H, m), 2.65 (3H, s), 3.49-3.57 (1H, m), 3.87-3.98 (1H, m), 4.12 (2H, s), 5.10-5.38 (2H, m), 6.91 (1H, s), 7.58 (1H, s), 7.72 (1H, d, J=8.1 Hz), 8.06 (1H, d, J=8.7 Hz), 8.60 (1H, s). The peak of one proton was not observed.

Example 29

3-((3S,4S)-4-hydroxytetrahydro-2H-pyran-3-yl)-6-((6-methoxypyridin-3-yl)methyl)-7,8-dimethyl-2,3-dihydro-4H-1,3-benzoxazin-4-one Alias; 1,5-anhydro-2,4-dideoxy-2-(6-((6-methoxypyridin-3-yl)methyl)-7,8-dimethyl-4-oxo-2H-1,3-benzoxazin-3(4H)-yl)-L-threo-pentitol To a mixture of 3-((3S,4S)-4-hydroxytetrahydro-2H-pyran-3-yl)-7,8-dimethyl-6-(4,4,5,5-tetramethyl-1,3,2-di-oxaborolan-2-yl)-2H-benzo[e][1,3]oxazin-4 (3H)-one (0.20 g), 5-(chloromethyl)-2-methoxypyridine (0.08 g), 1,1'-bis (diphenylphosphino)ferrocene palladium (II) chloride dichloromethane complex (0.02 g) and DME (10 mL) was added 2 M aqueous sodium carbonate solution (0.50 mL), and the mixture was stirred under an argon atmosphere at 80° C. overnight. The reaction mixture was diluted with ethyl acetate, dried over anhydrous magnesium sulfate and concentrated under reduced pressure. The residue was purified by silica gel column chromatography (ethyl acetate/hexane) and solidified with ethyl acetate to give the title compound (0.11 g).

$^1$H NMR (300 MHz, CDCl$_3$) δ 1.64-1.85 (1H, m), 2.05-2.13 (1H, m), 2.15 (3H, s), 2.16 (3H, s), 2.27 (1H, d, J=5.5 Hz), 3.48 (1H, td, J=11.7, 2.4 Hz), 3.61-3.74 (1H, m), 3.86-3.91 (5H, m), 3.92-4.05 (3H, m), 4.06-4.23 (1H, m), 5.14-5.29 (2H, m), 6.64 (1H, d, J=8.5 Hz), 7.27-7.31 (1H, m), 7.59 (1H, s), 7.93 (1H, d, J=1.9 Hz).

Example 50

1,5-anhydro-2,4-dideoxy-2-(7-methyl-4-oxo-6-(4-(1H-pyrazol-1-yl)benzyl)-2H-1,3-benzoxazin-3(4H)-yl)-L-threo-pentitol The title compound was obtained by a method similar to that in Example 6 or Example 103.

$^1$H NMR (300 MHz, CDCl$_3$) δ 1.65-1.83 (1H, m), 2.02-2.15 (2H, m), 2.24 (3H, s), 3.42-3.52 (1H, m), 3.59-3.75 (1H, m), 3.88-4.25 (6H, m), 5.22 (2H, d, J=1.7 Hz), 6.40-6.48 (1H, m), 6.80 (1H, s), 7.18 (2H, d, J=8.5 Hz), 7.54-7.64 (2H, m), 7.70 (1H, d, J=1.7 Hz), 7.74 (1H, s), 7.88 (1H, d, J=2.3 Hz).

Example 89

8-fluoro-6-((2'-fluoro-2,4'-bipyridin-5-yl)methyl)-3-((1S,2S)-2-hydroxycyclopentyl)-7-methyl-2,3-dihydro-4H-1,3-benzoxazin-4-one To a mixture of 6-((6-chloropyridin-3-yl)methyl)-8-fluoro-3-((1S,2S)-2-hydroxycyclopentyl)-7-methyl-2,3-dihydro-4H-1,3-benzoxazin-4-one (0.05 g), (2-fluoropyridin-4-yl)boronic acid (0.03 g), 2 M aqueous sodium carbonate solution (0.13 mL) and DME (3 mL)-water (0.3 mL) was added bis(di-tert-butyl(4-dimethylaminophenyl)phosphine) dichloropalladium (II) (0.01 g), and the mixture was subjected to microwave irradiation at 110° C. for 50 min. The reaction mixture was dried over anhydrous sodium sulfate, and concentrated under reduced pressure. The residue was purified by NH silica gel column chromatography (ethyl acetate/hexane) and solidified with ethyl acetate to give the title compound (0.01 g). The filtrate was further concentrated and solidified with ethyl acetate-diisopropyl ether to give the title compound (0.03 g) as the second crystal.

$^1$H NMR (300 MHz, DMSO-d$_6$) δ 1.34-1.53 (1H, m), 1.58-1.69 (3H, m), 1.77-1.93 (2H, m), 2.21 (3H, d, J=2.5 Hz), 4.00-4.10 (1H, m), 4.12-4.17 (2H, m), 4.25-4.44 (1H, m), 4.90 (1H, d, J=5.1 Hz), 5.35 (2H, d, J=3.0 Hz), 7.42-7.47 (1H, m), 7.69-7.75 (1H, m), 7.77-7.81 (1H, m), 8.02 (1H, dt, J=5.1, 1.9 Hz), 8.12 (1H, dd, J=8.0, 0.5 Hz), 8.35 (1H, d, J=5.3 Hz), 8.62 (1H, d, J=1.7 Hz).

Example 90

8-fluoro-3-((1S,2S)-2-hydroxycyclopentyl)-7-methyl-6-((2'-methyl-2,4'-bipyridin-5-yl)methyl)-2,3-dihydro-4H-1,3-benzoxazin-4-one To a mixture of 6-((6-chloropyridin-3-yl)methyl)-8-fluoro-3-((1S,2S)-2-hydroxycyclopentyl)-7-methyl-2,3-dihydro-4H-1,3-benzoxazin-4-one (0.05 g), 2-methyl-4-(4,4,5,5-tetramethyl-1,3,2-dioxaborolan-2-yl)pyridine (0.04 g), 2 M aqueous sodium carbonate solution (0.13 mL) and DME (3 mL)-water (0.3 mL) was added bis(di-tert-butyl(4-dimethylaminophenyl)phosphine)dichloropalladium (II) (0.004 g), and the mixture was subjected to microwave irradiation at 110° C. for 50 min. The reaction mixture was dried over anhydrous sodium sulfate, and concentrated under reduced pressure. The residue was purified by NH silica gel column chromatography (ethyl acetate/hexane) and solidified with ethyl acetate to give the title compound (0.04 g).

$^1$H NMR (300 MHz, DMSO-d$_6$) δ 1.35-1.52 (1H, m), 1.63 (3H, d, J=5.7 Hz), 1.75-1.94 (2H, m), 2.21 (3H, d, J=2.5 Hz), 2.54 (3H, s), 4.01-4.10 (1H, m), 4.12 (2H, s), 4.27-4.42 (1H, m), 4.90 (1H, d, J=5.1 Hz), 5.35 (2H, d, J=3.2 Hz), 7.45 (1H, s), 7.67 (1H, dd, J=8.2, 2.4 Hz), 7.81 (1H, dd, J=5.2, 1.2 Hz), 7.90 (1H, s), 8.02 (1H, d, J=8.1 Hz), 8.54 (1H, d, J=5.3 Hz), 8.59 (1H, d, J=1.7 Hz).

Example 91

6-((6-(1-ethyl-1H-pyrazol-3-yl)pyridin-3-yl)methyl)-8-fluoro-3-((1S,2S)-2-hydroxycyclopentyl)-7-methyl-2,3-dihydro-4H-1,3-benzoxazin-4-one To a mixture of 6-((6-chloropyridin-3-yl)methyl)-8-fluoro-3-((1S,2S)-2-hydroxycyclopentyl)-7-methyl-2,3-dihydro-4H-1,3-benzoxazin-4-one (0.05 g), 1-ethyl-3-(4,4,5,5-tetramethyl-1,3,2-dioxaborolan-2-yl)-1H-pyrazole (0.04 g), 1,1'-bis(diphenylphosphino)ferrocene palladium (II) chloride dichloromethane complex (0.01 g) and DME (3 mL)-water (0.3 mL) was added 2 M aqueous sodium carbonate solution (0.13 mL), and the mixture was subjected to microwave irradiation at 110° C. for 50 min. The reaction mixture was dried over anhydrous sodium sulfate, and concentrated under reduced pressure. The residue was purified by NH silica gel column chromatography (ethyl acetate/hexane) and solidified with ethanol to give the title compound (0.03 g).

$^1$H NMR (300 MHz, DMSO-d$_6$) δ 1.41 (3H, t, J=7.3 Hz), 1.43-1.53 (1H, m), 1.56-1.72 (3H, m), 1.75-1.94 (2H, m), 2.20 (3H, d, J=2.5 Hz), 4.01-4.11 (3H, m), 4.19 (2H, q, J=7.4 Hz), 4.27-4.41 (1H, m), 4.90 (1H, d, J=5.1 Hz), 5.28-5.42 (2H, m), 6.75 (1H, d, J=2.3 Hz), 7.43 (1H, s), 7.51 (1H, dd, J=8.1, 2.3 Hz), 7.79 (1H, d, J=2.3 Hz), 7.80-7.87 (1H, m), 8.42 (1H, d, J=1.7 Hz).

Example 92

8-fluoro-3-((1S,2S)-2-hydroxycyclohexyl)-7-methyl-6-((6-(1-methyl-1H-pyrazol-3-yl)pyridin-3-yl)methyl)-2,3-dihydro-4H-1,3-benzoxazin-4-one To a mixture of 6-((6-chloropyridin-3-yl)methyl)-8-fluoro-3-((1S,2S)-2-hydroxycyclohexyl)-7-methyl-2H-benzo[e][1,3]oxazin-4(3H)-one (0.04 g), 1-methyl-3-(4,4,5,5-tetramethyl-1,3,2-dioxaborolan-2-yl)-1H-pyrazole (0.03 g), 2 M aqueous sodium carbonate solution (0.1 mL) and DME (3 mL)-water (0.3 mL) was added bis(di-tert-butyl(4-dimethylaminophenyl)phosphine)dichloropalladium (II) (0.003 g), and the mixture was subjected to microwave irradiation at 110° C. for 50 min. The reaction mixture was dried over anhydrous sodium sulfate, and concentrated under reduced pressure. The residue was purified by NH silica gel column chromatography (ethyl acetate/hexane) and solidified with ethanol to give the title compound (0.03 g).

$^1$H NMR (300 MHz, DMSO-d$_6$) δ 1.15-1.32 (3H, m), 1.54-1.72 (4H, m), 1.86-1.99 (1H, m), 2.19 (3H, d, J=2.5 Hz), 3.47-3.65 (1H, m), 3.90 (3H, s), 3.92-3.99 (1H, m), 4.05 (2H, s), 4.76 (1H, d, J=5.5 Hz), 5.22-5.48 (2H, m), 6.75 (1H, d, J=2.3 Hz), 7.41-7.45 (1H, m), 7.51 (1H, dd, J=8.1, 2.3 Hz), 7.74 (1H, d, J=2.3 Hz), 7.82 (1H, dd, J=8.1, 0.8 Hz), 8.42 (1H, d, J=1.7 Hz).

Example 93

6-((6-(1,3-dimethyl-1H-pyrazol-4-yl)pyridin-3-yl)methyl)-8-fluoro-3-((1S,2S)-2-hydroxycyclopentyl)-7-methyl-2,3-dihydro-4H-1,3-benzoxazin-4-one A mixture of 6-((6-chloropyridin-3-yl)methyl)-8-fluoro-3-((1S,2S)-2-hydroxycyclopentyl)-7-methyl-2,3-dihydro-4H-1,3-benzoxazin-4-one (0.05 g), 1,3-dimethyl-4-(4,4,5,5-tetramethyl-1,3,2-dioxaborolan-2-yl)-1H-pyrazole (0.04 g), 1,1'-bis(diphenylphosphino)ferrocene palladium (II) chloride dichloromethane complex (0.01 g), 2 M aqueous sodium carbonate solution (0.13 mL) and DME (3 mL)-water (0.3 mL) was stirred under an argon atmosphere at 90° C. overnight. The reaction mixture was dried over anhydrous sodium sulfate, and concentrated under reduced pressure. The residue was purified by NH silica gel column chromatography (ethyl acetate/hexane) and solidified with ethanol to give the title compound (0.03 g).

$^1$H NMR (300 MHz, DMSO-d$_6$) δ 1.46 (1H, dd, J=12.7, 7.1 Hz), 1.54-1.72 (3H, m), 1.75-1.95 (2H, m), 2.21 (3H, d, J=2.3 Hz), 2.40 (3H, s), 3.78 (3H, s), 3.93-4.19 (3H, m), 4.34 (1H, d, J=8.3 Hz), 4.89 (1H, d, J=5.1 Hz), 5.25-5.42 (2H, m), 7.39-7.52 (3H, m), 8.08-8.12 (1H, m), 8.37 (1H, s).

Example 94

3-(trans-2-hydroxycyclohexyl)-7-methyl-6-((6-(1H-pyrazol-1-yl)pyridin-3-yl)methyl)-2,3-dihydro-4H-1,3-benzoxazin-4-one (Optical Isomer: Shorter Retention Time)

A) 3-(trans-2-hydroxycyclohexyl)-7-methyl-6-(4,4,5,5-tetramethyl-1,3,2-dioxaborolan-2-yl)-2H-benzo[e][1,3]oxazin-4(3H)-one To a mixture of 6-bromo-3-(trans-2-hydroxycyclohexyl)-7-methyl-2H-benzo[e][1,3]oxazin-4(3H)-one (6.6 g), bis(pinacolato)diboron (9.85 g), potassium acetate (5.71 g) and toluene (150 mL) was added dichlorobis(triphenylphosphine)palladium (II) (2.72 g), and the mixture was stirred under an argon atmosphere at 110° C. overnight. The insoluble material in the reaction mixture was filtered off, and the filtrate was concentrated under reduced pressure. The residue was purified by silica gel column chromatography (ethyl acetate/hexane) to give the title compound (6.30 g).

$^1$H NMR (300 MHz, CDCl$_3$) δ 1.31-1.34 (12H, m), 1.34-1.61 (3H, m), 1.72-1.94 (3H, m), 2.10-2.29 (2H, m), 2.54 (3H, s), 3.47-3.62 (1H, m), 4.15-4.25 (1H, m), 5.17 (2H, s), 6.75 (1H, s), 8.38 (1H, s), 1H was not observed.

B) 3-(trans-2-hydroxycyclohexyl)-7-methyl-6-((6-(1H-pyrazol-1-yl)pyridin-3-yl)methyl)-2,3-dihydro-4H-1,3-benzoxazin-4-one To a mixture of 3-(trans-2-hydroxycyclohexyl)-7-methyl-6-(4,4,5,5-tetramethyl-1,3,2-dioxaborolan-2-yl)-2H-benzo[e][1,3]oxazin-4(3H)-one (0.10 g), 5-(bromomethyl)-2-(1H- pyrazol-1-yl)pyridine (0.08 g), 1,1'-bis(diphenylphosphino) ferrocene palladium (II) chloride dichloromethane complex (0.01 g) in DME (2 mL)-water (0.2 mL) was added 2 M aqueous sodium carbonate solution (0.26 mL), and the mixture was stirred under an argon atmosphere at 90° C. overnight. The reaction mixture was diluted with ethyl acetate, dried over anhydrous sodium sulfate, and concentrated under reduced pressure. The residue was purified by silica gel column chromatography (ethyl acetate/hexane) and recrystallized from ethyl acetate-diisopropyl ether to give the title compound (0.07 g).
$^1$H NMR (300 MHz, CDCl$_3$) δ 1.22-1.46 (3H, m), 1.55-1.67 (1H, m), 1.73-1.84 (2H, m), 1.86-1.97 (1H, m), 2.11-2.19 (1H, m), 2.24 (3H, s), 3.50-3.71 (1H, m), 3.95-4.03 (2H, m), 4.09-4.28 (1H, m), 5.14-5.22 (2H, m), 6.40-6.48 (1H, m), 6.81 (1H, s), 7.52 (1H, dd, J=8.5, 2.3 Hz), 7.71 (1H, d, J=1.1 Hz), 7.77 (1H, s), 7.87 (1H, d, J=8.5 Hz), 8.21 (1H, d, J=1.9 Hz), 8.51 (1H, d, J=2.3 Hz), 1H was not observed.

C) 3-(trans-2-hydroxycyclohexyl)-7-methyl-6-((6-(1H-pyrazol-1-yl)pyridin-3-yl)methyl)-2,3-dihydro-4H-1,3-benzoxazin-4-one (Optical Isomer: Shorter Retention Time)

3-(trans-2-Hydroxycyclohexyl)-7-methyl-6-((6-(1H-pyrazol-1-yl)pyridin-3-yl)methyl)-2,3-dihydro-4H-1,3-benzoxazin-4-one (0.06 g) was optically resolved by HPLC (Chiral PAK IA, 50 mm ID×500 mm L, mobile phase: ethanol) and a product with a shorter retention time was solidified with ethanol to give the title compound (0.02 g).
$^1$H NMR (300 MHz, DMSO-d$_6$) δ 1.22 (3H, brs), 1.55-1.72 (4H, m), 1.85-1.97 (1H, m), 2.26 (3H, s), 3.40-3.60 (1H, m), 3.80-3.98 (1H, m), 4.04 (2H, s), 4.72 (1H, d, J=5.3 Hz), 5.13-5.36 (2H, m), 6.56 (1H, dd, J=2.5, 1.7 Hz), 6.90 (1H, s), 7.56 (1H, s), 7.69 (1H, dd, J=8.4, 2.4 Hz), 7.77-7.80 (1H, m), 7.86 (1H, d, J=8.9 Hz), 8.32 (1H, d, J=1.7 Hz), 8.58 (1H, dd, J=2.5, 0.7 Hz).

Example 95

3-((1S,2S)-2-hydroxycyclohexyl)-7-methyl-6-((6-(1H-pyrazol-1-yl)pyridin-3-yl)methyl)-2,3-dihydro-4H-1,3-benzoxazin-4-one (Optical Isomer: Longer Retention Time)

3-(trans-2-Hydroxycyclohexyl)-7-methyl-6-((6-(1H-pyrazol-1-yl)pyridin-3-yl)methyl)-2,3-dihydro-4H-1,3-benzoxazin-4-one (0.06 g) was optically resolved by HPLC (Chiral PAK IA, 50 mm ID×500 mm L, mobile phase: ethanol) and a product with a longer retention time was solidified with ethanol to give the title compound (0.02 g).
$^1$H NMR (300 MHz, DMSO-d$_6$) δ 1.22 (3H, brs), 1.62 (4H, brs), 1.84-1.99 (1H, m), 2.26 (3H, s), 3.44-3.63 (1H, m), 3.79-3.99 (1H, m), 4.04 (2H, s), 4.72 (1H, d, J=5.3 Hz), 5.10-5.35 (2H, m), 6.56 (1H, dd, J=2.5, 1.7 Hz), 6.90 (1H, s), 7.56 (1H, s), 7.69 (1H, dd, J=8.4, 2.4 Hz), 7.79 (1H, dd, J=1.6, 0.7 Hz), 7.86 (1H, d, J=8.3 Hz), 8.32 (1H, d, J=1.9 Hz), 8.58 (1H, dd, J=2.6, 0.6 Hz).

Example 96

8-chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one (Optical Isomer: Shorter Retention Time)

A) 5-bromo-3-chloro-2-hydroxy-N-(trans-2-hydroxycyclopentyl)-4-methylbenzamide

A mixture of methyl 5-bromo-3-chloro-2-hydroxy-4-methylbenzoate (2.90 g), trans-2-aminocyclopentanol hydrochloride (2.84 g) and triethylamine (4.20 g) in methanol/dichloromethane was stirred with heating under reflux for 3 days. The reaction mixture was concentrated, and purified by silica gel column chromatography (ethyl acetate/petroleum ether) to give the title compound (1.70 g).
$^1$H NMR (400 MHz, CDCl$_3$) δ 1.65-1.95 (4H, m), 2.02-2.10 (1H, m), 2.25-2.35 (1H, m), 2.55 (3H, s), 3.55 (1H, brs), 4.02-4.12 (2H, m), 6.45 (1H, brs), 7.51 (1H, s). 1H was not observed.

B) 6-bromo-8-chloro-3-(trans-2-hydroxycyclopentyl)-7-methyl-2,3-dihydro-4H-1,3-benzoxazin-4-one A mixture of 5-bromo-3-chloro-2-hydroxy-N-(trans-2-hydroxycyclopentyl)-4-methylbenzamide (1.70 g), formaldehyde (37% aqueous solution) (10 mL) and formic acid (10 mL) was stirred at 50° C. for 2 days. The reaction mixture was cooled to room temperature. Saturated aqueous sodium hydrogen carbonate solution and ethyl acetate were added for partitioning. The aqueous layer was extracted 3 times with ethyl acetate, and the organic layer was dried over anhydrous sodium sulfate, and concentrated under reduced pressure. The residue was purified by silica gel column chromatography (ethyl acetate/petroleum ether) to give the title compound (0.78 g).
$^1$H NMR (400 MHz, CDCl$_3$) δ 1.60-1.90 (4H, m), 2.00-2.13 (2H, m), 2.55 (3H, s), 4.20-4.30 (1H, m), 4.35-4.45 (1H, m), 5.26 (2H, s), 8.03 (1H, s). Proton for 1.62-1.95 ppm overlapped with water signal and 1H was not observed.

C) 8-chloro-3-(trans-2-hydroxycyclopentyl)-7-methyl-6-(4,4,5,5-tetramethyl-1,3,2-dioxaborolan-2-yl)-2,3-dihydro-4H-1,3-benzoxazin-4-one A mixture of 6-bromo-8-chloro-3-(trans-2-hydroxycyclopentyl)-7-methyl-2,3-dihydro-4H-1,3-benzoxazin-4-one (0.78 g), bis(pinacolato)diboron (0.66 g), 1,1'-bis(diphenylphosphino)ferrocene palladium (II) chloride dichloromethane complex (0.18 g), potassium acetate (0.85 g) and anhydrous dioxane (10 mL) was stirred under a nitrogen atmosphere at 80° C. for 16 hr. The reaction mixture was cooled to room temperature and the insoluble material was filtered off through celite, and washed with ethyl acetate. The filtrate was partitioned between water and ethyl acetate, and the aqueous layer was extracted 3 times with ethyl acetate. The organic layer was dried over anhydrous sodium sulfate, and concentrated under reduced pressure. The residue was purified by silica gel column chromatography (ethyl acetate/petroleum ether) to give the title compound (0.64 g).
$^1$H NMR (400 MHz, CDCl$_3$) δ 1.33 (12H, s), 1.60-1.90 (4H, m), 1.95-2.10 (2H, m), 2.63 (3H, s), 3.52 (1H, brs), 4.15-4.25 (1H, m), 4.30-4.40 (1H, m), 5.20-5.35 (2H, m), 8.29 (1H, s). Proton for 1.60-1.90 ppm overlapped with water signal.

D) 8-chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one To a mixture of 8-chloro-3-(trans-2-hydroxycyclopentyl)-7-methyl-6-(4,4,5,5-tetramethyl-1,3,2-dioxaborolan-2-yl)-2,3-dihydro-4H-1,3-benzoxazin-4-one (0.15 g) and sodium carbonate (0.39 g) in DME (9 mL)-water (3 mL) were added 5-(bromomethyl)-2-(1H-pyrazol-1-yl)pyridine (0.11 g) and tetrakis(triphenylphosphine)palladium (0) (0.02 g), and the mixture was stirred under a nitrogen atmosphere at 85° C. for 0.5 hr. As another batch, to a mixture of 8-chloro-3-

(trans-2-hydroxycyclopentyl)-7-methyl-6-(4,4,5,5-tetramethyl-1,3,2-dioxaborolan-2-yl)-2,3-dihydro-4H-1,3-benzoxazin-4-one (0.30 g) and sodium carbonate (0.78 g) in DME (18 mL)-water (6 mL) were added 5-(bromomethyl)-2-(1H-pyrazol-1-yl)pyridine (0.21 g) and tetrakis(triphenylphosphine)palladium (0) (0.04 g), and the mixture was stirred under a nitrogen atmosphere at 85° C. for 0.5 hr. After cooling to room temperature, the reaction mixture containing the both batches was extracted 3 times with ethyl acetate. The extracts were combined, dried over anhydrous sodium sulfate, and concentrated under reduced pressure. The residue was purified by preparative HPLC and freeze-dried to give the title compound (0.05 g).

MS: [M+H]$^+$ 438.9

E) 8-chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one (Optical Isomer: Shorter Retention Time)

8-Chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one (0.05 g) was optically resolved by HPLC (Chiral PAK IA, 50 mm ID×500 mm L, mobile phase:ethanol), and a product with a shorter retention time was solidified with ethanol to give the title compound (0.01 g).

$^1$H NMR (300 MHz, DMSO-d$_6$) δ 1.36-1.53 (1H, m), 1.55-1.72 (3H, m), 1.76-1.94 (2H, m), 2.34 (3H, s), 4.00-4.11 (1H, m), 4.14 (2H, s), 4.28-4.43 (1H, m), 4.90 (1H, d, J=5.1 Hz), 5.38 (2H, d, J=2.3 Hz), 6.56 (1H, dd, J=2.6, 1.7 Hz), 7.61 (1H, s), 7.69 (1H, dd, J=8.4, 2.4 Hz), 7.79 (1H, dd, J=1.7, 0.8 Hz), 7.86 (1H, d, J=8.3 Hz), 8.33 (1H, d, J=1.7 Hz), 8.58 (1H, dd, J=2.6, 0.6 Hz).

Example 97

8-chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one (Optical Isomer: Longer Retention Time)

8-Chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one (0.05 g) was optically resolved by HPLC (Chiral PAK IA, 50 mm ID×500 mm L, mobile phase:ethanol), and a product with a longer retention time was solidified with ethanol to give the title compound (0.02 g).

$^1$H NMR (300 MHz, DMSO-d$_6$) δ 1.32-1.53 (1H, m), 1.56-1.72 (3H, m), 1.76-1.96 (2H, m), 2.34 (3H, s), 3.99-4.10 (1H, m), 4.14 (2H, s), 4.25-4.46 (1H, m), 4.90 (1H, d, J=5.3 Hz), 5.38 (2H, d, J=2.1 Hz), 6.56 (1H, dd, J=2.5, 1.7 Hz), 7.61 (1H, s), 7.69 (1H, dd, J=8.4, 2.4 Hz), 7.79 (1H, dd, J=1.6, 0.7 Hz), 7.86 (1H, d, J=8.5 Hz), 8.33 (1H, d, J=1.7 Hz), 8.58 (1H, dd, J=2.5, 0.7 Hz).

Example 98

1,5-anhydro-2,4-dideoxy-2-(7,8-dimethyl-4-oxo-6-((6-(1H-pyrazol-1-yl)pyridin-3-yl)methyl)-2H-1,3-benzoxazin-3(4H)-yl)-L-threo-pentitol A) 5-(chloromethyl)-2-(1H-pyrazol-1-yl)pyridine Hydrochloride To a mixture of (6-(1H-pyrazol-1-yl)pyridin-3-yl)methanol (4.42 g) and THF (80 mL) was added under ice-cooling thionyl chloride (4.50 g), and the mixture was stirred for 1 hr. To the reaction mixture was added ethyl acetate (100 mL)-saturated aqueous sodium hydrogen carbonate solution (100 mL) at room temperature. The aqueous layer was extracted two times with ethyl acetate, and the organic layer was washed with water and saturated brine, dried over anhydrous magnesium sulfate, and concentrated under reduced pressure. To a mixture of the residue and ethyl acetate (80 mL) was added 4 M hydrochloric acid/ethyl acetate solution (6.31 mL) at room temperature, and the mixture was stirred at the same temperature for 3 hr. The solid was recovered, washed with ethyl acetate and dried to give the title compound (2.87 g).

$^1$H NMR (400 MHz, DMSO-d$_6$) δ 4.88 (2H, s), 5.83 (1H, brs), 6.59 (1H, dd, J=2.5, 1.7 Hz), 7.84 (1H, d, J=0.9 Hz), 7.95 (1H, d, J=8.5 Hz), 8.07 (1H, dd, J=8.5, 2.3 Hz), 8.54 (1H, d, J=1.9 Hz), 8.63 (1H, dd, J=2.5, 0.7 Hz).

B) 1,5-anhydro-2,4-dideoxy-2-(7,8-dimethyl-4-oxo-6-((6-(1H-pyrazol-1-yl)pyridin-3-yl)methyl)-2H-1,3-benzoxazin-3(4H)-yl)-L-threo-pentitol To a mixture of 3-((3S,4S)-4-hydroxytetrahydro-2H-pyran-3-yl)-7,8-dimethyl-6-(4,4,5,5-tetramethyl-1,3,2-dioxaborolan-2-yl)-2H-benzo[e][1,3]oxazin-4 (3H)-one (0.06 g), 5-(chloromethyl)-2-(1H-pyrazol-1-yl)pyridine hydrochloride (0.04 g) and 2 M aqueous sodium carbonate solution (0.16 mL) in DME (3 mL)-water (0.3 mL) was added 1,1'-bis(diphenylphosphino)ferrocene palladium (II) chloride (0.01 g), and the mixture was stirred under a nitrogen atmosphere at 90° C. overnight. The reaction mixture was dried over anhydrous sodium sulfate, and concentrated under reduced pressure. The residue was purified by NH silica gel column chromatography (ethyl acetate/hexane) and solidified with ethanol to give the title compound (0.01 g).

$^1$H NMR (300 MHz, DMSO-d$_6$) δ 1.42-1.61 (1H, m), 1.85-1.98 (1H, m), 2.12 (3H, s), 2.18 (3H, s), 3.32-3.51 (2H, m), 3.64-4.00 (4H, m), 4.08 (2H, s), 5.05 (1H, d, J=5.3 Hz), 5.23-5.40 (2H, m), 6.55 (1H, dd, J=2.5, 1.7 Hz), 7.49 (1H, s), 7.66 (1H, dd, J=8.4, 2.4 Hz), 7.79 (1H, dd, J=1.6, 0.7 Hz), 7.85 (1H, d, J=8.3 Hz), 8.31 (1H, d, J=1.7 Hz), 8.57 (1H, dd, J=2.6, 0.6 Hz).

Example 99

8-chloro-3-((1S,2S)-2-hydroxycyclopentyl)-7-methyl-6-((6-(1-methyl-1H-pyrazol-3-yl)pyridin-3-yl)methyl)-2,3-dihydro-4H-1,3-benzoxazin-4-one To a mixture of 8-chloro-6-((6-chloropyridin-3-yl)methyl)-3-((1S,2S)-2-hydroxycyclopentyl)-7-methyl-2,3-dihydro-4H-1,3-benzoxazin-4-one (0.04 g), 1-methyl-3-(4,4,5,5-tetramethyl-1,3,2-dioxaborolan-2-yl)-1H-pyrazole (0.03 g) and 2 M aqueous sodium carbonate solution (0.09 mL) in DME (3 mL)-water (0.3 mL) was added bis(di-tert-butyl(4-dimethylaminophenyl)phosphine)dichloropalladium (II) (0.01 g), and the mixture was subjected to microwave irradiation at 110° C. for 50 min. The reaction mixture was dried over anhydrous sodium sulfate, and concentrated under reduced pressure. The residue was purified by NH silica gel column chromatography (ethyl acetate/hexane) and solidified with ethyl acetate to give the title compound (0.01 g).

$^1$H NMR (300 MHz, DMSO-d$_6$) δ 1.35-1.71 (4H, m), 1.72-1.97 (2H, m), 2.33 (3H, s), 3.89 (3H, s), 3.98-4.08 (1H, m), 4.10 (2H, s), 4.27-4.44 (1H, m), 4.90 (1H, d, J=5.1 Hz), 5.37 (2H, d, J=2.3 Hz), 6.75 (1H, d, J=2.3 Hz), 7.49 (1H, dd, J=8.2, 2.4 Hz), 7.60 (1H, s), 7.74 (1H, d, J=2.3 Hz), 7.82 (1H, d, J=8.1 Hz), 8.42 (1H, d, J=1.7 Hz).

Example 100

1,5-anhydro-2,4-dideoxy-2-(7,8-dimethyl-6-(4-(1-methyl-1H-pyrazol-3-yl)benzyl)-4-oxo-2H-1,3-benzoxazin-3(4H)-yl)-L-threo-pentitol To a mixture of 3-((3S,4S)-4-hydroxytetrahydro-2H-pyran-3-yl)-7,8-dimethyl-6-(4,4,5,5-tetramethyl-1,3,2-dioxaborolan-2-yl)-2H-benzo[e][1,3]oxazin-4(3H)-one (0.06 g), 3-(4-(chloromethyl)phenyl)-1-methyl-1H-pyrazole (0.03 g) and 2 M aqueous sodium carbonate solution (0.16 mL) in DME (3 mL)-water (0.3 mL) was added 1,1'-bis(diphenylphosphino)ferrocene palladium (II) chloride (0.01 g), and the mixture was subjected to microwave irradiation at 110° C. for 50 min. The reaction mixture was dried over anhydrous sodium sulfate and the solvent was evaporated under reduced pressure. The residue was purified by NH silica gel column chromatography (ethyl acetate/hexane) and solidified with ethanol to give the title compound (0.02 g).
$^1$H NMR (300 MHz, DMSO-$d_6$) δ 1.39-1.60 (1H, m), 1.83-1.97 (1H, m), 2.11 (3H, s), 2.16 (3H, s), 3.33-3.54 (2H, m), 3.64-3.74 (1H, m), 3.86 (6H, s), 4.00 (2H, s), 5.06 (1H, d, J=5.3 Hz), 5.20-5.40 (2H, m), 6.61 (1H, d, J=2.1 Hz), 7.12 (2H, d, J=8.3 Hz), 7.46 (1H, s), 7.63-7.73 (3H, m).

Example 101

8-fluoro-3-(2-hydroxy-2-methylpropyl)-7-methyl-6-(4-(1H-pyrazol-1-yl)benzyl)-2,3-dihydro-4H-1,3-benzoxazin-4-one A) 5-(4-(1H-pyrazol-1-yl)benzyl)-3-fluoro-2-hydroxy-N-(2-hydroxy-2-methylpropyl)-4-methylbenzamide To a mixture of 5-(4-(1H-pyrazol-1-yl)benzyl)-3-fluoro-2-hydroxy-4-methylbenzoic acid (0.50 g), 1-amino-2-methylpropan-2-ol (0.14 g), WSC hydrochloride (0.35 g), HOBt monohydrate (0.26 g) and DMF (10 mL) was added triethylamine (0.17 g), and the mixture was stirred at room temperature overnight. To the reaction mixture was added water, and the mixture was extracted with ethyl acetate-isopropyl alcohol (4:1). The organic layer was washed with water and brine, dried over anhydrous magnesium sulfate and concentrated under reduced pressure. The residue was purified by silica gel column chromatography (ethyl acetate/hexane) to give the title compound (0.69 g). This was used in the next step without further purification.
$^1$H NMR (300 MHz, CDCl$_3$) δ 1.26 (6H, s), 2.17 (3H, d, J=2.5 Hz), 3.43 (2H, d, J=5.9 Hz), 3.94 (2H, s), 6.43-6.51 (1H, m), 7.07-7.12 (2H, m), 7.34-7.45 (2H, m), 7.46-7.54 (2H, m), 7.67-7.76 (2H, m), 7.78-7.89 (2H, m).

B) 8-fluoro-3-(2-hydroxy-2-methylpropyl)-7-methyl-6-(4-(1H-pyrazol-1-yl)benzyl)-2,3-dihydro-4H-1,3-benzoxazin-4-one In a sealed tube, to a mixture of 5-(4-(1H-pyrazol-1-yl)benzyl)-3-fluoro-2-hydroxy-N-(2-hydroxy-2-methylpropyl)-4-methylbenzamide (0.61 g), trioxymethylene (0.69 g) and DME (5 mL) was added p-toluenesulfonic acid monohydrate (0.29 g) at room temperature, and the mixture was stirred at 100° C. overnight. The reaction mixture was neutralized with saturated aqueous sodium hydrogen carbonate solution under ice-cooling, and the mixture was extracted with ethyl acetate. The organic layer was washed with water and brine, and dried over anhydrous magnesium sulfate. The solvent was evaporated under reduced pressure. The residue was purified by NH silica gel column chromatography (ethyl acetate/hexane) and solidified with ethyl acetate to give the title compound (0.13 g).
$^1$H NMR (300 MHz, DMSO-$d_6$) δ 1.10 (6H, s), 2.19 (3H, d, J=2.5 Hz), 3.44 (2H, s), 4.04 (2H, s), 4.61 (1H, s), 5.41 (2H, s), 6.52 (1H, dd, J=2.5, 1.7 Hz), 7.27 (2H, d, J=8.7 Hz), 7.41 (1H, d, J=0.9 Hz), 7.70-7.72 (1H, m), 7.73-7.82 (2H, m), 8.44 (1H, d, J=2.1 Hz).

Example 102

1,5-anhydro-2,4-dideoxy-2-(8-fluoro-7-methyl-4-oxo-6-((6-(1H-pyrazol-1-yl)pyridin-3-yl)methyl)-2H-1,3-benzoxazin-3(4H)-yl)-L-threo-pentitol A) 8-fluoro-3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4 (3H)-one To a mixture of 6-bromo-8-fluoro-3-((3S,4S)-4-hydroxytetrahydro-2H-pyran-3-yl)-7-methyl-2H-benzo[e][1,3]oxazin-4(3H)-one (0.51 g), bis(pinacolato)diboron (0.54 g), potassium acetate (0.28 g) and toluene (10 mL) was added dichlorobis(triphenylphosphine)palladium (II) (0.05 g), and the mixture was stirred under an argon atmosphere at 90° C. overnight. Water was added to the reaction mixture at room temperature, and the mixture was extracted with ethyl acetate. The organic layer was washed with water and saturated brine, and dried over anhydrous magnesium sulfate. The solvent was evaporated under reduced pressure. The residue was purified by silica gel column chromatography (ethyl acetate/hexane) to give the title compound (0.34 g).
$^1$H NMR (300 MHz, DMSO-$d_6$) δ 1.31 (12H, s), 1.41-1.59 (1H, m), 1.86-1.97 (1H, m), 2.44 (3H, d, J=3.0 Hz), 3.33-3.50 (2H, m), 3.71 (1H, dd, J=10.9, 4.4 Hz), 3.80-4.05 (3H, m), 5.10 (1H, d, J=5.5 Hz), 5.29-5.53 (2H, m), 7.91 (1H, s).

B) 1,5-anhydro-2,4-dideoxy-2-(8-fluoro-7-methyl-4-oxo-6-((6-(1H-pyrazol-1-yl)pyridin-3-yl)methyl)-2H-1,3-benzoxazin-3(4H)-yl)-L-threo-pentitol To a mixture of 8-fluoro-3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4(3H)-one (0.10 g), 5-(chloromethyl)-2-(1H-pyrazol-1-yl)pyridine hydrochloride (0.07 g), 2 M aqueous sodium carbonate solution (0.25 mL) and DME (3 mL) was added tetrakis(triphenylphosphine)palladium (0) (0.01 g) at room temperature, and the mixture was stirred under an argon atmosphere at 90° C. overnight. The reaction mixture was dried over anhydrous sodium sulfate and the solvent was evaporated under reduced pressure. The residue was purified by NH silica gel column chromatography (ethyl acetate/hexane) to give the title compound (0.05 g).
$^1$H NMR (300 MHz, DMSO-$d_6$) δ 1.35-1.60 (1H, m), 1.86-1.97 (1H, m), 2.21 (3H, brs), 3.32-3.38 (1H, m), 3.45 (1H, t, J=10.8 Hz), 3.70 (1H, dd, J=10.6, 3.8 Hz), 3.76-4.01 (3H, m), 4.09 (2H, s), 5.09 (1H, d, J=4.7 Hz), 5.32-5.47 (2H, m), 6.56 (1H, brs), 7.44 (1H, s), 7.71 (1H, d, J=8.5 Hz), 7.80 (1H, s), 7.87 (1H, d, J=8.5 Hz), 8.34 (1H, brs), 8.55-8.63 (1H, m).

Example 103

1,5-anhydro-2,4-dideoxy-2-(7-methyl-4-oxo-6-((6-(1H-pyrazol-1-yl)pyridin-3-yl)methyl)-2H-1,3-benzoxazin-3(4H)-yl)-L-threo-pentitol A) 5-bromo-2-hydroxy-N-((3S,4S)-4-hydroxytetrahydro-2H-pyran-3-yl)-4-methylbenzamide To a mixture of 5-bromo-2-hydroxy-4-methylbenzoic acid (3.2 g), (3S,4S)-3-aminotetrahydro-2H-pyran-4-ol (1.79 g), WSC hydrochloride (2.92 g), HOBt monohydrate (2.12 g), and DMF (35 mL) was added triethylamine (1.68 g), and the mixture was stirred at room temperature for 7 days. To the reaction mixture was added 1 N hydrochloric acid at room temperature to adjust pH to 4, and the mixture was extracted with ethyl acetate. The organic layer was washed with water and brine, dried over anhydrous magnesium sulfate, and concentrated under reduced pressure. The residue was purified by silica gel column chromatography (ethyl acetate/hexane). 5-bromo-2-hydroxy-4-methylbenzoic acid (1.18 g) was recovered, and the title compound (2.57 g) was obtained. The obtained resultant product was used in the next step without further purification.

MS: [M+H]$^+$ 329.9
$^1$H NMR (300 MHz, DMSO-d$_6$) δ 1.41-1.57 (1H, m), 1.85-1.95 (1H, m), 2.31 (3H, s), 3.01-3.17 (1H, m), 3.33-3.43 (1H, m), 3.63-3.88 (4H, m), 5.04 (1H, d, J=4.9 Hz), 6.92 (1H, s), 8.14 (1H, s), 8.58 (1H, d, J=7.4 Hz), 12.52 (1H, brs).

B) 6-bromo-3-((3S,4S)-4-hydroxytetrahydro-2H-pyran-3-yl)-7-methyl-2H-benzo[e][1,3]oxazin-4(3H)-one To a mixture of 5-bromo-2-hydroxy-N-((3S,4S)-4-hydroxytetrahydro-2H-pyran-3-yl)-4-methylbenzamide (2.57 g), paraformaldehyde (0.70 g), and toluene (20 mL) was added p-toluenesulfonic acid monohydrate (0.30 g) at room temperature, and the mixture was stirred at 60° C. overnight. The reaction mixture was neutralized with saturated aqueous sodium hydrogen carbonate solution at 0° C., and extracted with ethyl acetate. The organic layer was washed with water and brine, and dried over anhydrous magnesium sulfate. The solvent was evaporated under reduced pressure. The residue was purified by NH silica gel column chromatography (ethyl acetate/hexane) and solidified with ethyl acetate to give the title compound (0.87 g).

MS: [M+H]$^+$ 341.9, 343.9
$^1$H NMR (300 MHz, DMSO-d$_6$) δ 1.39-1.61 (1H, m), 1.84-1.96 (1H, m), 2.37 (3H, s), 3.31-3.39 (1H, m), 3.45 (1H, t, J=10.7 Hz), 3.70 (1H, dd, J=11.0, 4.3 Hz), 3.77-4.08 (3H, m), 5.09 (1H, d, J=5.3 Hz), 5.21-5.41 (2H, m), 7.13 (1H, s), 7.87 (1H, s).

C) 3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4 (3H)-one To a mixture of 6-bromo-3-((3S,4S)-4-hydroxytetrahydro-2H-pyran-3-yl)-7-methyl-2H-benzo[e][1,3]oxazin-4 (3H)-one (0.87 g), bis(pinacolato)diboron (0.97 g), potassium acetate (0.50 g), and toluene (10 mL) was added dichlorobis(triphenylphosphine)palladium (II) (0.09 g) at room temperature, and the mixture was stirred under an argon atmosphere at 90° C. overnight. To the reaction mixture was added water at room temperature, and the mixture was extracted with ethyl acetate. The organic layer was washed with water and brine, dried over anhydrous magnesium sulfate, and concentrated under reduced pressure. The residue was purified by silica gel column chromatography (ethyl acetate/hexane) to give the title compound (0.82 g).

MS: [M+H]$^+$ 390.1
$^1$H NMR (300 MHz, DMSO-d$_6$) δ 1.30 (12H, s), 1.40-1.67 (1H, m), 1.80-1.96 (1H, m), 2.48 (3H, brs), 3.33-3.52 (2H, m), 3.69 (1H, dd, J=10.8, 4.5 Hz), 3.76-3.90 (2H, m), 3.93-4.07 (1H, m), 5.07 (1H, d, J=5.5 Hz), 5.21-5.43 (2H, m), 6.87 (1H, s), 8.10 (1H, s).

D) 1,5-anhydro-2,4-dideoxy-2-(7-methyl-4-oxo-6-((6-(1H-pyrazol-1-yl)pyridin-3-yl)methyl)-2H-1,3-benzoxazin-3(4H)-yl)-L-threo-pentitol To a mixture of 3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4(3H)-one (0.10 g), 5-(chloromethyl)-2-(1H-pyrazol-1-yl)pyridine hydrochloride (0.07 g), tetrakis(triphenylphosphine)palladium (0) (0.01 g) and DME (3 mL) was added 2 M aqueous sodium carbonate solution (0.26 mL) at room temperature, and the mixture was stirred under an argon atmosphere at 80° C. overnight. The reaction mixture was diluted with ethyl acetate and dried over anhydrous magnesium sulfate, and the solvent was evaporated under reduced pressure. The residue was purified by silica gel column chromatography (ethyl acetate/hexane) and solidified with ethanol to give the title compound (0.07 g).

$^1$H NMR (300 MHz, DMSO-d$_6$) δ 1.38-1.63 (1H, m), 1.83-2.00 (1H, m), 2.27 (3H, s), 3.31-3.50 (2H, m), 3.69 (1H, dd, J=10.9, 4.4 Hz), 3.77-4.02 (3H, m), 4.04 (2H, s), 5.05 (1H, d, J=5.3 Hz), 5.21-5.40 (2H, m), 6.56 (1H, dd, J=2.6, 1.7 Hz), 6.92 (1H, s), 7.56 (1H, s), 7.69 (1H, dd, J=8.5, 2.3 Hz), 7.79 (1H, dd, J=1.5, 0.6 Hz), 7.87 (1H, d, J=8.3 Hz), 8.32 (1H, d, J=1.9 Hz), 8.55-8.61 (1H, m).

Example 104-1

3-((3S,4S)-4-hydroxytetrahydro-2H-pyran-3-yl)-7-methyl-6-(4-(1-methyl-1H-pyrazol-3-yl)benzyl)-2,3-dihydro-4H-1,3-benzoxazin-4-one Alias; 1,5-anhydro-2,4-dideoxy-2-(7-methyl-6-(4-(1-methyl-1H-pyrazol-3-yl)benzyl)-4-oxo-2H-1,3-benzoxazin-3(4H)-yl)-L-threo-pentitol To a mixture of 3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4(3H)-one (0.10 g), 3-(4-(chloromethyl)phenyl)-1-methyl-1H-pyrazole (0.06 g), tetrakis(triphenylphosphine)palladium (0) (15 mg), and DME (3 mL) was added 2 M aqueous sodium carbonate solution (0.26 mL) at room temperature, and the mixture was stirred under an argon atmosphere at 80° C. overnight. The reaction mixture was diluted with ethyl acetate, and dried over anhydrous magnesium sulfate. The solvent was evaporated under reduced pressure. The residue was purified by silica gel column chromatography (ethyl acetate/hexane) and crystallized from ethyl acetate to give the title compound (0.05 g).

¹H NMR (300 MHz, DMSO-d₆) δ 1.33-1.64 (1H, m), 1.81-1.96 (1H, m), 2.24 (3H, s), 3.31-3.50 (2H, m), 3.64-3.73 (1H, m), 3.75-3.84 (1H, m), 3.86 (3H, s), 3.87-4.01 (4H, m), 5.06 (1H, d, J=5.3 Hz), 5.18-5.39 (2H, m), 6.62 (1H, d, J=2.3 Hz), 6.89 (1H, s), 7.14 (2H, d, J=8.3 Hz), 7.54 (1H, s), 7.65-7.73 (3H, m).

Example 104-2

3-((3S,4S)-4-hydroxytetrahydro-2H-pyran-3-yl)-7-methyl-6-(4-(1-methyl-1H-pyrazol-3-yl)benzyl)-2,3-dihydro-4H-1,3-benzoxazin-4-one Alias; 1,5-anhydro-2,4-dideoxy-2-(7-methyl-6-(4-(1-methyl-1H-pyrazol-3-yl)benzyl)-4-oxo-2H-1,3-benzoxazin-3(4H)-yl)-L-threo-pentitol A) 5-bromo-2-hydroxy-N-((3S,4S)-4-hydroxytetrahydro-2H-pyran-3-yl)-4-methylbenzamide To a stirred mixture of 5-bromo-2-hydroxy-4-methylbenzoic acid (50 g), (3S,4S)-3-aminotetrahydro-2H-pyran-4-ol (28 g), WSC hydrochloride (45 g), HOBt (33 g), and DMF (500 mL) was added triethylamine (37 mL) at room temperature, and the reaction mixture was stirred at room temperature for 16 hr. The reaction mixture was then heated to 60° C. for 2 hr. The reaction mixture was quenched with ice water and extracted with ethyl acetate. The organic layer was washed with water and brine, dried over anhydrous sodium sulfate, filtered, evaporated under reduced pressure, and washed with n-pentane and diethyl ether to give the title compound (50 g). The obtained resultant product was used in the next step without further purification.
MS: [M+H]⁺ 329.9, 331.9.

B) 6-bromo-3-((3S,4S)-4-hydroxytetrahydro-2H-pyran-3-yl)-7-methyl-2H-benzo[e][1,3]oxazin-4(3H)-one To a stirred mixture of 5-bromo-2-hydroxy-N-((3S,4S)-4-hydroxytetrahydro-2H-pyran-3-yl)-4-methylbenzamide (50 g), paraformaldehyde (14 g), and toluene (500 mL) was added p-toluenesulfonic acid monohydrate (5.8 g) at room temperature, and the reaction mixture was heated to 60° C. for 16 hr. The reaction mixture was cooled to room temperature, neutralized with saturated aqueous sodium hydrogen carbonate solution at 0° C., and then extracted with ethyl acetate. The organic layer was separated, washed with water and brine, dried over anhydrous sodium sulfate, filtered, and evaporated under reduced pressure. The residue was purified by NH silica gel column chromatography (ethyl acetate/petroleum ether) to give the title compound (17 g).
MS: [M+H]⁺ 342.1.

C) 3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4 (3H)-one To a stirred and degassed mixture of 6-bromo-3-((3S,4S)-4-hydroxytetrahydro-2H-pyran-3-yl)-7-methyl-2H-benzo[e][1,3]oxazin-4(3H)-one (17 g), bis(pinacolato)diboron (19 g), potassium acetate (9.8 g), and toluene (200 mL) was added dichlorobis(triphenylphosphine)palladium (II) (1.7 g) at room temperature, and the reaction mixture was heated to 90° C. under an argon atmosphere for 16 hr. The reaction mixture was quenched with water and extracted with ethyl acetate. The organic layer was washed with water and brine, dried over anhydrous sodium sulfate, filtered, and evaporated under reduced pressure. The residue was purified by silica gel column chromatography (ethyl acetate/petroleum ether) to afford the title compound (12 g).
MS: [M+H]⁺ 390.3.

D) 3-((3S,4S)-4-hydroxytetrahydro-2H-pyran-3-yl)-7-methyl-6-(4-(1-methyl-1H-pyrazol-3-yl)benzyl)-2,3-dihydro-4H-1,3-benzoxazin-4-one Alias; 1,5-anhydro-2,4-dideoxy-2-(7-methyl-6-(4-(1-methyl-1H-pyrazol-3-yl)benzyl)-4-oxo-2H-1,3-benzoxazin-3(4H)-yl)-L-threo-pentitol To a stirred and degassed mixture of 3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4(3H)-one (10 g), 3-(4-(chloromethyl)phenyl)-1-methyl-H-pyrazole (6.4 g), 1,1'-bis(diphenylphosphino)ferrocene palladium (II) chloride dichloromethane complex (1.0 g), and DME (125 mL) was added 2 M aqueous sodium carbonate solution (27 mL) at room temperature, and the reaction mixture was heated to 80° C. under an argon atmosphere for 16 hr. The reaction mixture was quenched with water and extracted with ethyl acetate. The organic layer was washed with water and brine, dried over anhydrous sodium sulfate, filtered, and evaporated under reduced pressure. The residue was purified by silica gel column chromatography (methanol/ethyl acetate) and washed with 10% methanol/ethyl acetate. The same reaction was performed on 5.0 g scale to get 8.6 g of the residue in total. The residue was further treated with NH silica gel (80 g) in 10% methanol/ethyl acetate (80 mL). The resultant slurry was stirred at room temperature for 1 hr and filtered. The filtrate was dried. The same procedure using NH silica gel was repeated for three times to get a crude product (8.4 g). A mixture of the crude product (8.1 g) and ethanol (162 mL) was stirred at 60° C. for 1 hr. Insoluble materials were removed by hot filtration and washed with a small amount of ethanol. The filtrate was heated to 60° C. with stirring, and heptane (300 mL) was added dropwise. The mixture was stirred at 60° C. for 1 hr and allowed to be cooled to room temperature overnight. The precipitates were collected by filtration and washed with heptane/ethanol=2/1 solution to give the title compound (7.0 g).
¹H NMR (30.0 MHz, DMSO-d₆) δ 1.41-1.58 (1H, m), 1.85-1.96 (1H, m), 2.24 (3H, s), 3.26-3.38 (1H, m), 3.44 (1H, t, J=10.7 Hz), 3.69 (1H, dd, J=10.8, 4.4 Hz), 3.75-4.03 (8H, m), 5.06 (1H, d, J=5.3 Hz), 5.24 (1H, d, J=8.8 Hz), 5.31 (1H, d, J=9.5 Hz), 6.62 (1H, d, J=2.3 Hz), 6.89 (1H, s), 7.14 (2H, d, J=8.3 Hz), 7.54 (1H, s), 7.66-7.73 (3H, m).
The obtained crystal was characterized by having specific peaks at the two theta of 10.2°±0.2°, 10.7°±0.2°, 13.8°±0.2°, 16.2°±0.2°, 17.1°±0.2°, 17.8°±0.2°, 23.2°±0.2° and 27.1°±0.2° degrees in a powder X-ray diffraction pattern.

Example 105

8-fluoro-3-((1S,2S)-2-hydroxycyclopentyl)-7-methyl-6-(4-(6-methylpyridazin-4-yl)benzyl)-2,3-dihydro-4H-1,3-benzoxazin-4-one Hydrochloride A) 5-iodo-2-((2-(trimethylsilyl)ethoxy)methyl)pyridazin-3(2H)-one To a mixture of 5-iodopyridazin-3(2H)-one (14.0 g) and DMF (150 mL) were added dropwise diisopropylethylamine (16.3 g) and (2-(trimethylsilyl)ethoxymethyl chloride (21.0 g) under ice-cooling, and the mixture was stirred at 15° C. for 16 hr. The solvent was evaporated under reduced pressure, and the residue was diluted with ethyl acetate. The organic layer was washed with water and brine, dried over anhydrous sodium sulfate, and concentrated under reduced pressure. The residue was purified by silica gel column chromatography (ethyl acetate/petroleum ether) to give the title compound (17.9 g).

$^1$H NMR (400 MHz, CDCl$_3$) δ 0.00 (9H, s), 0.96 (2H, t, J=8.4 Hz), 3.69 (2H, t, J=8.4 Hz), 5.41 (2H, s), 7.48 (1H, d, J=2.0 Hz), 7.93 (1H, d, J=2.0 Hz).

B) Methyl 4-(6-oxo-1-((2-(trimethylsilyl)ethoxy)methyl)-1,6-dihydropyridazin-4-yl)benzoate A mixture of 5-iodo-2-((2-(trimethylsilyl)ethoxy)methyl)pyridazin-3(2H)-one (17.9 g), 4-methoxycarbonylphenylboronic acid (11.0 g), tetrakis(triphenylphosphine)palladium (0) (2.94 g) and sodium carbonate (10.8 g) in DME (150 mL)-water (15 mL) was stirred under a nitrogen atmosphere at 90° C. for 16 hr. The reaction mixture was concentrated under reduced pressure, and the residue was diluted with ethyl acetate. The mixture was washed with water and saturated brine, dried over anhydrous sodium sulfate, and concentrated under reduced pressure. The residue was purified by silica gel column chromatography (ethyl acetate/petroleum ether), 5-iodo-2-((2-(trimethylsilyl)ethoxy)methyl)pyridazin-3(2H)-one (6.00 g) was recovered and the title compound (11.0 g) was obtained.

$^1$H NMR (400 MHz, CDCl$_3$) δ 0.00 (9H, s), 0.99 (2H, t, J=8.4 Hz), 3.75 (2H, t, J=8.4 Hz), 3.96 (3H, s), 5.53 (2H, s), 7.11 (1H, d, J=2.4 Hz), 7.65 (2H, d, J=8.4 Hz), 8.09 (1H, d, J=2.0 Hz), 8.17 (2H, d, J=8.4 Hz).

C) Methyl 4-(6-oxo-1,6-dihydropyridazin-4-yl)benzoate

To a mixture of methyl 4-(6-oxo-1-((2-(trimethylsilyl)ethoxy)methyl)-1,6-dihydropyridazin-4-yl)benzoate (13.8 g) and methanol (300 mL) was added concentrated hydrochloric acid (40 mL), and the mixture was stirred with heating under reflux for 16 hr. The reaction mixture was cooled to room temperature. The resulting precipitates were collected by filtration. The solid was washed with methanol and dried under reduced pressure to give the title compound (6.77 g).

$^1$H NMR (400 MHz, DMSO-d$_6$) δ 3.89 (3H, s), 7.23 (1H, s), 7.97 (2H, d, J=8.0 Hz), 8.06 (2H, d, J=8.4 Hz), 8.33 (1H, d, J=2.0 Hz), 13.20 (1H, brs).

D) methyl 4-(6-bromopyridazin-4-yl)benzoate

A mixture of methyl 4-(6-oxo-1,6-dihydropyridazin-4-yl)benzoate (6.77 g) and phosphoryl bromide (25.3 g) was stirred under a nitrogen atmosphere at 80° C. for 16 hr. Before cooling, the reaction mixture was poured into water, and the mixture was stirred under ice-cooling for 2 hr. The aqueous layer was neutralized with saturated aqueous sodium hydrogen carbonate solution, and extracted 5 times with dichloromethane. The organic layer was washed with saturated brine, dried over anhydrous sodium sulfate, and the solvent was evaporated under reduced pressure to give the title compound (7.80 g).

$^1$H NMR (400 MHz, DMSO-d$_6$) δ 3.90 (3H, s), 8.10 (2H, d, J=8.4 Hz), 8.13 (2H, d, J=8.8 Hz), 8.47 (1H, d, J=2.0 Hz), 9.73 (1H, d, J=2.0 Hz).

E) Methyl 4-(6-methylpyridazin-4-yl)benzoate

To a mixture of methyl 4-(6-bromopyridazin-4-yl)benzoate (6.80 g), iron (III) acetylacetonate (0.82 g) and THF (200 mL) was added 3 M methyl magnesium bromide/diethyl ether solution (11.6 mL) under a nitrogen atmosphere at 0° C., and the mixture was stirred at 20° C. for 16 hr. To the reaction mixture was added saturated aqueous ammonium chloride solution at 0° C. and the mixture was filtered. The aqueous layer of the filtrate was extracted 5 times with ethyl acetate, and the organic layer was washed with saturated brine, dried over anhydrous sodium sulfate, and the solvent was evaporated under reduced pressure. The aqueous layer was further extracted 3 times with dichloroethane, and the organic layer was washed with saturated brine, dried over anhydrous sodium sulfate, and the solvent was evaporated under reduced pressure. The combined residue was purified by silica gel column chromatography (ethyl acetate/petroleum ether) to give the title compound (3.66 g).

$^1$H NMR (400 MHz, CDCl$_3$) δ 2.81 (3H, s), 3.97 (3H, s), 7.53 (1H, d, J=2.0 Hz), 7.73 (2H, d, J=8.4 Hz), 8.19 (2H, d, J=8.0 Hz), 9.32 (1H, d, J=1.6 Hz).

F) 4-(6-methylpyridazin-4-yl)benzoic Acid

A mixture of methyl 4-(6-methylpyridazin-4-yl)benzoate (4.37 g) and lithium hydroxide monohydrate (3.22 g) in THF (50 mL)-water (10 mL) was stirred at 20° C. for 16 hr. The solvent was almost evaporated under reduced pressure, and the residue was diluted with water and extracted 3 times with ethyl acetate. The aqueous layer was filtered, and the filtrate was adjusted to pH=5 with saturated aqueous citric acid solution. The precipitates were collected by filtration, washed with water and freeze-dried to give the title compound (4.10 g). The resultant product was used in the next step without further purification.

$^1$H NMR (400 MHz, DMSO-d$_6$) δ 2.69 (3H, s), 7.96 (1H, d, J=2.0 Hz), 8.01 (2H, d, J=8.4 Hz), 8.08 (2H, d, J=8.0 Hz), 9.50 (1H, d, J=2.0 Hz). 1H was not observed.

G) (4-(6-methylpyridazin-4-yl)phenyl)methanol

To a mixture of 4-(6-methylpyridazin-4-yl)benzoic acid (3.10 g) and THF (120 mL) were added triethylamine (2.20 g) and isobutyl chloroformate (2.18 g) under a nitrogen atmosphere at 0° C., and the mixture was stirred for 1 hr. To this reaction mixture was added a mixture of sodium borohydride (1.65 g) and water (4 mL), and the mixture was stirred at the same temperature for 2 hr. To the reaction mixture was added saturated aqueous ammonium chloride solution, and the mixture was extracted 4 times with ethyl acetate. The organic layer was washed with saturated brine, dried over anhydrous sodium sulfate, and the solvent was evaporated under reduced pressure. The residue was purified by silica gel column chromatography (ethyl acetate/petroleum ether) to give the title compound (0.92 g).

$^1$H NMR (400 MHz, CDCl$_3$) δ 2.14 (1H, brs), 2.78 (3H, s), 4.80 (2H, s), 7.49 (1H, d, J=2.4 Hz), 7.54 (2H, d, J=8.0 Hz), 7.66 (2H, d, J=8.0 Hz), 9.27 (1H, d, J=2.0 Hz).

H) 5-(4-(bromomethyl)phenyl)-3-methylpyridazine

To a mixture of (4-(6-methylpyridazin-4-yl)phenyl)methanol (0.46 g) and dichloromethane (25 mL) was added dropwise phosphorus tribromide (0.61 g) at 0° C., and the mixture was stirred at 20° C. for 16 hr. The resulting precipitates were collected by filtration, and washed with dichloromethane. The isolated solid was dried under reduced pressure to give the title compound (0.92 g).

$^1$H NMR (400 MHz, DMSO-d$_6$) δ 2.80 (3H, s), 4.81 (2H, s), 7.71 (2H, d, J=8.8 Hz), 8.07 (2H, d, J=8.4 Hz), 8.56 (1H, s), 9.76 (1H, d, J=2.0 Hz).

I) 8-fluoro-3-((1S,2S)-2-hydroxycyclopentyl)-7-methyl-6-(4-(6-methylpyridazin-4-yl)benzyl)-2,3-dihydro-4H-1,3-benzoxazin-4-one To a mixture of 8-fluoro-3-((1S,2S)-2-hydroxycyclopentyl)-7-methyl-6-(4,4,5,5-tetramethyl-1,3,2-dioxaborolan-2-yl)-2H-benzo[e][1,3]oxazin-4(3H)-one (0.09 g), 5-(4-(bromomethyl)phenyl)-3-methylpyridazine (0.07 g), tetrakis(triphenylphosphine)palladium (0) (0.01 g) and DME (3 mL) was added 2 M aqueous sodium carbonate solution (0.23 mL) at room temperature, and the mixture was stirred under an argon atmosphere at 80° C. overnight. The reaction mixture was diluted with ethyl acetate, dried over anhydrous magnesium sulfate, and the solvent was evaporated under reduced pressure. The residue was purified by NH silica gel column chromatography (ethyl acetate/hexane to methanol/ethyl acetate) and solidified with ethanol to give the title compound (0.02 g).

MS: [M+H]$^+$ 448.1

J) 8-fluoro-3-((1S,2S)-2-hydroxycyclopentyl)-7-methyl-6-(4-(6-methylpyridazin-4-yl)benzyl)-2,3-dihydro-4H-1,3-benzoxazin-4-one Hydrochloride To a mixture of 8-fluoro-3-((1S,2S)-2-hydroxycyclopentyl)-7-methyl-6-(4-(6-methylpyridazin-4-yl)benzyl)-2,3-dihydro-4H-1,3-benzoxazin-4-one (0.02 g) and ethyl acetate (3 mL) was added 4 M hydrochloric acid/ethyl acetate solution (0.02 mL), and the mixture was stirred at room temperature for 10 min. The precipitates were collected by filtration, and dried under reduced pressure to give the title compound (0.01 g).

$^1$H NMR (300 MHz, DMSO-d$_6$) δ 1.36-1.51 (1H, m), 1.55-1.73 (3H, m), 1.75-1.94 (3H, m), 2.15-2.24 (3H, m), 2.75 (3H, s), 4.09-4.17 (2H, m), 4.27-4.45 (1H, m), 5.32-5.39 (2H, m), 7.23-7.53 (3H, m), 7.96 (2H, d, J=7.9 Hz), 8.31 (1H, brs), 9.64 (1H, s), 2H was not observed.

Example 106

1,5-anhydro-2-(8-chloro-7-methyl-4-oxo-6-((6-(1H-pyrazol-1-yl)pyridin-3-yl)methyl)-2H-1,3-benzoxazin-3(4H)-yl)-2,4-dideoxy-L-threo-pentitol A) 8-chloro-3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4 (3H)-one To a mixture of 6-bromo-8-chloro-3-((3S,4S)-4-hydroxytetrahydro-2H-pyran-3-yl)-7-methyl-2H-benzo[e][1,3]oxazin-4(3H)-one (0.49 g), bis(pinacolato)diboron (0.49 g), potassium acetate (0.25 g) and toluene (10 mL) was added dichlorobis(triphenylphosphine)palladium (II) (0.05 g) at room temperature, and the mixture was stirred under an argon atmosphere at 100° C. for 1 day. The reaction mixture was filtered through celite, saturated aqueous sodium hydrogen carbonate solution was added to the filtrate at room temperature, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.40 g).

$^1$H NMR (300 MHz, DMSO-d$_6$) δ 1.32 (12H, s), 1.44-1.64 (1H, m), 1.84-1.98 (1H, m), 2.58 (3H, s), 3.33-3.53 (2H, m), 3.71 (1H, dd, J=10.9, 4.2 Hz), 3.78-3.87 (1H, m), 3.92-4.11 (2H, m), 5.10 (1H, d, J=5.3 Hz), 5.37-5.51 (2H, m), 8.07 (1H, s).

B) 1,5-anhydro-2-(8-chloro-7-methyl-4-oxo-6-((6-(1H-pyrazol-1-yl)pyridin-3-yl)methyl)-2H-1,3-benzoxazin-3(4H)-yl)-2,4-dideoxy-L-threo-pentitol To a mixture of 8-chloro-3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4(3H)-one (0.15 g), 5-(chloromethyl)-2-(1H-pyrazol-1-yl)pyridine hydrochloride (0.10 g), 2 M aqueous sodium carbonate solution (0.35 mL) and DME (3 mL) was added tetrakis(triphenylphosphine)palladium (0) (0.02 g) under an argon atmosphere at room temperature, and the mixture was stirred at 90° C. overnight. The reaction mixture was dried over anhydrous sodium sulfate, and the solvent was evaporated under reduced pressure. The residue was purified by silica gel column chromatography (ethyl acetate/hexane) and solidified with ethanol to give the title compound (0.07 g).

$^1$H NMR (300 MHz, DMSO-d$_6$) δ 1.37-1.65 (1H, m), 1.83-2.00 (1H, m), 2.34 (3H, s), 3.32-3.38 (1H, m), 3.39-3.54 (1H, m), 3.64-4.02 (4H, m), 4.14 (2H, s), 5.10 (1H, d, J=5.1 Hz), 5.30-5.54 (2H, m, J=10.6 Hz), 6.56 (1H, dd, J=2.5, 1.7 Hz), 7.61 (1H, s), 7.69 (1H, dd, J=8.5, 2.3 Hz), 7.80 (1H, d, J=1.1 Hz), 7.87 (1H, d, J=8.5 Hz), 8.33 (1H, d, J=1.9 Hz), 8.58 (1H, d, J=2.5 Hz).

Example 107

1,5-anhydro-2,4-dideoxy-2-(7-ethyl-4-oxo-6-(4-(1H-pyrazol-1-yl)benzyl)-2H-1,3-benzoxazin-3(4H)-yl)-L-threo-pentitol A) Methyl 4-bromo-2-hydroxybenzoate To a mixture of 4-bromo-2-hydroxybenzoic acid (5.0 g) in toluene (80 mL)-methanol (20 mL) was added dropwise 0.6 M (diazomethyl)trimethylsilane (38 mL) under ice-cooling. The reaction mixture was stirred at the same temperature for 2 hr. The reaction mixture was acidified with acetic acid (0.35 mL), and concentrated under reduced pressure, and the residue was purified by silica gel column chromatography (ethyl acetate/hexane) to give the title compound (4.83 g).

$^1$H NMR (300 MHz, CDCl$_3$) δ 3.95 (3H, s), 7.02 (1H, dd, J=8.7, 1.9 Hz), 7.18 (1H, d, J=1.9 Hz), 7.68 (1H, d, J=8.3 Hz), 10.82 (1H, s).

B) Methyl 2-hydroxy-4-vinylbenzoate

A mixture of methyl 4-bromo-2-hydroxybenzoate (3.0 g), tributylvinyltin (6.18 g), dichlorobis(triphenylphosphine)palladium (II) (0.46 g), lithium chloride (4.07 g) and DMF (50 mL) was stirred under an argon atmosphere at 90° C. for 2 hr. To the reaction mixture was added aqueous potassium fluoride solution, and the precipitated insoluble material was filtered off through celite. The filtrate was diluted with ethyl acetate, and washed with water and saturated brine. The organic layer was dried over anhydrous sodium sulfate, and the solvent was evaporated under reduced pressure. The residue was purified by silica gel column chromatography (ethyl acetate/hexane) to give the title compound. This was used in the next step without further purification.

C) Methyl 4-ethyl-2-hydroxybenzoate

To a mixture of methyl 2-hydroxy-4-vinylbenzoate (2.31 g) and ethanol (25.0 mL) was added 10% palladium-carbon (1.38 g), and the mixture was stirred under a hydrogen atmosphere at room temperature overnight. The insoluble material was filtered off, the filtrate was concentrated under reduced pressure, and the obtained residue was purified by NH silica gel column chromatography (ethyl acetate/hexane) to give the title compound (1.43 g).
MS: [M+H]$^+$ 181.1

D) Methyl 5-bromo-4-ethyl-2-hydroxybenzoate

To a mixture of methyl 4-ethyl-2-hydroxybenzoate (1.43 g) and acetic acid (15.0 mL) was added under ice-cooling bromine (1.40 g), and the mixture was stirred under an argon atmosphere at room temperature for 2 hr. To the reaction mixture was added water, the resultant product was collected by filtration, and the obtained solid was dried under reduced pressure to give the title compound (2.21 g) as a 2:1 mixture with methyl 3,5-dibromo-4-ethyl-2-hydroxybenzoate. This was used in the next step without further purification.

E) Methyl 4-ethyl-2-hydroxy-5-(4,4,5,5-tetramethyl-1,3,2-dioxaborolan-2-yl)benzoate A mixture of a mixture (1.00 g) of methyl 5-bromo-4-ethyl-2-hydroxybenzoate and methyl 3,5-dibromo-4-ethyl-2-hydroxybenzoate, bis(pinacolato)diboron (1.47 g), potassium acetate (1.14 g), dichlorobis(triphenylphosphine)palladium (II) (0.14 g) and toluene (20.0 mL) was stirred under an argon atmosphere at 100° C. overnight. The reaction mixture was diluted with ethyl acetate, washed with saturated brine, dried over anhydrous sodium sulfate, and the solvent was evaporated under reduced pressure. The residue was purified by silica gel column chromatography (ethyl acetate/hexane) to give the title compound (0.82 g). This was used in the next step without further purification.
MS: [M+H]$^+$ 307.2

F) Methyl 5-(4-(1H-pyrazol-1-yl)benzyl)-4-ethyl-2-hydroxybenzoate

To a mixture of methyl 4-ethyl-2-hydroxy-5-(4,4,5,5-tetramethyl-1,3,2-dioxaborolan-2-yl)benzoate (0.54 g), 1-(4-(chloromethyl)phenyl)-1H-pyrazole (0.41 g), 2 M aqueous sodium carbonate solution (1.76 mL) and DME (20 mL) was added tetrakis(triphenylphosphine)palladium (0) (0.10 g) under an argon atmosphere at room temperature, and the mixture was stirred at 90° C. overnight. The reaction mixture was dried over anhydrous sodium sulfate, and the solvent was evaporated under reduced pressure. The residue was purified by silica gel column chromatography (ethyl acetate/hexane) to give the title compound (0.45 g).
MS: [M+H]$^+$ 337.0

G) 5-(4-(1H-pyrazol-1-yl)benzyl)-4-ethyl-2-hydroxybenzoic Acid

To a mixture of methyl 5-(4-(1H-pyrazol-1-yl)benzyl)-4-ethyl-2-hydroxybenzoate (0.45 g) in methanol (3 mL)-THF (3 mL) was added 8 M aqueous sodium hydroxide solution (1.67 mL), and the mixture was stirred at room temperature overnight. To the reaction mixture was added under ice-cooling 6 M hydrochloric acid (pH 4), and the mixture was extracted with ethyl acetate. The organic layer was washed with water and saturated brine, dried over anhydrous magnesium sulfate, and the solvent was evaporated under reduced pressure to give the title compound (0.42 g).
MS: [M+H]$^+$ 323.0

H) 5-(4-(1H-pyrazol-1-yl)benzyl)-4-ethyl-2-hydroxy-N-((3S,4S)-4-hydroxytetrahydro-2H-pyran-3-yl)benzamide To a mixture of 5-(4-(1H-pyrazol-1-yl)benzyl)-4-ethyl-2-hydroxybenzoic acid (0.42 g), (3S,4S)-3-aminotetrahydro-2H-pyran-4-ol (0.17 g), WSC hydrochloride (0.33 g), HOBt monohydrate (0.33 g) and DMSO (5 mL) was added triethylamine (0.19 g), and the mixture was stirred at room temperature overnight. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.44 g).
MS: [M+H]$^+$ 422.1

I) 1,5-anhydro-2,4-dideoxy-2-(7-ethyl-4-oxo-6-(4-(1H-pyrazol-1-yl)benzyl)-2H-1,3-benzoxazin-3(4H)-yl)-L-threo-pentitol To a mixture of 5-(4-(1H-pyrazol-1-yl)benzyl)-4-ethyl-2-hydroxy-N-((3S,4S)-4-hydroxytetrahydro-2H-pyran-3-yl)benzamide (0.10 g), paraformaldehyde (0.02 g) and DME (10 mL) was added p-toluenesulfonic acid monohydrate (0.01 g) at room temperature, and the mixture was stirred at 60° C. for the week end. The reaction mixture was neutralized with saturated aqueous sodium hydrogen carbonate solution under ice-cooling, and extracted with ethyl acetate. The organic layer was washed with water and brine, and dried over anhydrous magnesium sulfate. The solvent was evaporated under reduced pressure. The residue was purified by NH silica gel column chromatography (ethyl acetate/hexane) and solidified with ethyl acetate to give the title compound (0.01 g).
$^1$H NMR (300 MHz, DMSO-d$_6$) δ 1.08 (3H, t, J=7.6 Hz), 1.35-1.62 (1H, m), 1.82-1.97 (1H, m), 2.61 (2H, q, J=7.6 Hz), 3.32-3.39 (1H, m), 3.39-3.52 (1H, m), 3.63-3.74 (1H, m), 3.76-3.99 (3H, m), 4.00-4.08 (2H, m), 5.05 (1H, d, J=5.3 Hz), 5.20-5.40 (2H, m), 6.49-6.54 (1H, m), 6.89 (1H, s), 7.24 (2H, d, J=8.7 Hz), 7.55 (1H, s), 7.71 (1H, d, J=1.3 Hz), 7.72-7.82 (2H, m), 8.43 (1H, d, J=2.1 Hz).

Example 108

1,5-anhydro-2,4-dideoxy-2-(8-fluoro-7-methyl-6-(4-(1-methyl-1H-pyrazol-3-yl)benzyl)-4-oxo-2H-1,3-benzoxazin-3(4H)-yl)-L-threo-pentitol To a mixture of 8-fluoro-3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4(3H)-one (0.10 g), 3-(4-(chloromethyl)phenyl)-1-methyl-1H-pyrazole hydrochloride (0.07 g), 2 M aqueous sodium carbonate solution (0.25 mL) and DME (3 mL) was added tetrakis (triphenylphosphine)palladium (0) (0.01 g) under an argon atmosphere at room temperature, and the mixture was stirred at 90° C. overnight. The reaction mixture was dried over anhydrous sodium sulfate, and concentrated under reduced pressure. The residue was purified by NH silica gel column chromatography (ethyl acetate/hexane) and solidified with ethyl acetate to give the title compound (0.05 g).

$^1$H NMR (300 MHz, DMSO-d$_6$) δ 1.38-1.58 (1H, m), 1.84-1.97 (1H, m), 2.18 (3H, d, J=2.5 Hz), 3.31-3.39 (1H, m), 3.40-3.51 (1H, m), 3.71 (1H, dd, J=11.0, 4.3 Hz), 3.76-3.85 (1H, m), 3.86 (3H, s), 3.87-3.98 (2H, m), 3.99-4.03 (2H, m), 5.09 (1H, d, J=5.1 Hz), 5.27-5.48 (2H, m), 6.62 (1H, d, J=2.3 Hz), 7.15 (2H, d, J=8.1 Hz), 7.41 (1H, s), 7.64-7.75 (3H, m).

Example 109

1,5-anhydro-2-(8-chloro-6-((6-methoxypyridin-3-yl) methyl)-7-methyl-4-oxo-2H-1,3-benzoxazin-3(4H)-yl)-2,4-dideoxy-L-threo-pentitol To a mixture of 8-chloro-3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4(3H)-one (0.08 g), 5-(chloromethyl)-2-methoxypyridine (0.04 g), 2 M aqueous sodium carbonate solution (0.19 mL) and DME (3 mL) was added tetrakis(triphenylphosphine)palladium (0) (0.01 g) under an argon atmosphere at room temperature, and the mixture was stirred at 90° C. overnight. The reaction mixture was dried over anhydrous sodium sulfate, and the solvent was evaporated under reduced pressure. The residue was purified by NH silica gel column chromatography (ethyl acetate/hexane) and solidified with ethyl acetate to give the title compound (0.03 g).

$^1$H NMR (300 MHz, DMSO-d$_6$) δ 1.38-1.63 (1H, m), 1.82-1.97 (1H, m), 2.33 (3H, s), 3.32-3.39 (1H, m), 3.39-3.51 (1H, m), 3.65-3.75 (1H, m), 3.76-3.80 (1H, m), 3.82 (3H, s), 3.85-3.96 (2H, m), 3.99 (2H, s), 5.09 (1H, d, J=5.1 Hz), 5.29-5.51 (2H, m), 6.76 (1H, d, J=8.5 Hz), 7.43 (1H, dd, J=8.5, 2.5 Hz), 7.51 (1H, s), 8.00 (1H, d, J=2.3 Hz).

Example 110

1,5-anhydro-2,4-dideoxy-2-(7,8-dimethyl-4-oxo-6-((6-vinylpyridin-3-yl)methyl)-2H-1,3-benzoxazin-3(4H)-yl)-L-threo-pentitol To a mixture of 1,5-anhydro-2-(6-((6-chloropyridin-3-yl)methyl)-7,8-dimethyl-4-oxo-2H-1,3-benzoxazin-3(4H)-yl)-2,4-dideoxy-L-threo-pentitol (0.15 g), 2-ethenyl-4,4,5,5-tetramethyl-1,3,2-dioxaborolane (0.09 g), 1,1'-bis(diphenylphosphino)ferrocene palladium (II) chloride (0.01 g) and DME (3 mL) was added 2 M aqueous sodium carbonate solution (0.37 mL) at room temperature, and the mixture was stirred under an argon atmosphere at 80° C. overnight. The reaction mixture was diluted with ethyl acetate, dried over anhydrous magnesium sulfate, and the solvent was evaporated under reduced pressure. The residue was purified by silica gel column chromatography (ethyl acetate/hexane) and solidified with ethyl acetate to give the title compound (0.05 g). In addition, as the second crystal, the title compound (0.02 g) was obtained.

$^1$H NMR (300 MHz, DMSO-d$_6$) δ 1.39-1.60 (1H, m), 1.84-1.97 (1H, m), 2.11 (3H, s), 2.16 (3H, s), 3.32-3.39 (1H, m), 3.40-3.51 (1H, m), 3.69 (1H, dd, J=10.8, 4.3 Hz), 3.76-4.00 (3H, m), 4.02 (2H, s), 5.05 (1H, d, J=5.3 Hz), 5.20-5.37 (2H, m), 5.41 (1H, dd, J=10.8, 1.7 Hz), 6.16 (1H, dd, J=17.4, 1.7 Hz), 6.77 (1H, dd, J=17.6, 10.8 Hz), 7.35-7.52 (3H, m), 8.38 (1H, d, J=1.5 Hz).

Example 111

1,5-anhydro-2,4-dideoxy-2-(7,8-dimethyl-4-oxo-6-((6-((trimethylsilyl)ethynyl)pyridin-3-yl)methyl)-2H-1,3-benzoxazin-3(4H)-yl)-L-threo-pentitol To a mixture of 1,5-anhydro-2-(6-((6-chloropyridin-3-yl)methyl)-7,8-dimethyl-4-oxo-2H-1,3-benzoxazin-3 (4H)-yl)-2,4-dideoxy-L-threo-pentitol (0.15 g), ethynyltrimethylsilane (0.05 g), copper iodide (0.01 g) and 1,1'-bis(diphenylphosphino)ferrocene palladium (II) chloride dichloromethane complex (0.02 g) and THF (3 mL) was added triethylamine (0.38 g) at room temperature, and the mixture was stirred at the same temperature for the weekend. The reaction mixture was concentrated under reduced pressure, and the residue was purified by silica gel column chromatography (ethyl acetate/hexane) to give the title compound (0.09 g).

$^1$H NMR (300 MHz, CDCl$_3$) δ 0.22-0.29 (9H, m), 1.59-1.84 (2H, m), 2.06-2.12 (4H, m), 2.15 (4H, s), 3.48 (1H, td, J=11.7, 2.4 Hz), 3.62-3.75 (1H, m), 3.93-4.05 (5H, m), 5.19-5.29 (2H, m), 7.27-7.38 (2H, m), 7.61 (1H, s), 8.40 (1H, d, J=1.3 Hz).

Example 112

1,5-anhydro-2,4-dideoxy-2-(6-((6-ethynylpyridin-3-yl)methyl)-7,8-dimethyl-4-oxo-2H-1,3-benzoxazin-3(4H)-yl)-L-threo-pentitol To a mixture of 1,5-anhydro-2,4-dideoxy-2-(7,8-dimethyl-4-oxo-6-((6-((trimethylsilyl)ethynyl)pyridin-3-yl)methyl)-2H-1,3-benzoxazin-3(4H)-yl)-L-threo-pentitol (0.08 g), methanol (3.0 mL) and THF (3.0 mL) was added potassium carbonate (0.07 g) at room temperature, and the mixture was stirred at the same temperature overnight. To the reaction mixture was added water, and the mixture was extracted with ethyl acetate. The organic layer was dried over anhydrous magnesium sulfate, and the solvent was evaporated under reduced pressure. The residue was purified by silica gel column chromatography (ethyl acetate/hexane) and solidified with ethyl acetate to give the title compound (0.03 g).

$^1$H NMR (300 MHz, DMSO-d$_6$) δ 1.37-1.61 (1H, m), 1.84-1.97 (1H, m), 2.11 (3H, s), 2.14 (3H, s), 3.31-3.39 (1H, m), 3.45 (1H, s), 3.65-3.74 (1H, m, J=4.3 Hz), 3.76-4.01 (3H, m), 4.06 (2H, s), 4.26 (1H, s), 5.05 (1H, d, J=5.3 Hz), 5.19-5.45 (2H, m), 7.46 (1H, s), 7.47 (2H, d, J=1.3 Hz), 8.37-8.44 (1H, m).

Example 113

1,5-anhydro-2,3-dideoxy-3-(8-fluoro-7-methyl-4-oxo-6-(4-(1H-pyrazol-1-yl)benzyl)-2H-1,3-benzoxazin-3(4H)-yl)-L-threo-pentitol A) 5-(4-(1H-pyrazol-1-yl)benzyl)-3-fluoro-2-hydroxy-N-((3R,4S)-3-hydroxytetrahydro-2H-pyran-4-yl)-4-methylbenzamide To a mixture of 5-(4-(1H-pyrazol-1-yl)benzyl)-3-fluoro-2-hydroxy-4-methylbenzoic acid (0.50 g), (3R,4S)-4-aminotetrahydro-2H-pyran-3-ol hydrochloride (0.25 g), WSC hydrochloride (0.35 g), HOBt monohydrate (0.26 g) and DMF (3 mL) was added triethylamine (0.43 mL), and the mixture was stirred at room temperature overnight. To the reaction mixture was added water, and the mixture was extracted with ethyl acetate-isopropanol (4:1). The organic layer was washed with water and saturated brine, dried over anhydrous magnesium sulfate and concentrated under reduced pressure. The residue was purified by silica gel column chromatography (ethyl acetate/hexane) and solidified with ethyl acetate to give the title compound (0.29 g).
MS: [M+H]$^+$ 426.1

B) 1,5-anhydro-2,3-dideoxy-3-(8-fluoro-7-methyl-4-oxo-6-(4-(1H-pyrazol-1-yl)benzyl)-2H-1,3-benzoxazin-3(4H)-yl)-L-threo-pentitol In a sealed tube, to a mixture of 5-(4-(1H-pyrazol-1-yl)benzyl)-3-fluoro-2-hydroxy-N-((3R,4S)-3-hydroxytetrahydro-2H-pyran-4-yl)-4-methylbenzamide (0.15 g), trioxymethylene (0.10 g) and DME (5 mL) was added p-toluenesulfonic acid monohydrate (0.04 g) at room temperature, and the mixture was stirred at 90° C. overnight. The reaction mixture was neutralized with saturated aqueous sodium hydrogen carbonate solution under ice-cooling, and extracted with ethyl acetate. The organic layer was washed with water and brine, dried over anhydrous sodium sulfate, and the solvent was evaporated under reduced pressure. The residue was purified by silica gel column chromatography (ethyl acetate/hexane) and solidified with ethanol to give the title compound (0.02 g).
$^1$H NMR (300 MHz, DMSO-d$_6$) δ 1.57-1.74 (1H, m), 1.80-2.02 (1H, m), 2.19 (3H, d, J=2.5 Hz), 2.92-3.08 (1H, m), 3.32-3.37 (1H, m), 3.64-3.75 (1H, m), 3.77-3.92 (2H, m), 4.05 (2H, s), 4.08-4.17 (1H, m), 5.12 (1H, d, J=5.5 Hz), 5.28-5.49 (2H, m), 6.52 (1H, dd, J=2.5, 1.9 Hz), 7.21-7.29 (2H, m), 7.42-7.46 (1H, m), 7.71 (1H, d, J=1.3 Hz), 7.73-7.81 (2H, m), 8.43 (1H, d, J=2.5 Hz).

Example 114

1,5-anhydro-2,3-dideoxy-3-(7-methyl-4-oxo-6-(4-(1H-pyrazol-1-yl)benzyl)-2H-1,3-benzoxazin-3(4H)-yl)-L-threo-pentitol A) 5-bromo-2-hydroxy-N-((3R,4S)-3-hydroxytetrahydro-2H-pyran-4-yl)-4-methylbenzamide To a mixture of 5-bromo-2-hydroxy-4-methylbenzoic acid (0.40 g), (3R,4S)-3-aminotetrahydro-2H-pyran-4-ol hydrochloride (0.28 g), WSC hydrochloride (0.40 g), HOBt monohydrate (0.29 g) and DMF (3 mL) was added triethylamine (0.35 g), and the mixture was stirred at room temperature for 4 hr. To the reaction mixture was added water, and the mixture was extracted with ethyl acetate. The organic layer was washed with water and brine, dried over anhydrous sodium sulfate, and concentrated under reduced pressure. The residue was purified by silica gel column chromatography (ethyl acetate/hexane) to give the title compound (0.27 g).
MS: [M+H]$^+$ 329.9, 331.9

B) 6-bromo-3-((3R,4S)-3-hydroxytetrahydro-2H-pyran-4-yl)-7-methyl-2H-benzo[e][1,3]oxazin-4(3H)-one In a sealed tube, to a mixture of 5-bromo-2-hydroxy-N-((3R,4S)-3-hydroxytetrahydro-2H-pyran-4-yl)-4-methylbenzamide (0.27 g), trioxymethylene (0.07 g) and DME (3 mL) was added p-toluenesulfonic acid monohydrate (0.03 g) at room temperature, and the mixture was stirred at 90° C. overnight. The reaction mixture was neutralized with saturated aqueous sodium hydrogen carbonate solution under ice-cooling, and extracted with ethyl acetate. The organic layer was washed with water and brine, dried over anhydrous sodium sulfate, and the solvent was evaporated under reduced pressure. The residue was purified by silica gel column chromatography (ethyl acetate/hexane) to give the title compound (0.20 g).
MS: [M+H]$^+$ 342.0, 344.0

C) 3-((3R,4S)-3-hydroxytetrahydro-2H-pyran-4-yl)-7-methyl-6-(4,4,5,5-tetramethyl-1,3,2-dioxaborolan-2-yl)-2H-benzo[e][1,3]oxazin-4 (3H)-one To a mixture of 6-bromo-3-((3R,4S)-3-hydroxytetrahydro-2H-pyran-4-yl)-7-methyl-2H-benzo[e][1,3]oxazin-4 (3H)-one (0.20 g), bis(pinacolato)diboron (0.22 g), potassium acetate (0.11 g) and toluene (10 mL) was added dichlorobis(triphenylphosphine)palladium (II) (0.02 g) at room temperature, and the mixture was stirred under an argon atmosphere at 90° C. overnight. To the reaction mixture was added water at room temperature, and the mixture was extracted with ethyl acetate. The organic layer was washed with water and brine, dried over anhydrous sodium sulfate, and the solvent was evaporated under reduced pressure. The residue was purified by silica gel column chromatography (ethyl acetate/hexane) to give the title compound (0.22 g).
MS: [M+H]$^+$ 390.1

D) 1,5-anhydro-2,3-dideoxy-3-(7-methyl-4-oxo-6-(4-(1H-pyrazol-1-yl)benzyl)-2H-1,3-benzoxazin-3 (4H)-yl)-L-threo-pentitol To a mixture of 3-((3R,4S)-3-hydroxytetrahydro-2H-pyran-4-yl)-7-methyl-6-(4,4,5,5-tetramethyl-1,3,2-dioxaborolan-2-yl)-2H-benzo[e][1,3]oxazin-4(3H)-one (0.11 g), 1-(4-(chloromethyl)phenyl)-1H-pyrazole (0.06 g), 2 M aqueous sodium carbonate solution (0.27 mL) and DME (3 mL) was added tetrakis(triphenylphosphine)palladium (0) (0.02 g) at room temperature, and the mixture was stirred under an argon atmosphere at 90° C. overnight. The reaction mixture was dried over anhydrous sodium sulfate and the solvent was evaporated under reduced pressure. The residue was purified by silica gel column chromatography (ethyl acetate/hexane) and solidified with ethyl acetate to give the title compound (0.06 g).
$^1$H NMR (300 MHz, DMSO-d$_6$) δ 1.51-1.70 (1H, m), 1.75-2.06 (1H, m), 2.25 (3H, s), 3.00 (1H, t, J=10.4 Hz), 3.32-3.40 (1H, m), 3.66 (1H, tt, J=10.1, 5.0 Hz), 3.78-3.90 (2H, m), 4.01 (2H, s), 4.04-4.23 (1H, m), 5.09 (1H, d, J=5.7 Hz), 5.18-5.42 (2H, m), 6.52 (1H, dd, J=2.5, 1.7 Hz), 6.90 (1H, s), 7.21-7.27 (2H, m), 7.57 (1H, s), 7.70-7.72 (1H, m), 7.73-7.78 (2H, m), 8.43 (1H, d, J=1.9 Hz).

Example 115

1,5-anhydro-2,4-dideoxy-2-(8-fluoro-7-methyl-4-oxo-6-(pyrazolo[1,5-a]pyridin-5-ylmethyl)-2H-1,3-benzoxazin-3(4H)-yl)-L-threo-pentitol To a mixture of 8-fluoro-3-((3S,4S)-4-hydroxytetrahydro-2H-pyran-3-yl)-7-methyl-6-(4,4,5,5-tetramethyl-1,3,2-dioxaborolan-2-yl)-2H-benzo[e][1,3]oxazin-4 (3H)-one (0.11 g), 5-(chloromethyl)pyrazolo[1,5-a]pyridine (0.05 g), 2 M aqueous sodium carbonate solution (0.27 mL) and DME (2.73 mL) was added tetrakis(triphenylphosphine)palladium (0) (0.02 g), and the mixture was stirred under a nitrogen atmosphere at 90° C. overnight. The reaction mixture was dried over anhydrous sodium sulfate, and concentrated under reduced pressure. The residue was purified by silica gel column chromatography (ethyl acetate/hexane) and solidified with ethanol to give the title compound (0.06 g).

$^1$H NMR (300 MHz, DMSO-d$_6$) δ 1.35-1.61 (1H, m), 1.92 (1H, dd, J=14.6, 2.7 Hz), 2.19 (3H, d, J=2.5 Hz), 3.32-3.50 (2H, m), 3.71 (1H, dd, J=10.8, 4.3 Hz), 3.76-3.99 (3H, m), 4.06 (2H, s), 5.09 (1H, d, J=5.3 Hz), 5.40 (2H, q, J=8.9 Hz), 6.50 (1H, dd, J=2.2, 0.8 Hz), 6.66 (1H, dd, J=7.2, 1.9 Hz), 7.32 (1H, s), 7.47 (1H, s), 7.93 (1H, d, J=2.3 Hz), 8.58 (1H, d, J=7.2 Hz).

Example 116

1,5-anhydro-2,4-dideoxy-2-(7,8-dimethyl-6-((2-methyl-2H-indazol-5-yl)methyl)-4-oxo-2H-1,3-benzoxazin-3(4H)-yl)-L-threo-pentitol A) 1,5-anhydro-2,4-dideoxy-2-(7,8-dimethyl-4-oxo-6-(4,4,5,5-tetramethyl-1,3,2-dioxaborolan-2-yl)-2H-1,3-benzoxazin-3(4H)-yl)-L-threo-pentitol To a mixture of 6-bromo-3-((3S,4S)-4-hydroxytetrahydro-2H-pyran-3-yl)-7,8-dimethyl-2H-benzo[e][1,3]oxazin-4(3H)-one (0.56 g), bis(pinacolato)diboron (0.60 g), potassium acetate (0.46 g) and toluene (11 mL) was added trans-dichlorobis(triphenylphosphine)palladium (II) (0.06 g), and the mixture was stirred under an argon atmosphere at 110° C. for 15 hr. The reaction mixture was cooled to room temperature, water was added, and the mixture was diluted with ethyl acetate, washed with water and saturated brine, and dried over anhydrous magnesium sulfate. The solvent was evaporated under reduced pressure, and the residue was purified by silica gel column chromatography (ethyl acetate/hexane) to give the title compound (0.45 g).

MS: [M+H]$^+$ 404.2

B) 1,5-anhydro-2,4-dideoxy-2-(7,8-dimethyl-6-((2-methyl-2H-indazol-5-yl)methyl)-4-oxo-2H-1,3-benzoxazin-3(4H)-yl)-L-threo-pentitol To a mixture of 1,5-anhydro-2,4-dideoxy-2-(7,8-dimethyl-4-oxo-6-(4,4,5,5-tetramethyl-1,3,2-dioxaborolan-2-yl)-2H-1,3-benzoxazin-3(4H)-yl)-L-threo-pentitol (0.10 g), 5-(chloromethyl)-2-methyl-2H-indazole (0.05 g), 2 M aqueous sodium carbonate solution (0.24 mL) and DME (2.36 mL) was added tetrakis(triphenylphosphine)palladium (0) (0.01 g), and the mixture was stirred under a nitrogen atmosphere at 90° C. overnight. The reaction mixture was cooled to room temperature, water was added, and the mixture was diluted with ethyl acetate, washed with water and saturated brine, and dried over anhydrous magnesium sulfate. The solvent was evaporated under reduced pressure, and the residue was purified by silica gel column chromatography (methanol/ethyl acetate) and recrystallized from ethanol to give the title compound (0.03 g).

$^1$H NMR (300 MHz, DMSO-d$_6$) δ 1.41-1.58 (1H, m), 1.85-1.96 (1H, m), 2.11 (3H, s), 2.16 (3H, s), 3.34 (1H, d, J=2.8 Hz), 3.40-3.51 (1H, m), 3.69 (1H, dd, J=11.0, 4.7 Hz), 3.77-3.99 (3H, m), 4.01-4.07 (2H, m), 4.12 (3H, s), 5.02-5.08 (1H, m), 5.22-5.28 (1H, m), 5.30-5.37 (1H, m), 6.99-7.07 (1H, m), 7.27-7.32 (1H, m), 7.42-7.46 (1H, m), 7.47-7.53 (1H, m), 8.17-8.23 (1H, m).

Example 117

1,5-anhydro-2,4-dideoxy-2-(7,8-dimethyl-6-((2-methyl-2H-indazol-6-yl)methyl)-4-oxo-2H-1,3-benzoxazin-3(4H)-yl)-L-threo-pentitol To a mixture of 1,5-anhydro-2,4-dideoxy-2-(7,8-dimethyl-4-oxo-6-(4,4,5,5-tetramethyl-1,3,2-dioxaborolan-2-yl)-2H-1,3-benzoxazin-3(4H)-yl)-L-threo-pentitol (0.08 g), 6-(chloromethyl)-2-methyl-2H-indazole (0.04 g), 2 M aqueous sodium carbonate solution (0.19 mL) and DME (1.93 mL) was added tetrakis(triphenylphosphine)palladium (0) (0.01 g), and the mixture was stirred under a nitrogen atmosphere at 90° C. overnight. The reaction mixture was cooled to room temperature, diluted with ethyl acetate, washed with water and saturated brine, dried over anhydrous magnesium sulfate, and concentrated under reduced pressure. The residue was purified by silica gel column chromatography (methanol/ethyl acetate) and solidified with ethanol to give the title compound (0.02 g).

$^1$H NMR (300 MHz, DMSO-d$_6$) δ 1.40-1.59 (1H, m), 1.83-1.96 (1H, m), 2.12 (3H, s), 2.17 (3H, s), 3.32-3.53 (2H, m), 3.65-3.74 (1H, m), 3.76-3.97 (3H, m), 4.03-4.08 (2H, m), 4.11 (3H, s), 5.05 (1H, d, J=5.3 Hz), 5.22-5.29 (1H, m), 5.30-5.37 (1H, m), 6.82 (1H, dd, J=8.6, 1.4 Hz), 7.21 (1H, s), 7.44 (1H, s), 7.55-7.62 (1H, m), 8.24 (1H, s).

Example 118

1,5-anhydro-2,4-dideoxy-2-(7-ethyl-6-((6-methoxypyridin-3-yl)methyl)-4-oxo-2H-1,3-benzoxazin-3(4H)-yl)-L-threo-pentitol A) 5-bromo-4-ethyl-2-hydroxybenzoic Acid A mixture of methyl 5-bromo-4-ethyl-2-hydroxybenzoate (4.39 g), 4 M aqueous sodium hydroxide solution (33.9 mL), THF (33.9 ml), and methanol (33.9 ml) was stirred at 70° C. for 1 hr. After cooling, the solvent was evaporated under reduced pressure, 6 M hydrochloric acid was added to the residue, and the mixture was extracted with ethyl acetate. The extract was washed with saturated brine, dried over anhydrous sodium sulfate, and the solvent was evaporated under reduced pressure to give the title compound (3.91 g).

$^1$H NMR (300 MHz, DMSO-d$_6$) δ 1.16 (3H, t, J=7.6 Hz), 2.67 (2H, q, J=7.6 Hz), 6.96 (1H, s), 7.87 (1H, s).

B) 5-bromo-4-ethyl-2-hydroxy-N-((3S,4S)-4-hydroxytetrahydro-2H-pyran-3-yl)benzamide To a mixture of 5-bromo-4-ethyl-2-hydroxybenzoic acid (3.91 g), (3S,4S)-3-aminotetrahydro-2H-pyran-4-ol (1.96 g), HOBt monohydrate (2.93 g), triethylamine (3.34 ml), and DMF (53.2 ml) was added WSC hydrochloride (3.67 g), and the mixture was stirred at room temperature for 15 hr. Water was added, and the mixture was extracted with ethyl acetate. The extract was washed with water and saturated brine, dried over anhydrous sodium sulfate, and the solvent was evaporated under reduced pressure. The residue was purified by silica gel column chromatography (ethyl acetate/hexane) to give the title compound (2.07 g).

$^1$H NMR (300 MHz, DMSO-d$_6$) δ 1.15 (3H, t, J=7.5 Hz), 1.40-1.58 (1H, m), 1.63-1.96 (1H, m), 2.64 (2H, q, J=7.5 Hz), 3.04-3.18 (1H, m), 3.32-3.36 (1H, m), 3.58-3.87 (4H, m), 5.04 (1H, d, J=5.1 Hz), 6.89 (1H, s), 8.14 (1H, s), 8.59 (1H, d, J=7.6 Hz), 12.52 (1H, s).

C) 6-bromo-7-ethyl-3-((3S,4S)-4-hydroxytetrahydro-2H-pyran-3-yl)-2H-benzo[e][1,3]oxazin-4(3H)-one A mixture of 5-bromo-4-ethyl-2-hydroxy-N-((3S,4S)-4-hydroxytetrahydro-2H-pyran-3-yl)benzamide (2.07 g), 1,3,5-trioxane (1.63 g), p-toluenesulfonic acid monohydrate (0.69 g) and DME (30.1 mL) was added into a sealed tube at room temperature, and stirred at 90° C. for 15 hr. After cooling to room temperature, the reaction mixture was poured into saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane) to give the title compound (1.46 g).

$^1$H NMR (300 MHz, DMSO-$d_6$) δ 1.17 (3H, t, J=7.5 Hz), 1.39-1.60 (1H, m), 1.83-2.01 (1H, m), 2.71 (2H, d, J=7.6 Hz), 3.34-3.52 (2H, m), 3.70 (1H, dd, J=11.2, 4.4 Hz), 3.75-4.04 (3H, m), 5.08 (1H, d, J=5.5 Hz), 5.30 (1H, d, J=8.7 Hz), 5.37 (1H, d, J=8.7 Hz), 7.09 (1H, s), 7.87 (1H, s).

D) 7-ethyl-3-((3S,4S)-4-hydroxytetrahydro-2H-pyran-3-yl)-6-(4,4,5,5-tetramethyl-1,3,2-dioxaborolan-2-yl)-2H-benzo[e][1,3]oxazin-4(3H)-one A mixture of 6-bromo-7-ethyl-3-((3S,4S)-4-hydroxytetrahydro-2H-pyran-3-yl)-2H-benzo[e][1,3]oxazin-4(3H)-one (0.35 g), bis(pinacolato)diboron (0.37 g), dichlorobis(triphenylphosphine)palladium (II) (0.03 g), potassium acetate (0.19 g), and toluene (9.8 mL) was heated under a nitrogen atmosphere at 90° C. for 15 hr. The reaction mixture was cooled, diluted with water, and extracted with ethyl acetate. The extract was washed with saturated brine, dried over anhydrous magnesium sulfate, and concentrated under reduced pressure. The residue was purified by silica gel column chromatography (ethyl acetate/hexane) to give the title compound (0.33 g).

MS: [M+H]$^+$ 404.2

E) 1,5-anhydro-2,4-dideoxy-2-(7-ethyl-6-((6-methoxypyridin-3-yl)methyl)-4-oxo-2H-1,3-benzoxazin-3(4H)-yl)-L-threo-pentitol A mixture of 7-ethyl-3-((3S,4S)-4-hydroxytetrahydro-2H-pyran-3-yl)-6-(4,4,5,5-tetramethyl-1,3,2-dioxaborolan-2-yl)-2H-benzo[e][1,3]oxazin-4(3H)-one (0.33 g), 5-(chloromethyl)-2-methoxypyridine (0.19 g), tetrakis(triphenylphosphine)palladium (0) (0.05 g), sodium carbonate (2 M aqueous solution, 0.82 mL), and DME (8.2 mL) was heated under a nitrogen atmosphere at 90° C. for 15 hr. The reaction mixture was cooled, diluted with water, and extracted with ethyl acetate. The extract was washed with saturated brine, dried over anhydrous magnesium sulfate, and concentrated under reduced pressure. The residue was purified by silica gel column chromatography (ethyl acetate/hexane) and NH silica gel column chromatography (ethyl acetate/hexane) to give the title compound (0.16 g).

$^1$H NMR (300 MHz, DMSO-$d_6$) δ 1.09 (3H, t, J=7.5 Hz), 1.36-1.61 (1H, m), 1.82-1.97 (1H, m), 2.62 (2H, d, J=7.6 Hz), 3.30-3.51 (2H, m), 3.68 (1H, dd, J=11.0, 4.6 Hz), 3.75-4.03 (8H, m), 5.04 (1H, d, J=5.1 Hz), 5.28 (1H, d, J=8.7 Hz), 5.32 (1H, d, J=8.7 Hz), 6.75 (1H, d, J=8.5 Hz), 6.88 (1H, s), 7.42 (1H, dd, J=2.4, 8.5 Hz), 7.48 (1H, s), 7.99 (1H, d, J=2.4 Hz).

Example 119

1,5-anhydro-2-(6-(((6-chloropyridin-3-yl)methyl)-7-ethyl-4-oxo-2H-1,3-benzoxazin-3(4H)-yl)-2,4-dideoxy-L-threo-pentitol To a mixture of 6-bromo-7-ethyl-3-((3S,4S)-4-hydroxytetrahydro-2H-pyran-3-yl)-2H-benzo[e][1,3]oxazin-4(3H)-one (0.35 g), bis(tri-tert-butylphosphine)palladium (0) (0.03 g) and THF (6.55 mL) was added at room temperature (6-chloro-3-pyridyl)methylzinc chloride 0.5 M THF solution (2.75 mL), and the mixture was stirred under a nitrogen atmosphere at 80° C. for hr. After cooling to room temperature, water was added to the reaction mixture, and the mixture was filtered through celite, and the filtrate was extracted with ethyl acetate. The extract was washed with saturated brine, and dried over anhydrous magnesium sulfate. The solvent was evaporated under reduced pressure. The residue was purified by silica gel column chromatography (ethyl acetate/hexane) to give the title compound (0.24 g).

$^1$H NMR (300 MHz, DMSO-$d_6$) δ 1.07 (3H, t, J=7.6 Hz), 1.40-1.58 (1H, m), 1.83-1.96 (1H, m), 2.59 (2H, q, J=7.6 Hz), 3.32-3.50 (2H, m), 3.68 (1H, dd, J=11.0, 4.3 Hz), 3.76-4.08 (5H, m), 5.05 (1H, d, J=5.3 Hz), 5.26 (1H, d, J=8.7 Hz), 5.33 (1H, d, J=8.7 Hz), 6.90 (1H, s), 7.44 (1H, d, J=8.1 Hz), 7.50-7.60 (2H, m), 8.27 (1H, d, J=2.1 Hz).

Example 120

7-ethyl-3-((3S,4S)-4-hydroxytetrahydro-2H-pyran-3-yl)-6-((6-vinylpyridin-3-yl)methyl)-2H-benzo[e][1,3]oxazin-4(3H)-one To a mixture of 1,5-anhydro-2-(6-(((6-chloropyridin-3-yl)methyl)-7-ethyl-4-oxo-2H-1,3-benzoxazin-3(4H)-yl)-2,4-dideoxy-L-threo-pentitol (0.23 g), 2-ethenyl-4,4,5,5-tetramethyl-1,3,2-dioxaborolane (0.13 g), 1,1'-bis(diphenylphosphino)ferrocene palladium (II) chloride (0.02 g) and DME (5.71 mL) was added 2 M aqueous sodium carbonate solution (0.57 mL) at room temperature, and the mixture was stirred under a nitrogen atmosphere at 80° C. for 15 hr. The reaction mixture was diluted with ethyl acetate, dried over anhydrous magnesium sulfate, and the solvent was evaporated under reduced pressure. The reaction mixture was cooled to room temperature, diluted with water, and extracted with ethyl acetate. The extract was washed with saturated brine, and dried over anhydrous magnesium sulfate. The solvent was evaporated under reduced pressure. The residue was purified by silica gel column chromatography (ethyl acetate/hexane) and recrystallized from ethyl acetate-hexane to give the title compound (0.12 g).

$^1$H NMR (300 MHz, DMSO-$d_6$) δ 1.08 (3H, t, J=7.5 Hz), 1.38-1.59 (1H, m), 1.78-1.96 (1H, m), 2.61 (2H, q, J=7.5 Hz), 3.26-3.50 (2H, m), 3.61-4.10 (6H, m), 5.05 (1H, d, J=5.3 Hz), 5.26 (1H, d, J=9.0 Hz), 5.33 (1H, d, J=9.0 Hz), 5.42 (1H, dd, 1.6, 10.9 Hz), 6.17 (1H, dd, J=17.5, 1.6 Hz), 6.78 (1H, dd, J=17.5, 10.9 Hz), 6.90 (1H, s), 7.40-7.55 (3H, m), 8.39 (1H, d, J=1.5 Hz).

Example 121

1,5-anhydro-2,4-dideoxy-2-(7-ethenyl-4-oxo-6-(4-(1H-pyrazol-1-yl)benzyl)-2H-1,3-benzoxazin-3(4H)-yl)-L-threo-pentitol

A) 5-bromo-2-hydroxy-4-vinylbenzoic Acid

To a mixture of 4-ethenyl-2-hydroxybenzoic acid (1.0 g) and acetic acid (5 mL) was added at room temperature bromine (0.97 g), and the mixture was stirred overnight. To the reaction mixture was added saturated aqueous sodium thiosulfate solution, and the mixture was extracted with ethyl acetate. The organic layer was washed with water and brine, and dried over anhydrous magnesium sulfate. The solvent was evaporated under reduced pressure. The residue was washed with hexane-diisopropyl ether to give the title compound (0.69 g).
MS: [M+H]$^+$ 240.8, 242.8

B) 5-bromo-2-hydroxy-N-((3S,4S)-4-hydroxytetrahydro-2H-pyran-3-yl)-4-vinylbenzamide To a mixture of 5-bromo-2-hydroxy-4-vinylbenzoic acid (0.69 g), (3S,4S)-3-aminotetrahydro-2H-pyran-4-ol (0.37 g), WSC hydrochloride (0.65 g), HOBt monohydrate (0.48 g) and DMF (8 mL) was added triethylamine (0.58 g), and the mixture was stirred at room temperature overnight. To the reaction mixture was added water, and the mixture was extracted with ethyl acetate. The organic layer was washed with water and brine, dried over anhydrous magnesium sulfate and concentrated under reduced pressure. The residue was purified by silica gel column chromatography (ethyl acetate/hexane) to give the title compound (0.12 g).
MS: [M+H]+ 341.9, 343.9

C) 6-bromo-3-((3S,4S)-4-hydroxytetrahydro-2H-pyran-3-yl)-7-vinyl-2H-benzo[e][1,3]oxazin-4(3H)-one In a sealed tube, to a mixture of 5-bromo-2-hydroxy-N-((3S,4S)-4-hydroxytetrahydro-2H-pyran-3-yl)-4-vinylbenzamide (0.11 g), trioxymethylene (0.09 g) and DME (3 mL) was added p-toluenesulfonic acid monohydrate (0.04 g) at room temperature, and the mixture was stirred at 90° C. overnight. The reaction mixture was neutralized with saturated aqueous sodium hydrogen carbonate solution under ice-cooling, and extracted with ethyl acetate. The organic layer was washed with water and brine, dried over anhydrous sodium sulfate, and the solvent was evaporated under reduced pressure. The residue was purified by silica gel column chromatography (ethyl acetate/hexane) to give the title compound (0.06 g).
MS: [M+H]$^+$ 354.1, 356.2

D) 3-((3S,4S)-4-hydroxytetrahydro-2H-pyran-3-yl)-6-(4,4,5,5-tetramethyl-1,3,2-dioxaborolan-2-yl)-7-vinyl-2H-benzo[e][1,3]oxazin-4(3H)-one In the same manner as in Example 103, C), the title compound was synthesized.
MS: [M+H]$^+$ 402.1

E) 1,5-anhydro-2,4-dideoxy-2-(7-ethenyl-4-oxo-6-(4-(1H-pyrazol-1-yl)benzyl)-2H-1,3-benzoxazin-3(4H)-yl)-L-threo-pentitol In the same manner as in Example 103, D), the title compound was synthesized.
$^1$H NMR (300 MHz, DMSO-d$_6$) δ 1.34-1.60 (1H, m), 1.83-1.96 (1H, m), 3.33 (1H, brs), 3.43 (1H, t, J=10.7 Hz), 3.62-3.73 (1H, m), 3.76-4.00 (5H, m), 5.05 (1H, d, J=5.1 Hz), 5.20-5.40 (3H, m), 5.66 (1H, s), 6.50 (1H, dd, J=2.5, 1.9 Hz), 7.14 (1H, d, J=1.5 Hz), 7.26-7.38 (3H, m), 7.67-7.75 (4H, m), 8.41 (1H, d, J=2.5 Hz).

The compounds of Examples 1-29, 50, 89-121 in Table 1 were produced by the methods shown in the above-mentioned Examples, and the compounds of Examples 30-49, 51-82, 84-88 and 122-142 in Table 1 were produced by the methods shown in the above-mentioned production methods and Examples or a method analogous thereto. Example compounds are shown in Table 1. In the Tables, MS means measured values.

TABLE 1

| Ex. No. | IUPAC name | structural formula | salt | MS |
|---|---|---|---|---|
| 1 | 8-fluoro-3-((3S,4S)-4-hydroxytetrahydro-2H-pyran-3-yl)-7-methyl-6-(4-(1H-pyrazol-1-yl)benzyl)-2,3-dihydro-4H-1,3-benzoxazin-4-one<br>Alias; 1,5-anhydro-2,4-dideoxy-2-(8-fluoro-7-methyl-4-oxo-6-(4-(1H-pyrazol-1-yl)benzyl)-2H-1,3-benzoxazin-3(4H)-yl)-L-threo-pentitol | | | 438.1 |

TABLE 1-continued

| Ex. No. | IUPAC name | structural formula | salt | MS |
|---|---|---|---|---|
| 2 | 8-chloro-3-((1S,2S)-2-hydroxycyclohexyl)-7-methyl-6-((6-methylpyridin-3-yl)methyl)-2,3-dihydro-4H-1,3-benzoxazin-4-one | | | 401.1 |
| 3 | 1,5-anhydro-2,4-dideoxy-2-(6-((6-methylpyridin-3-yl)methyl)-4-oxo-2H-naphtho[2,1-e][1,3]oxazin-3(4H)-yl)-threo-pentitol (optical isomer) | | HCl | 405.1 |
| 4 | 1,5-anhydro-2-(6-((6-chloropyridin-3-yl)methyl)-4-oxo-2H-naphtho[2,1-e][1,3]oxazin-3(4H)-yl)-2,4-dideoxy-L-threo-pentitol | | | 425.1 |
| 5 | 8-fluoro-3-((1S,2S)-2-hydroxycyclopentyl)-7-methyl-6-(4-(1H-pyrazol-1-yl)benzyl)-2,3-dihydro-4H-1,3-benzoxazin-4-one | | | 422.2 |

TABLE 1-continued

| Ex. No. | IUPAC name | structural formula | salt | MS |
|---|---|---|---|---|
| 6 | 1,5-anhydro-2-(8-chloro-7-methyl-6-((6-methylpyridin-3-yl)methyl)-4-oxo-2H-1,3-benzoxazin-3(4H)-yl)-2,4-dideoxy-L-threo-pentitol | | | 403.1 |
| 7 | 1,5-anhydro-2,4-dideoxy-2-(7,8-dimethyl-6-((6-methylpyridin-3-yl)methyl)-4-oxo-2H-1,3-benzoxazin-3(4H)-yl)-threo-pentitol (optical isomer) | | HCl | 383.2 |
| 8 | 6-((6-chloropyridin-3-yl)methyl)-3-((1S,2S)-2-hydroxycyclopentyl)-7,8-dimethyl-2,3-dihydro-4H-1,3-benzoxazin-4-one | | | 387.1 |
| 9 | 8-fluoro-3-((1S,2S)-2-hydroxycyclopentyl)-7-methyl-6-(4-(1-methyl-1H-pyrazol-3-yl)benzyl)-2,3-dihydro-4H-1,3-benzoxazin-4-one | | | 436.2 |

TABLE 1-continued

| Ex. No. | IUPAC name | structural formula | salt | MS |
|---|---|---|---|---|
| 10 | 1,5-anhydro-2-(6-((6-chloropyridin-3-yl)methyl)-7,8-dimethyl-4-oxo-2H-1,3-benzoxazin-3(4H)-yl)-2,4-dideoxy-L-threo-pentitol | | | 403.1 |
| 11 | 3-((1S,2S)-2-hydroxycyclopentyl)-7,8-dimethyl-6-((6-methylpyridin-3-yl)methyl)-2,3-dihydro-4H-1,3-benzoxazin-4-one | | | 367.2 |
| 12 | 4-((8-fluoro-3-((1S,2S)-2-hydroxycyclopentyl)-7-methyl-4-oxo-3,4-dihydro-2H-1,3-benzoxazin-6-yl)methyl)benzonitrile | | | 381.1 |
| 13 | 8-fluoro-3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one | | | 423.0 |

TABLE 1-continued

| Ex. No. | IUPAC name | structural formula | salt | MS |
|---|---|---|---|---|
| 14 | 3-((1S,2S)-2-hydroxycyclopentyl)-7-methyl-6-((6-(1H-pyrazol-1-yl)pyridin-3-yl)methyl)-2,3-dihydro-4H-1,3-benzoxazin-4-one | | | 405.0 |
| 15 | 8-fluoro-3-(trans-2-hydroxycyclopentyl)-7-methoxy-6-((6-(1H-pyrazol-1-yl)pyridin-3-yl)methyl)-2,3-dihydro-4H-1,3-benzoxazin-4-one | | | 439.1 |
| 16 | 6-((6-chloropyridin-3-yl)methyl)-8-fluoro-3-((1S,2S)-2-hydroxycyclopentyl)-7-methyl-2,3-dihydro-4H-1,3-benzoxazin-4-one | | | 391.1 |
| 17 | 1,5-anhydro-2,4-dideoxy-2-(6-(4-methoxybenzyl)-7,8-dimethyl-4-oxo-2H-1,3-benzoxazin-3(4H)-yl)-threo-pentitol (optical isomer) | | | 398.2 |

TABLE 1-continued

| Ex. No. | IUPAC name | structural formula | salt | MS |
|---|---|---|---|---|
| 18 | 8-fluoro-3-((1S,2S)-2-hydroxycyclopentyl)-6-((6-methoxypyridin-3-yl)methyl)-7-methyl-2,3-dihydro-4H-1,3-benzoxazin-4-one | | | 387.1 |
| 19 | 1,5-anhydro-2-(6-((6-chloropyridin-3-yl)methyl)-8-fluoro-7-methyl-4-oxo-2H-1,3-benzoxazin-3(4H)-yl)-2,4-dideoxy-L-threo-pentitol | | | 407.0 |
| 20 | 8-fluoro-3-((1S,2S)-2-hydroxycyclopentyl)-7-methyl-6-((6-methylpyridin-3-yl)methyl)-2,3-dihydro-4H-1,3-benzoxazin-4-one | | | 371.2 |
| 21 | 6-((4,4-difluoropiperidin-1-yl)methyl)-3-((1S,2S)-2-hydroxycyclopentyl)-2,3-dihydro-4H-naphtho[2,1-e][1,3]oxazin-4-one | | | 417.1 |

TABLE 1-continued

| Ex. No. | IUPAC name | structural formula | salt | MS |
|---|---|---|---|---|
| 22 | 8-fluoro-3-((1S,2S)-2-hydroxycyclopentyl)-7-methyl-6-((6-(1-methyl-1H-pyrazol-3-yl)pyridin-3-yl)methyl)-2,3-dihydro-4H-1,3-benzoxazin-4-one | | | 437.1 |
| 23 | 3-[(3S,4S)-4-hydroxytetrahydro-2H-pyran-3-yl]-7,8-dimethyl-6-[4-(1H-pyrazol-1-yl)benzyl]-2,3-dihydro-4H-1,3-benzoxazin-4-one Alias; 1,5-anhydro-2,4-dideoxy-2-(7,8-dimethyl-4-oxo-6-(4-(1H-pyrazol-1-yl)benzyl)-2H-1,3-benzoxazin-3(4H)-yl)-L-threo-pentitol | | | 434.1 |
| 24 | 8-chloro-6-((6-chloropyridin-3-yl)methyl)-3-((1S,2S)-2-hydroxycyclopentyl)-7-methyl-2,3-dihydro-4H-1,3-benzoxazin-4-one | | | 407.0 |
| 25 | 8-chloro-3-((1S,2S)-2-hydroxycyclopentyl)-7-methyl-6-((6-methylpyridin-3-yl)methyl)-2,3-dihydro-4H-1,3-benzoxazin-4-one | | | 387.1 |

TABLE 1-continued

| Ex. No. | IUPAC name | structural formula | salt | MS |
|---|---|---|---|---|
| 26 | 3-((1S,2S)-2-hydroxycyclopentyl)-7,8-dimethyl-6-((6-methylpyridin-3-yl)methyl)-2,3-dihydro-4H-1,3-benzoxazin-4-one | | HCl | 367.1 |
| 27 | 8-fluoro-3-((1S,2S)-2-hydroxycyclohexyl)-7-methyl-6-((6-methylpyridin-3-yl)methyl)-2,3-dihydro-4H-1,3-benzoxazin-4-one | | | 385.1 |
| 28 | 3-(trans-2-hydroxycyclohexyl)-7-methyl-6-((6-methylpyridin-3-yl)methyl)-2,3-dihydro-4H-1,3-benzoxazin-4-one (optical isomer) | | HCl | 367.2 |
| 29 | 3-((3S,4S)-4-hydroxytetrahydro-2H-pyran-3-yl)-6-((6-methoxypyridin-3-yl)methyl)-7,8-dimethyl-2,3-dihydro-4H-1,3-benzoxazin-4-one Alias; 1,5-anhydro-2,4-dideoxy-2-(6-((6-methoxypyridin-3-yl)methyl)-7,8-dimethyl-4-oxo-2H-1,3-benzoxazin-3(4H)-yl)-L-threo-pentitol | | | 399.2 |

TABLE 1-continued

| Ex. No. | IUPAC name | structural formula | salt | MS |
|---|---|---|---|---|
| 30 | 8-fluoro-3-(trans-2-hydroxycyclopentyl)-7-methyl-6-(4-(1H-pyrazol-1-yl)benzyl)-2,3-dihydro-4H-1,3-benzoxazin-4-one | | | 422.1 |
| 31 | 1,5-anhydro-2-(6-((6-chloropyridin-3-yl)methyl)-7,8-dimethyl-4-oxo-2H-1,3-benzoxazin-3(4H)-yl)-2,4-dideoxy-threo-pentitol | | | 403.1 |
| 32 | 1,5-anhydro-2,4-dideoxy-2-(8-fluoro-7-methyl-6-((6-methylpyridin-3-yl)methyl)-4-oxo-2H-1,3-benzoxazin-3(4H)-yl)-L-threo-pentitol | | | 387.2 |
| 33 | 3-(trans-2-hydroxycyclohexyl)-7-methyl-6-((6-methylpyridin-3-yl)methyl)-2,3-dihydro-4H-1,3-benzoxazin-4-one | | | 367.2 |

TABLE 1-continued

| Ex. No. | IUPAC name | structural formula | salt | MS |
|---|---|---|---|---|
| 34 | 6-((6-chloropyridin-3-yl)methyl)-3-((1S,2S)-2-hydroxycyclopentyl)-7-methyl-2,3-dihydro-4H-1,3-benzoxazin-4-one | | | 373.0 |
| 35 | 3-((1S,2S)-2-hydroxycyclopentyl)-7-methyl-6-(4-(1H-pyrazol-1-yl)benzyl)-2,3-dihydro-4H-1,3-benzoxazin-4-one | | | 404.1 |
| 36 | 3-(trans-2-hydroxycyclohexyl)-7-methyl-6-((6-(1H-pyrazol-1-yl)pyridin-3-yl)methyl)-2,3-dihydro-4H-1,3-benzoxazin-4-one | | | 419.2 |
| 37 | 1,5-anhydro-2,4-dideoxy-2-(7,8-dimethyl-6-((6-(1-methyl-1H-pyrazol-3-yl)pyridin-3-yl)methyl-4-oxo-2H-1,3-benzoxazin-3(4H)-yl)-L-threo-pentitol | | | 449.1 |

TABLE 1-continued

| Ex. No. | IUPAC name | structural formula | salt | MS |
|---|---|---|---|---|
| 38 | 1,5-anhydro-2,4-dideoxy-2-(6-((6-ethylpyridin-3-yl)methyl)-4-oxo-2H-naphtho[2,1-e][1,3]oxazin-3(4H)-yl)-L-threo-pentitol | | HCl | 419.1 |
| 39 | 8-chloro-3-(trans-2-hydroxycyclopentyl)-6-((6-(1H-imidazol-1-yl)pyridin-3-yl)methyl)-7-methyl-2,3-dihydro-4H-1,3-benzoxazin-4-one | | | 439.1 |
| 40 | 3-((1S,2S)-2-hydroxycyclopentyl)-6-((6-methylpyridin-3-yl)methyl)-2,3-dihydro-4H-naphtho[2,1-e][1,3]oxazin-4-one | | HCl | 389.1 |
| 41 | 3-(trans-2-hydroxycyclohexyl)-6-((6-(1-methyl-1H-pyrazol-4-yl)pyridin-3-yl)methyl)-2,3-dihydro-4H-naphtho[2,1-e][1,3]oxazin-4-one | | | 469.2 |

TABLE 1-continued

| Ex. No. | IUPAC name | structural formula | salt | MS |
|---|---|---|---|---|
| 42 | 1,5-anhydro-2,4-dideoxy-2-(4-oxo-6-((6-vinylpyridin-3-yl)methyl)-2H-naphtho[2,1-e][1,3]oxazin-3(4H)-yl)-L-threo-pentitol | | | 417.1 |
| 43 | 6-((6-chloropyridin-3-yl)methyl)-3-((1S,2S)-2-hydroxycyclopentyl)-2,3-dihydro-4H-naphtho[2,1-e][1,3]oxazin-4-one | | | 408.9 |
| 44 | 4-((3-((1S,2S)-2-hydroxycyclopentyl)-7,8-dimethyl-4-oxo-3,4-dihydro-2H-1,3-benzoxazin-6-yl)methyl)benzonitrile | | | 377.2 |
| 45 | 8-chloro-7-methyl-6-((6-(1-methyl-1H-pyrazol-4-yl)pyridin-3-yl)methyl)-3-(tetrahydrofuran-2-ylmethyl)-2,3-dihydro-4H-1,3-benzoxazin-4-one | | HCl | 453.1 |

TABLE 1-continued

| Ex. No. | IUPAC name | structural formula | salt | MS |
|---|---|---|---|---|
| 46 | 1,5-anhydro-2,4-dideoxy-2-(6-((6-methoxypyridin-3-yl)methyl)-4-oxo-2H-naphtho[2,1-e][1,3]oxazin-3(4H)-yl)-L-threo-pentitol | | | 421.1 |
| 47 | 6-((6-(1-methyl-1H-pyrazol-4-yl)pyridin-3-yl)methyl)-2,3-dihydro-4H-naphtho[2,1-e][1,3]oxazin-4-one | | | 371.1 |
| 48 | 8-fluoro-3-(trans-2-hydroxycyclopentyl)-6-((6-(1H-imidazol-1-yl)pyridin-3-yl)methyl)-7-methoxy-2,3-dihydro-4H-1,3-benzoxazin-4-one | | | 439.1 |
| 49 | 3-(trans-2-hydroxycyclohexyl)-7,8-dimethyl-6-((6-(1-methyl-1H-pyrazol-4-yl)pyridin-3-yl)methyl)-2,3-dihydro-4H-1,3-benzoxazin-4-one | | | 447.2 |

TABLE 1-continued

| Ex. No. | IUPAC name | structural formula | salt | MS |
|---|---|---|---|---|
| 50 | 1,5-anhydro-2,4-dideoxy-2-(7-methyl-4-oxo-6-(4-(1H-pyrazol-1-yl)benzyl)-2H-1,3-benzoxazin-3(4H)-yl)-L-threo-pentitol | | | 420.1 |
| 51 | 8-chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one | | | 439.1 |
| 52 | 3-(trans-2-hydroxycyclohexyl)-7-methyl-6-(4-(1H-pyrazol-1-yl)benzyl)-2,3-dihydro-4H-1,3-benzoxazin-4-one | | | 418.2 |

TABLE 1-continued

| Ex. No. | IUPAC name | structural formula | salt | MS |
|---|---|---|---|---|
| 53 | 3-(trans-2-hydroxycyclohexyl)-7,8-dimethyl-6-(4-(1H-pyrazol-1-yl)benzyl)-2,3-dihydro-4H-1,3-benzoxazin-4-one | | | 432.2 |
| 54 | 6-((6-chloropyridin-3-yl)methyl)-8-fluoro-3-((1S,2S)-2-hydroxycyclohexyl)-7-methyl-2,3-dihydro-4H-1,3-benzoxazin-4-one | | | 405.1 |
| 55 | 8-fluoro-3-(trans-2-hydroxycyclopentyl)-7-methoxy-6-((6-(1H-pyrazol-1-yl)pyridin-3-yl)methyl)-2,3-dihydro-4H-1,3-benzoxazin-4-one (optical isomer) | | | 439.1 |
| 56 | 6-((6-chloropyridin-3-yl)methyl)-3-(trans-2-hydroxycyclohexyl)-2,3-dihydro-4H-naphtho[2,1-e][1,3]oxazin-4-one | | | 423.1 |

TABLE 1-continued

| Ex. No. | IUPAC name | structural formula | salt | MS |
|---|---|---|---|---|
| 57 | 3-((1S,2S)-2-hydroxycyclopentyl)-6-(thiomorpholin-4-ylmethyl)-2,3-dihydro-4H-naphtho[2,1-e][1,3]oxazin-4-one | | | 399.1 |
| 58 | 6-((6-methylpyridin-3-yl)methyl)-3-(tetrahydrofuran-2-ylmethyl)-2,3-dihydro-4H-naphtho[2,1-e][1,3]oxazin-4-one | | | 389.1 |
| 59 | 1,5-anhydro-2,4-dideoxy-2-(6-(4-methoxybenzyl)-7,8-dimethyl-4-oxo-2H-1,3-benzoxazin-3(4H)-yl)-threo-pentitol | | | 398.2 |
| 60 | 3-((1S,2S)-2-hydroxycyclopentyl)-6-((1-oxidothiomorpholin-4-yl)methyl)-2,3-dihydro-4H-naphtho[2,1-e][1,3]oxazin-4-one | | | 415.1 |

TABLE 1-continued

| Ex. No. | IUPAC name | structural formula | salt | MS |
|---|---|---|---|---|
| 61 | 7-methyl-6-(4-(1-methyl-1H-1,2,3-triazol-4-yl)benzyl)-3-(tetrahydrofuran-2-ylmethyl)-2,3-dihydro-4H-1,3-benzoxazin-4-one | | | 419.2 |
| 62 | 6-((6-chloropyridin-3-yl)methyl)-3-(trans-2-hydroxycyclohexyl)-7-methyl-2,3-dihydro-4H-1,3-benzoxazin-4-one | | | 387.1 |
| 63 | 3-(trans-2-hydroxycyclohexyl)-6-((6-(1-methyl-1H-pyrazol-4-yl)pyridin-3-yl)methyl)-2,3-dihydro-4H-1,3-benzoxazin-4-one | | | 419.2 |
| 64 | 3-((1S,2S)-2-hydroxycyclopentyl)-7-methyl-6-((6-methylpyridin-3-yl)methyl)-2,3-dihydro-4H-1,3-benzoxazin-4-one | | HCl | 353.1 |

TABLE 1-continued

| Ex. No. | IUPAC name | structural formula | salt | MS |
|---|---|---|---|---|
| 65 | 3-(trans-2-hydroxycyclohexyl)-8-methyl-6-(4-(1H-pyrazol-1-yl)benzyl)-2,3-dihydro-4H-1,3-benzoxazin-4-one | | | 418.2 |
| 66 | 3-(trans-2-hydroxycyclohexyl)-6-(4-(1-methyl-1H-pyrazol-4-yl)benzyl)-2,3-dihydro-4H-1,3-benzoxazin-4-one | | | 418.1 |
| 67 | 4-((3-((1S,2S)-2-hydroxycyclopentyl)-7-methyl-4-oxo-3,4-dihydro-2H-1,3-benzoxazin-6-yl)methyl)benzonitrile | | | 363.2 |
| 68 | 6-((6-methylpyridin-3-yl)methyl)-3-(tetrahydrofuran-2-ylmethyl)-2,3-dihydro-4H-naphtho[2,1-e][1,3]oxazin-4-one | | HCl | 389.2 |

TABLE 1-continued

| Ex. No. | IUPAC name | structural formula | salt | MS |
|---|---|---|---|---|
| 69 | 6-((3,3-difluoropyrrolidin-1-yl)methyl)-3-((1S,2S)-2-hydroxycyclopentyl)-2,3-dihydro-4H-naphtho[2,1-e][1,3]oxazin-4-one | | | 403.2 |
| 70 | 1-((3-((1S,2S)-2-hydroxycyclopentyl)-4-oxo-3,4-dihydro-2H-naphtho[2,1-e][1,3]oxazin-6-yl)methyl)piperidine-4-carbonitrile | | | 406.2 |
| 71 | 7-methyl-6-((6-(1-methyl-1H-1,2,3-triazol-4-yl)pyridin-3-yl)methyl)-3-(tetrahydrofuran-2-ylmethyl)-2,3-dihydro-4H-1,3-benzoxazin-4-one | | | 420.2 |
| 72 | 6-((3,3-difluoropiperidin-1-yl)methyl)-3-((1S,2S)-2-hydroxycyclopentyl)-2,3-dihydro-4H-naphtho[2,1-e][1,3]oxazin-4-one | | | 417.1 |

TABLE 1-continued

| Ex. No. | IUPAC name | structural formula | salt | MS |
|---|---|---|---|---|
| 73 | 3-((1S,2S)-2-hydroxycyclopentyl)-6-(4-methoxybenzyl)-7-methyl-2,3-dihydro-4H-1,3-benzoxazin-4-one | | | 368.1 |
| 74 | 8-fluoro-7-methoxy-6-((6-(1-methyl-1H-pyrazol-4-yl)pyridin-3-yl)methyl)-3-(tetrahydrofuran-2-ylmethyl)-2,3-dihydro-4H-1,3-benzoxazin-4-one | | HCl | 453.1 |
| 75 | 1-((3-((1S,2S)-2-hydroxycyclopentyl)-4-oxo-3,4-dihydro-2H-naphtho[2,1-e][1,3]oxazin-6-yl)methyl)pyrrolidine-3-carbonitrile (diastereoisomer) | | | 392.2 |
| 76 | 6-((6-chloropyridin-3-yl)methyl)-3-(tetrahydrofuran-2-ylmethyl)-2,3-dihydro-4H-naphtho[2,1-e][1,3]oxazin-4-one | | | 408.9 |

TABLE 1-continued

| Ex. No. | IUPAC name | structural formula | salt | MS |
|---|---|---|---|---|
| 77 | 3-((1S,2S)-2-hydroxycyclopentyl)-6-(morpholin-4-ylmethyl)-2,3-dihydro-4H-naphtho[2,1-e][1,3]oxazin-4-one | | | 383.2 |
| 78 | 8-fluoro-7-methyl-6-(4-(1H-pyrazol-1-yl)benzyl)-3-(tetrahydrofuran-2-ylmethyl)-2,3-dihydro-4H-1,3-benzoxazin-4-one | | | 422.1 |
| 79 | 6-((4-fluoropiperidin-1-yl)methyl)-3-((1S,2S)-2-hydroxycyclopentyl)-2,3-dihydro-4H-naphtho[2,1-e][1,3]oxazin-4-one | | | 399.2 |
| 80 | 6-((6-chloropyridin-3-yl)methyl)-2,3-dihydro-4H-naphto[2,1-e][1,3]oxazin-4-one | | | 325.1 |

TABLE 1-continued

| Ex. No. | IUPAC name | structural formula | salt | MS |
|---|---|---|---|---|
| 81 | 7-chloro-8-fluoro-3-((1S,2S)-2-hydroxycyclopentyl)-6-((6-methylpyridin-3-yl)methyl)-2,3-dihydro-4H-1,3-benzoxazin-4-one | | | 391.1 |
| 82 | 6-((6-(1,3-dimethyl-1H-pyrazol-4-yl)pyridin-3-yl)methyl)-7-methyl-3-(tetrahydrofuran-2-ylmethyl)-2,3-dihydro-4H-1,3-benzoxazin-4-one | | | 433.1 |
| 84 | 8-chloro-7-methyl-6-((6-methylpyridin-3-yl)methyl)-3-(tetrahydrofuran-2-ylmethyl)-2,3-dihydro-4H-1,3-benzoxazin-4-one | | | 387.1 |
| 85 | 6-((4,4-difluoropiperidin-1-yl)methyl)-3-(trans-2-hydroxycyclohexyl)-7-methyl-2,3-dihydro-4H-1,3-benzoxazin-4-one | | HCl | 395.3 |

TABLE 1-continued

| Ex. No. | IUPAC name | structural formula | salt | MS |
|---|---|---|---|---|
| 86 | 1,5-anhydro-2,4-dideoxy-2-(6-(4-methoxybenzyl)-7-methyl-4-oxo-2H-1,3-benzoxazin-3(4H)-yl)-threo-pentitol | | | 384.1 |
| 87 | 8-chloro-6-((6-chloropyridin-3-yl)methyl)-7-methyl-3-(tetrahydrofuran-2-ylmethyl)-2,3-dihydro-4H-1,3-benzoxazin-4-one | | HCl | 407.0 |
| 88 | 3-(2-fluorophenyl)-6-((6-(1-methyl-1H-pyrazol-4-yl)pyridin-3-yl)methyl)-2,3-dihydro-4H-1,3-benzoxazin-4-one | | | 415.2 |
| 89 | 8-fluoro-6-((2'-fluoro-2,4'-bipyridin-5-yl)methyl)-3-((1S,2S)-2-hydroxycyclopentyl)-7-methyl-2,3-dihydro-4H-1,3-benzoxazin-4-one | | | 452.1 |

TABLE 1-continued

| Ex. No. | IUPAC name | structural formula | salt | MS |
|---|---|---|---|---|
| 90 | 8-fluoro-3-((1S,2S)-2-hydroxycyclopentyl)-7-methyl-6-((2'-methyl-2,4'-bipyridin-5-yl)methyl)-2,3-dihydro-4H-1,3-benzoxazin-4-one | | | 448.2 |
| 91 | 6-((6-(1-ethyl-1H-pyrazol-3-yl)pyridin-3-yl)methyl)-8-fluoro-3-((1S,2S)-2-hydroxycyclopentyl)-7-methyl-2,3-dihydro-1,3-benzoxazin-4-one | | | 451.2 |
| 92 | 8-fluoro-3-((1S,2S)-2-hydroxycyclohexyl)-7-methyl-6-((6-(1-methyl-1H-pyrazol-3-yl)pyridin-3-yl)methyl)-2,3-dihydro-4H-1,3-benzoxazin-4-one | | | 451.2 |

TABLE 1-continued

| Ex. No. | IUPAC name | structural formula | salt | MS |
|---|---|---|---|---|
| 93 | 6-((6-(1,3-dimethyl-1H-pyrazol-4-yl)pyridin-3-yl)methyl)-8-fluoro-3-((1S,2S)-2-hydroxycyclopentyl)-7-methyl-2,3-dihydro-4H-1,3-benzoxazin-4-one | | | 451.1 |
| 94 | 3-(trans-2-hydroxycyclohexyl)-7-methyl-6-((6-(1H-pyrazol-1-yl)pyridin-3-yl)methyl)-2,3-dihydro-4H-1,3-benzoxazin-4-one (optical isomer: shorter retention time) | | | 419.2 |
| 95 | 3-(trans-2-hydroxycyclohexyl)-7-methyl-6-((6-(1H-pyrazol-1-yl)pyridin-3-yl)methyl)-2,3-dihydro-4H-1,3-benzoxazin-4-one (optical isomer: longer retention time) | | | 419.2 |

TABLE 1-continued

| Ex. No. | IUPAC name | structural formula | salt | MS |
|---|---|---|---|---|
| 96 | 8-chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one (optical isomer: shorter retention time) | | | 439.2 |
| 97 | 8-chloro-3-(trans-2-hydroxycyclopentyl)-7-methyl-6-((6-(1H-pyrazol-1-yl)pyridin-3-yl)methyl)-2,3-dihydro-4H-1,3-benzoxazin-4-one (optical isomer: longer retention time) | | | 439.2 |
| 98 | 1,5-anhydro-2,4-dideoxy-2-(7,8-dimethyl-4-oxo-6-((6-(1H-pyrazol-1-yl)pyridin-3-yl)methyl)-2H-1,3-benzoxazin-3(4H)-yl)-L-threo-pentitol | | | 435.2 |
| 99 | 8-chloro-3-((1S,2S)-2-hydroxycyclopentyl)-7-methyl-6-((6-(1-methyl-1H-pyrazol-3-yl)pyridin-3-yl)methyl)-2,3-dihydro-4H-1,3-benzoxazin-4-one | | | 453.2 |

TABLE 1-continued

| Ex. No. | IUPAC name | structural formula | salt | MS |
|---|---|---|---|---|
| 100 | 1,5-anhydro-2,4-dideoxy-2-(7,8-dimethyl-6-(4-(1-methyl-1H-pyrazol-3-yl)benzyl)-4-oxo-2H-1,3-benzoxazin-3(4H)-yl)-L-threo-pentitol | | | 448.2 |
| 101 | 8-fluoro-3-(2-hydroxy-2-methylpropyl)-7-methyl-6-(4-(1H-pyrazol-1-yl)benzyl)-2,3-dihydro-4H-1,3-benzoxazin-4-one | | | 410.2 |
| 102 | 1,5-anhydro-2,4-dideoxy-2-(8-fluoro-7-methyl-4-oxo-6-((6-(1H-pyrazol-1-yl)pyridin-3-yl)methyl)-2H-1,3-benzoxazin-3(4H)-yl)-L-threo-pentitol | | | 439.2 |

TABLE 1-continued

| Ex. No. | IUPAC name | structural formula | salt | MS |
|---|---|---|---|---|
| 103 | 1,5-anhydro-2,4-dideoxy-2-(7-methyl-4-oxo-6-((6-(1H-pyrazol-1-yl)pyridin-3-yl)methyl)-2H-1,3-benzooxazin-3(4H)-yl)-L-threo-pentitol | | | 421.2 |
| 104 | 3-((3S,4S)-4-hydroxytetrahydro-2H-pyran-3-yl)-7-methyl-6-(4-(1-methyl-1H-pyrazol-3-yl)benzyl)-2,3-dihydro-4H-1,3-benzoxazin-4-one Alias; 1,5-anhydro-2,4-dideoxy-2-(7-methyl-6-(4-(1-methyl-1H-pyrazol-3-yl)benzyl)-4-oxo-2H-1,3-benzoxazin-3(4H)-yl)-L-threo-pentitol | | | 434.2 |
| 105 | 8-fluoro-3-((1S,2S)-2-hydroxycyclopentyl)-7-methyl-6-(4-(6-methylpyridazin-4-yl)benzyl)-2,3-dihydro-4H-1,3-benzoxazin-4-one | | HCl | 448.2 |

TABLE 1-continued

| Ex. No. | IUPAC name | structural formula | salt | MS |
|---|---|---|---|---|
| 106 | 1,5-anhydro-2-(8-chloro-7-methyl-4-oxo-6-((6-(1H-pyrazol-1-yl)pyridin-3-yl)methyl)-2H-1,3-benzoxazin-3(4H)-yl)-2,4-dideoxy-L-threo-pentitol | | | 455.2 |
| 107 | 1,5-anhydro-2,4-dideoxy-2-(7-ethyl-4-oxo-6-(4-(1H-pyrazol-1-yl)benzyl)-2H-1,3-benzoxazin-3(4H)-yl)-L-threo-pentitol | | | 434.2 |
| 108 | 1,5-anhydro-2,4-dideoxy-2-(8-fluoro-7-methyl-6-(4-(1-methyl-1H-pyrazol-3-yl)benzyl)-4-oxo-2H-1,3-benzoxazin-3(4H)-yl)-L-threo-pentitol | | | 452.2 |
| 109 | 1,5-anhydro-2-(8-chloro-6-((6-methoxypyridin-3-yl)methyl)-7-methyl-4-oxo-2H-1,3-benzoxazin-3(4H)-yl)-2,4-deoxy-L-threo-pentitol | | | 419.1 |

TABLE 1-continued

| Ex. No. | IUPAC name | structural formula | salt | MS |
|---|---|---|---|---|
| 110 | 1,5-anhydro-2,4-dideoxy-2-(7,8-dimethyl-4-oxo-6-((6-vinylpyridin-3-yl)methyl)-2H-1,3-benzoxazin-3(4H)-yl)-L-threo-pentitol | | | 395.2 |
| 111 | 1,5-anhydro-2,4-dideoxy-2-(7,8-dimethyl-4-oxo-6-((6-((trimethylsilyl)ethynyl)-pyridin-3-yl)methyl)-2H-1,3-benzoxazin-3(4H)-yl)-L-threo-pentitol | | | 464.6 |
| 112 | 1,5-anhydro-2,4-dideoxy-2-(6-((6-ethynylpyridin-3-yl)methyl)-7,8-dimethyl-4-oxo-2H-1,3-benzoxazin-3(4H)-yl)-L-threo-pentitol | | | 392.5 |

TABLE 1-continued

| Ex. No. | IUPAC name | structural formula | salt | MS |
|---|---|---|---|---|
| 113 | 1,5-anhydro-2,3-dideoxy-3-(8-fluoro-7-methyl-4-oxo-6-(4-(1H-pyrazol-1-yl)benzyl)-2H-1,3-benzoxazin-3(4H)-yl)-L-threo-pentitol | | | 438.1 |
| 114 | 1,5-anhydro-2,3-dideoxy-3-(7-methyl-4-oxo-6-(4-(1H-pyrazol-1-yl)benzyl)-2H-1,3-benzoxazin-3(4H)-yl)-L-threo-pentitol | | | 420.2 |
| 115 | 1,5-anhydro-2,4-dideoxy-2-(8-fluoro-7-methyl-4-oxo-6-(pyrazolo[1,5-a]pyridin-5-ylmethyl)-2H-1,3-benzoxazin-3(4H)-yl)-L-threo-pentitol | | | 412.2 |
| 116 | 1,5-anhydro-2,4-dideoxy-2-(7,8-dimethyl-6-((2-methyl-2H-indazol-5-yl)methyl)-4-oxo-2H-1,3-benzoxazin-3(4H)-yl)-L-threo-pentitol | | | 422.1 |

TABLE 1-continued

| Ex. No. | IUPAC name | structural formula | salt | MS |
|---|---|---|---|---|
| 117 | 1,5-anhydro-2,4-dideoxy-2-(7,8-dimethyl-6-((2-methyl-2H-indazol-6-yl)methyl)-4-oxo-2H-1,3-benzoxazin-3(4H)-yl)-L-threo-pentitol | | | 422.4 |
| 118 | 1,5-anhydro-2,4-dideoxy-2-(7-ethyl-6-((6-methoxypyridin-3-yl)methyl)-4-oxo-2H-1,3-benzoxazin-3(4H)-yl)-L-threo-pentitol | | | 399.2 |
| 119 | 1,5-anhydro-2-(6-((6-chloropyridin-3-yl)methyl)-7-ethyl-4-oxo-2H-1,3-benzoxazin-3(4H)-yl)-2,4-dideoxy-L-threo-pentitol | | | 403.1 |
| 120 | 1,5-anhydro-2,4-dideoxy-2-(6-((6-ethenylpyridin-3-yl)methyl)-7-ethyl-4-oxo-2H-1,3-benzoxazin-3(4H)-yl)-L-threo-pentitol | | | 395.2 |

TABLE 1-continued

| Ex. No. | IUPAC name | structural formula | salt | MS |
|---|---|---|---|---|
| 121 | 1,5-anhydro-2,4-dideoxy-2-(4-oxo-6-(4-(1H-pyrazol-1-yl)benzyl)-7-vinyl-2H-1,3-benzoxazin-3(4H)-yl)-L-threo-pentitol | | | 432.2 |
| 122 | 6-((6-chloropyridin-3-yl)methyl)-3-((1S,2S)-2-hydroxycyclohexyl)-2,3-dihydro-4H-1,3-benzoxazin-4-one | | | 373.1 |
| 123 | 6-((6-ethynylpyridin-3-yl)methyl)-7-methyl-3-(tetrahydrofuran-2-ylmethyl)-2,3-dihydro-4H-1,3-benzoxazin-4-one | | | 363.2 |
| 124 | 8-fluoro-3-(2-hydroxycyclopentyl)-6-(4-(1H-pyrazol-1-yl)benzyl)-2,3-dihydro-4H-1,3-benzoxazin-4-one | | | 408.1 |

TABLE 1-continued

| Ex. No. | IUPAC name | structural formula | salt | MS |
|---|---|---|---|---|
| 125 | 1,5-anhydro-2-(6-((6-chloropyridin-3-yl)methyl)-4-oxo-2H-naphtho[2,1-e][1,3]oxazin-3(4H)-yl)-2,4-dideoxy-L-threo-pentitol | | | 425.1 |
| 126 | 3-((1S,2S)-2-hydroxycyclopentyl)-6-(piperidin-1-ylmethyl)-2,3-dihydro-4H-naphtho[2,1-e][1,3]oxazin-4-one | | | 381.2 |
| 127 | 3-((1S,2S)-2-hydroxycyclopentyl)-6-((4-methylpiperazin-1-yl)methyl)-2,3-dihydro-4H-naphtho[2,1-e][1,3]oxazin-4-one | | | 396.2 |
| 128 | methyl 1-((3-((1S,2S)-2-hydroxycyclopentyl)-4-oxo-3,4-dihydro-2H-naphtho[2,1-e][1,3]oxazin-6-yl)methyl)piperidine-4-carboxylate | | | 439.2 |

TABLE 1-continued

| Ex. No. | IUPAC name | structural formula | salt | MS |
|---|---|---|---|---|
| 129 | 3-((1S,2S)-2-hydroxycyclopentyl)-6-(pyrrolidin-1-ylmethyl)-2,3-dihydro-4H-naphtho[2,1-e][1,3]oxazin-4-one | | | 367.4 |
| 130 | 6-(((3R)-3-fluoropyrrolidin-1-yl)methyl)-3-((1S,2S)-2-hydroxycyclopentyl)-2,3-dihydro-4H-naphtho[2,1-e][1,3]oxazin-4-one | | | 385.1 |
| 131 | 6-((3-fluoroazetidin-1-yl)methyl)-3-((1S,2S)-2-hydroxycyclopentyl)-2,3-dihydro-4H-naphtho[2,1-e][1,3]oxazin-4-one | | | 371.1 |
| 132 | 3-((1S,2S)-2-hydroxycyclopentyl)-6-((4-methoxypiperidin-1-yl)methyl)-2,3-dihydro-4H-naphtho[2,1-e][1,3]oxazin-4-one | | | 411.2 |

TABLE 1-continued

| Ex. No. | IUPAC name | salt | MS |
|---|---|---|---|
| 133 | 1,5-anhydro-2,4-dideoxy-2-(6-((6-methylpyridin-3-yl)methyl)-4-oxo-2H-naphtho[2,1-e][1,3]oxazin-3(4H)-yl)-L-threo-pentitol | HCl | 405.1 |
| 134 | 3-((1S,2S)-2-hydroxycyclopentyl)-6-((3-(trifluoromethyl)pyrrolidin-1-yl)methyl)-2,3-dihydro-4H-naphtho[2,1-e][1,3]oxazin-4-one | | 435.1 |
| 135 | 3-((1S,2S)-2-hydroxycyclopentyl)-6-((3-methoxypyrrolidin-1-yl)methyl)-2,3-dihydro-4H-naphtho[2,1-e][1,3]oxazin-4-one | | 397.2 |
| 136 | 3-((1S,2S)-2-hydroxycyclopentyl)-6-(2-oxa-7-azaspiro[4.4]non-7-ylmethyl)-2,3-dihydro-4H-naphtho[2,1-e][1,3]oxazin-4-one | | 423.2 |

TABLE 1-continued

| Ex. No. | IUPAC name | structural formula | salt | MS |
|---|---|---|---|---|
| 137 | 1,5-anhydro-2,4-dideoxy-2-(7,8-dimethyl-6-((6-methylpyridin-3-yl)methyl)-4-oxo-2H-1,3-benzoxazin-3(4H)-yl)-L-threo-pentitol | | | 383.2 |
| 138 | 7-chloro-6-((6-chloropyridin-3-yl)methyl)-8-fluoro-3-((1S,2S)-2-hydroxycyclopentyl)-2,3-dihydro-4H-1,3-benzoxazin-4-one | | | 411.0 |
| 139 | 1,5-anhydro-2,4-dideoxy-2-(7-methyl-6-((6-methylpyridin-3-yl)methyl)-4-oxo-2H-1,3-benzoxazin-3(4H)-yl)-L-threo-pentitol | | | 369.2 |
| 140 | 6-((6-chloropyridin-3-yl)methyl)-3-((1S,2S)-2-hydroxycyclohexyl)-7-methyl-2,3-dihydro-4H-1,3-benzoxazin-4-one | | | 387.1 |

TABLE 1-continued

| Ex. No. | IUPAC name | structural formula | salt | MS |
|---|---|---|---|---|
| 141 | 1,5-anhydro-2,4-dideoxy-2-(7-methyl-4-oxo-6-(4-(2H-1,2,3-triazol-2-yl)benzyl)-2H-1,3-benzoxazin-3(4H)-yl)-L-threo-pentitol | | | 421.1 |
| 142 | 1,5-anhydro-2,4-dideoxy-2-(7,8-dimethoxy-4-oxo-6-(4-(2H-1,2,3-triazol-2-yl)benzyl)-2H-1,3-benzoxazin-3(4H)-yl)-L-threo-pentitol | | | 435.2 |

Formulation Example 1

| | |
|---|---|
| (1) Compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is granulated by passing through a 1 mm mesh sieve while using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of saccharose, titanium dioxide, talc and gum arabic. The coated tablets are glazed with beeswax to give 1000 coated tablets.

Formulation Example 2

| | |
|---|---|
| (1) Compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), and the obtained granules are dried, and mixed with lactose (70.0 g) and cornstarch (50.0 g). The mixture is compressed to give 1000 tablets.

Experimental Example 1

Measurement of M1 Receptor Positive Allosteric Modulator (M1PAM) Activity

The activity of a test compound in the presence of acetylcholine at EC20 concentration (final concentration 0.8-1.0 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and a dye solution (prepared by adding Recording medium (DOJINDO LABORATORIES) to a final concentration of 1×concentration, Fluo-4 AM (DOJINDO LABORATORIES) to a final concentration of 2.5 µg/mL, Pluronic F127

(DOJINDO LABORATORIES) to a final concentration of 0.08%, and probenecid (DOJINDO LABORATORIES) to a final concentration of 1.25 mM to assay buffer (HBSS (Invitrogen), 20 mM HEPES (Invitrogen), 0.1% BSA (Wako Pure Chemical Industries, Ltd.))) was added at 30 μL/well. The cells were left standing in the incubator at 37° C., 5% $CO_2$ for 30 min, and further left standing at room temperature for 30 min. A test compound prepared by diluting with assay buffer containing 3.2-4.0 nM acetylcholine was added at 10 μL/well, and the fluorescence was measured by FLIPRtetra (Molecular Devices) for 1 min every 1 second. With the definition that the amount of change in the fluorescence on addition of acetylcholine (final concentration 1 μM) is 100% and that on addition of DMSO instead of a test compound is 0%, the activity (%) of the test compound was calculated, and the inflection point in the concentration-dependent curve of the test compound was calculated as IP values. The results are shown in Table 2.

TABLE 2

| Example No. | IP value (nM) | activity (%) at 10 μM |
|---|---|---|
| 1 | 1.8 | 96 |
| 2 | 2.5 | 106 |
| 3 | 2.5 | 103 |
| 4 | 3.2 | 109 |
| 5 | 8.5 | 104 |
| 6 | 7.0 | 102 |
| 7 | 7.9 | 108 |
| 8 | 9.6 | 105 |
| 9 | 4.6 | 98 |
| 10 | 9.1 | 109 |
| 11 | 8.5 | 95 |
| 12 | 15 | 89 |
| 13 | 6.0 | 88 |
| 14 | 15 | 106 |
| 15 | 19 | 92 |
| 16 | 20 | 102 |
| 17 | 27 | 112 |
| 18 | 37 | 107 |
| 19 | 45 | 105 |
| 20 | 24 | 85 |
| 21 | 16 | 95 |
| 22 | 0.69 | 105 |
| 23 | 2.0 | 114 |
| 24 | 3.1 | 94 |
| 25 | 4.2 | 101 |
| 26 | 5.4 | 119 |
| 27 | 6.0 | 105 |
| 28 | 20 | 108 |
| 29 | 14 | 106 |
| 30 | 8.6 | 102 |
| 31 | 17 | 99 |
| 32 | 37 | 108 |
| 33 | 39 | 104 |
| 34 | 53 | 96 |
| 35 | 5.8 | 109 |
| 36 | 12 | 108 |
| 37 | 1.2 | 109 |
| 38 | 1.5 | 99 |
| 39 | 1.5 | 88 |
| 40 | 1.6 | 98 |
| 41 | 1.8 | 104 |
| 42 | 2.0 | 124 |
| 43 | 2.4 | 93 |
| 44 | 3.9 | 99 |
| 45 | 4.8 | 92 |
| 46 | 4.9 | 109 |
| 47 | 5.3 | 110 |
| 48 | 7.4 | 106 |
| 49 | 8.0 | 108 |
| 50 | 8.6 | 120 |
| 51 | 9.7 | 101 |
| 52 | 11 | 101 |
| 53 | 11 | 96 |
| 54 | 11 | 116 |
| 55 | 14 | 98 |
| 56 | 16 | 109 |
| 57 | 16 | 106 |
| 58 | 16 | 94 |
| 59 | 21 | 99 |
| 60 | 22 | 105 |
| 61 | 23 | 92 |
| 62 | 27 | 91 |
| 63 | 32 | 99 |
| 64 | 34 | 99 |
| 65 | 35 | 99 |
| 66 | 44 | 93 |
| 67 | 46 | 98 |
| 68 | 48 | 90 |
| 69 | 51 | 93 |
| 70 | 52 | 104 |
| 71 | 53 | 105 |
| 72 | 57 | 100 |
| 73 | 59 | 97 |
| 74 | 59 | 104 |
| 75 | 60 | 102 |
| 76 | 63 | 93 |
| 77 | 63 | 104 |
| 78 | 75 | 104 |
| 79 | 78 | 97 |
| 80 | 81 | 97 |
| 81 | 86 | 110 |
| 82 | 90 | 93 |
| 84 | 96 | 93 |
| 85 | 110 | 104 |
| 86 | 100 | 99 |
| 87 | 160 | 93 |
| 88 | 230 | 115 |
| 125 | 3.8 | 89 |
| 133 | 3.6 | 91 |
| 137 | 14 | 104 |

Experimental Example 2

Measurement of M1 Receptor Positive Allosteric Modulator (M1PAM) Activity

The activity of a test compound in the presence of acetylcholine at EC20 concentration (final concentration 0.8-1.0 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and a dye solution (prepared by adding Recording medium (DOJINDO LABORATORIES) to a final concentration of 1×concentration, Fluo-4 AM (DOJINDO LABORATORIES) to a final concentration of 2.5 μg/mL, Pluronic F127 (DOJINDO LABORATORIES) to a final concentration of 0.08%, and probenecid (DOJINDO LABORATORIES) to a final concentration of 1.25 mM to assay buffer (HBSS (Invitrogen), 20 mM HEPES (Invitrogen), 0.1% BSA (Wako Pure Chemical Industries, Ltd.))) was added at 30 μL/well. The cells were left standing in the incubator at 37° C., 5% $CO_2$ for 30 min, and further left standing at room temperature for 30 min. A test compound prepared by diluting with assay buffer containing 3.2-4.0 nM acetylcholine was added at 10 μL/well, and the fluorescence was measured by FDSS/μ cell (Hamamatsu Photonics K.K.) for 1 min every 1 second. With the definition that the amount of change in the fluorescence on addition of acetylcholine (final concentration 1 μM) is 100% and that on addition of DMSO instead of a test compound is 0%, the activity (%) of the test compound was calculated, and the inflection point in the concentration-dependent curve of the test compound was calculated as IP values. The results are shown in Table 3.

TABLE 3

| Example No. | IP value (nM) | activity (%) at 10 μM |
| --- | --- | --- |
| 89 | 12 | 102 |
| 90 | 4.0 | 102 |
| 91 | 4.0 | 105 |
| 92 | 3.4 | 101 |
| 93 | 4.6 | 103 |
| 95 | 13 | 102 |
| 97 | 6.8 | 99 |
| 98 | 4.9 | 103 |
| 99 | 2.9 | 97 |
| 100 | 4.4 | 99 |
| 101 | 61 | 91 |
| 102 | 8.7 | 98 |
| 103 | 15 | 103 |
| 104 | 4.5 | 99 |
| 105 | 5.6 | 98 |
| 106 | 6.9 | 113 |
| 107 | 5.5 | 99 |
| 108 | 5.3 | 99 |
| 109 | 5.7 | 97 |
| 110 | 4.8 | 99 |
| 111 | 68 | 96 |
| 112 | 9.1 | 99 |
| 116 | 7.0 | 96 |
| 118 | 47 | 116 |
| 140 | 10 | 101 |
| 142 | 38 | 99 |

Experimental Example 3

Measurement of Myo-Inositol 1 Phosphate (IP1)

Animals used were male Long-Evans rats. They were used after acclimation for at least 1 week. Test compounds were suspended in 0.5% (w/v) aqueous methylcellulose solution, and the suspension was orally administered to the rats. After a given time, lithium chloride dissolved in saline was subcutaneously administered into the rats. After a given time, their bilateral hippocampi were isolated from the rats, and the wet weight thereof was measured. The isolated hippocampi were homogenized with HEPES (registered trademark) buffer, followed by centrifugation. The IP1 and protein concentrations in the supernatant were measured by IP-One HTRF assay kit (Cisbio Bioassays) and BCA protein assay kit (Thermo Scientific), respectively. The level of the IP1 production was expressed as the ratio of the concentration of IP1 to that of protein. The increase rate of the IP1 production was shown as a relative value when Vehicle administration group as 100%. The results are shown in Table 4.

TABLE 4

| test compound | increase rate (%) at 10 mg/kg |
| --- | --- |
| Example No. 13 | 102 |
| Example No. 24 | 26 |
| Example No. 28 | 36 |
| Example No. 104 | 86 |

Experimental Example 4

Novel Object Recognition Test

Novel object recognition test is comprised of two trials called the acquisition and the retention trials. Scopolamine-induced memory deficits models were used for the test, and animals used were male Long-Evans rats. On the day before the test, for acclimation, the rats were allowed to freely move about the test box (40×40×50 cm) for 10 minutes. On the test day, the rats were acclimated to the test room for about 1 hr prior to the test. The test compounds were orally administered to the rats in a single dose a given time before the acquisition trial. For induction of learning and memory deficits, scopolamine (0.1 mg/kg) was subcutaneously administered into the rats 30 min before the acquisition trial. For the acquisition trial, two identical objects (A1, A2) were placed in the test box. The rats were put in the test box for 3 min, and the duration exploring each object was measured. The retention trial was performed 4 hr after the acquisition trial. For the retention trial, one familiar object (A3) used for the acquisition trial and one novel object (B) having a different shape from A3 were placed in the test box. After setting the objects, the rats were introduced into the test box and retention trial was performed for 3 min. The duration for exploring each object in the acquisition trial and the retention trial was measured, and the exploration rate of novel object was calculated. The exploration rate of novel object was expressed as (the duration exploring the novel object)/[(the duration exploring the novel object)+(the duration exploring the familiar object)]×100(%) at mean±standard error. The results are shown below.

exploration rate of novel object (%)
  control group: 62.3±2.6%
  solvent-scopolamine group: 46.9±4.2%
  Example No. 13 (1 mg/kg)-scopolamine group: 60.2±3.0%
  control group: 66.5±1.4%
  solvent-scopolamine group: 55.6±1.6%
  Example No. 24 (3 mg/kg)-scopolamine group: 63.5±2.4%
  control group: 62.4±3.2%
  solvent-scopolamine group: 48.4±2.0%
  Example No. 28 (10 mg/kg)-scopolamine group: 56.0±2.2%
  control group: 63.6±2.2%
  solvent-scopolamine group: 53.6±0.9%
  Example No. 104 (3 mg/kg)-scopolamine group: 61.6±2.2%

INDUSTRIAL APPLICABILITY

The compound of the present invention may be useful as a cholinergic muscarinic M1 receptor positive allosteric modulator, or a medicament such as an agent for the prophylaxis or treatment of Alzheimer's disease, schizophrenia, pain, sleep disorder, Parkinson's disease dementia, dementia with Lewy bodies and the like.

This application is based on patent application Nos. 2015-129043 and 2015-206797 filed in Japan, the contents of which are encompassed in full herein.

The invention claimed is:

1. A method for treating Alzheimer's disease, schizophrenia, cognitive impairment associated with schizophrenia, pain, sleep disorder, Parkinson's disease dementia, Parkinson's disease, or dementia with Lewy bodies in a mammal, comprising: administering an effective amount of 8-chloro-6-((6-chloropyridin-3-yl)methyl)-3-((1S,2S)-2-hydroxycyclopentyl)-7-methyl-2,3-dihydro-4H-1,3-benzoxazin-4-one or a salt thereof to the mammal.

2. A method for treating Alzheimer's disease, schizophrenia, cognitive impairment associated with schizophrenia, pain, sleep disorder, Parkinson's disease dementia, Parkinson's disease, or dementia with Lewy bodies in a mammal, comprising: administering an effective amount of 3-((3S,4S)-4-hydroxytetrahydro-2H-pyran-3-yl)-7-methyl-6-(4-(1-methyl-1H-pyrazol-3-yl)benzyl)-2,3-dihydro-4H-1,3-benzoxazin-4-one or a salt thereof to the mammal.

* * * * *